(12) United States Patent
Erbey, II et al.

(10) Patent No.: US 11,918,754 B2
(45) Date of Patent: *Mar. 5, 2024

(54) URETERAL AND BLADDER CATHETERS AND METHODS OF INDUCING NEGATIVE PRESSURE TO INCREASE RENAL PERFUSION

(71) Applicant: Roivios Limited, Nassau (BS)

(72) Inventors: John R. Erbey, II, Milton, GA (US);
Jacob L. Upperco, Atlanta, GA (US);
David E. Orr, Piedmont, SC (US)

(73) Assignee: Roivios Limited, Nassau (BS)

( * ) Notice: Subject to any disclaimer, the term of this patent is extended or adjusted under 35 U.S.C. 154(b) by 330 days.

This patent is subject to a terminal disclaimer.

(21) Appl. No.: 17/173,262

(22) Filed: Feb. 11, 2021

(65) Prior Publication Data

US 2021/0162168 A1    Jun. 3, 2021

Related U.S. Application Data

(63) Continuation of application No. 15/879,976, filed on Jan. 25, 2018, now Pat. No. 11,040,172, which is a
(Continued)

(51) Int. Cl.
*A61M 25/00* (2006.01)
*A61M 1/00* (2006.01)
(Continued)

(52) U.S. Cl.
CPC .......... *A61M 25/0017* (2013.01); *A61M 1/84* (2021.05); *A61M 25/0041* (2013.01);
(Continued)

(58) Field of Classification Search
CPC ...................... A61M 25/04; A61M 2025/0293
See application file for complete search history.

(56) References Cited

U.S. PATENT DOCUMENTS

| 1,870,942 A | 8/1932 | Beatty |
| 2,285,980 A | 6/1942 | Jeckel |
| (Continued) |

FOREIGN PATENT DOCUMENTS

| AU | 2013332448 A1 | 4/2015 |
| CA | 1243581 A | 10/1988 |
| (Continued) |

OTHER PUBLICATIONS

Bart et al.; "Ultrafiltration in Decompensated Heart Failure with Cardiorenal Syndrome"; N Engl J Med; 2012; p. 2296-2304; vol. 367.

(Continued)

*Primary Examiner* — Adam Marcetich
(74) *Attorney, Agent, or Firm* — The Webb Law Firm

(57) ABSTRACT

A ureteral catheter for placement in a kidney, renal pelvis, and/or in a ureter adjacent to the renal pelvis of a patient, includes: an elongated tube having a proximal end, a distal end, and a sidewall extending therebetween defining at least one drainage lumen extending through the tube, wherein a proximal portion of the elongated tube is essentially free of or free of openings; and an expandable retention portion which defines a three-dimensional shape positioned to maintain fluid flow from the kidney through at least the distal end of the tube and inhibit tissue of the ureter or renal pelvis from occluding the at least one drainage lumen at the distal end of the elongated tube upon application of negative pressure through the drainage lumen, wherein the three-dimensional space defined by the expandable retention portion encloses at least a portion of the distal end of the elongated tube.

27 Claims, 24 Drawing Sheets

Related U.S. Application Data continuation-in-part of application No. 15/687,064, filed on Aug. 25, 2017, now Pat. No. 10,765,834, and a continuation-in-part of application No. 15/411,884, filed on Jan. 20, 2017, now Pat. No. 10,512,713, which is a continuation-in-part of application No. 15/214,955, filed on Jul. 20, 2016, now Pat. No. 10,307,564, said application No. 15/879,976 is a continuation-in-part of application No. 15/687,083, filed on Aug. 25, 2017, now Pat. No. 10,926,062, which is a continuation-in-part of application No. 15/411,884, filed on Jan. 20, 2017, now Pat. No. 10,512,713, which is a continuation-in-part of application No. 15/214,955, filed on Jul. 20, 2016, now Pat. No. 10,307,564, said application No. 15/879,976 is a continuation-in-part of application No. 15/745,823, filed as application No. PCT/US2016/043101 on Jul. 20, 2016, now abandoned.

(60) Provisional application No. 62/300,025, filed on Feb. 25, 2016, provisional application No. 62/278,721, filed on Jan. 14, 2016, provisional application No. 62/260,966, filed on Nov. 30, 2015, provisional application No. 62/194,585, filed on Jul. 20, 2015, provisional application No. 62/489,789, filed on Apr. 25, 2017, provisional application No. 62/489,831, filed on Apr. 25, 2017.

(51) Int. Cl.
*A61M 25/04* (2006.01)
*A61M 25/10* (2013.01)

(52) U.S. Cl.
CPC ............... *A61M 25/10* (2013.01); *A61M 1/80* (2021.05); *A61M 25/04* (2013.01); *A61M 2210/1082* (2013.01)

(56) References Cited

U.S. PATENT DOCUMENTS

| | | |
|---|---|---|
| 2,649,092 A | 8/1953 | Wallace |
| 3,108,595 A | 10/1963 | Overment |
| 3,397,699 A | 8/1968 | Kohl |
| 3,561,431 A | 2/1971 | Pannier, Jr. |
| 3,707,967 A | 1/1973 | Kitrilakis |
| 3,875,941 A | 4/1975 | Adair |
| 3,938,529 A | 2/1976 | Gibbons |
| 3,938,530 A | 2/1976 | Santomieri |
| 3,943,929 A | 3/1976 | Patel |
| 4,265,243 A | 5/1981 | Taylor |
| 4,306,557 A | 12/1981 | North |
| 4,324,663 A | 4/1982 | Hirel et al. |
| 4,349,029 A | 9/1982 | Mott |
| 4,425,124 A | 1/1984 | Womack |
| 4,437,856 A | 3/1984 | Valli |
| 4,531,933 A | 7/1985 | Norton et al. |
| 4,568,338 A | 2/1986 | Todd |
| 4,571,241 A | 2/1986 | Christopher |
| 4,575,371 A | 3/1986 | Nordqvist et al. |
| 4,629,015 A | 12/1986 | Fried et al. |
| 4,681,564 A | 7/1987 | Landreneau |
| 4,710,169 A | 12/1987 | Christopher |
| 4,738,667 A | 4/1988 | Galloway |
| 4,813,935 A | 3/1989 | Haber et al. |
| 4,834,724 A | 5/1989 | Geiss et al. |
| 4,932,938 A | 6/1990 | Goldberg et al. |
| 4,935,004 A | 6/1990 | Cruz |
| 4,945,895 A | 8/1990 | Takai et al. |
| 4,950,228 A | 8/1990 | Knapp, Jr. et al. |
| 4,957,479 A | 9/1990 | Roemer |
| 5,009,639 A | 4/1991 | Keymling |
| 5,011,488 A | 4/1991 | Ginsburg |
| 5,041,093 A | 8/1991 | Chu |
| 5,044,902 A | 9/1991 | Malbec |
| 5,059,169 A | 10/1991 | Zilber |
| 5,078,684 A | 1/1992 | Yasuda |
| 5,098,440 A | 3/1992 | Hillstead |
| 5,116,309 A | 5/1992 | Coll |
| 5,141,502 A | 8/1992 | Macaluso, Jr. |
| 5,193,533 A | 3/1993 | Body et al. |
| 5,256,146 A | 10/1993 | Ensminger et al. |
| 5,370,690 A | 12/1994 | Barrett |
| 5,401,257 A | 3/1995 | Chevalier, Jr. et al. |
| 5,451,215 A | 9/1995 | Wolter |
| 5,451,218 A | 9/1995 | Moore |
| 5,505,717 A | 4/1996 | Moore |
| 5,514,112 A | 5/1996 | Chu et al. |
| 5,523,092 A | 6/1996 | Hanson et al. |
| 5,536,274 A | 7/1996 | Neuss |
| 5,540,701 A | 7/1996 | Sharkey et al. |
| 5,554,144 A | 9/1996 | Wallace et al. |
| 5,562,622 A | 10/1996 | Tihon |
| 5,599,291 A | 2/1997 | Balbierz et al. |
| 5,647,843 A | 7/1997 | Mesrobian et al. |
| 5,662,713 A | 9/1997 | Andersen et al. |
| 5,709,874 A | 1/1998 | Hanson et al. |
| 5,727,555 A | 3/1998 | Chait |
| 5,769,821 A | 6/1998 | Abrahamson et al. |
| 5,785,641 A | 7/1998 | Davis |
| 5,795,319 A | 8/1998 | Ali |
| 5,865,764 A | 2/1999 | Moorhead |
| 5,873,865 A | 2/1999 | Horzewski et al. |
| 5,895,398 A | 4/1999 | Wensel et al. |
| 5,902,336 A | 5/1999 | Mishkin |
| 5,915,386 A | 6/1999 | Lloyd et al. |
| 5,957,867 A | 9/1999 | Lloyd et al. |
| 5,972,019 A | 10/1999 | Engelson et al. |
| 5,989,207 A | 11/1999 | Hughes |
| 6,066,113 A | 5/2000 | Overtoom |
| 6,090,069 A | 7/2000 | Walker |
| 6,111,520 A | 8/2000 | Allen et al. |
| 6,200,485 B1 | 3/2001 | Kitaevich et al. |
| 6,214,037 B1 | 4/2001 | Mitchell et al. |
| 6,283,940 B1 | 9/2001 | Mulholland |
| 6,332,892 B1 | 12/2001 | Desmond, III et al. |
| 6,364,868 B1 | 4/2002 | Ikeguchi |
| 6,402,736 B1 | 6/2002 | Brown et al. |
| 6,442,415 B1 | 8/2002 | Bis et al. |
| 6,461,346 B1 | 10/2002 | Buelna |
| 6,478,778 B1 | 11/2002 | Jacobsen et al. |
| 6,482,222 B1 | 11/2002 | Bruckheimer et al. |
| 6,500,158 B1 | 12/2002 | Keguchi |
| 6,558,350 B1 | 5/2003 | Hart et al. |
| 6,569,150 B2 | 5/2003 | Teague et al. |
| 6,620,202 B2 | 9/2003 | Bottcher et al. |
| 6,648,863 B2 | 11/2003 | Reever |
| 6,676,623 B2 | 1/2004 | Whitmore, III |
| 6,685,744 B2 | 2/2004 | Gellman et al. |
| 6,702,834 B1 | 3/2004 | Boylan et al. |
| 6,764,519 B2 | 7/2004 | Whitmore, III |
| 6,780,322 B1 | 8/2004 | Bissler et al. |
| 6,837,868 B1 | 1/2005 | Fajnsztajn |
| 7,025,753 B2 | 4/2006 | Reever |
| 7,037,345 B2 | 5/2006 | Bottcher et al. |
| 7,044,981 B2 | 5/2006 | Liu et al. |
| 7,316,663 B2 | 1/2008 | Whitmore, III |
| 7,329,226 B1 | 2/2008 | Ni et al. |
| 7,396,366 B2 | 7/2008 | Ward |
| 7,507,218 B2 | 3/2009 | Aliski et al. |
| 7,550,978 B2 | 6/2009 | Joy et al. |
| 7,603,170 B2 | 10/2009 | Hatlestad et al. |
| 7,682,401 B2 | 3/2010 | Deal |
| 7,722,677 B2 | 5/2010 | Ward |
| 7,727,222 B2 | 6/2010 | Da Silva et al. |
| 7,736,354 B2 | 6/2010 | Gelfand et al. |
| 7,758,562 B2 | 7/2010 | Gelfand et al. |
| 7,758,563 B2 | 7/2010 | Gelfand et al. |
| 7,766,961 B2 | 8/2010 | Patel et al. |
| 7,837,667 B2 | 11/2010 | Gelfand et al. |
| 7,850,704 B2 | 12/2010 | Burnett et al. |

(56) References Cited

U.S. PATENT DOCUMENTS

| | | |
|---|---|---|
| 7,857,803 B1 | 12/2010 | Salinas et al. |
| 7,879,020 B1 | 2/2011 | Salinas et al. |
| 7,938,817 B2 | 5/2011 | Gelfand et al. |
| 7,972,292 B2 | 7/2011 | Behl et al. |
| 8,007,460 B2 | 8/2011 | Gelfand et al. |
| 8,021,307 B2 | 9/2011 | White et al. |
| 8,075,513 B2 | 12/2011 | Rudko et al. |
| 8,088,170 B2 | 1/2012 | Whitmore, III |
| 8,105,317 B2 | 1/2012 | Reever et al. |
| 8,152,786 B2 | 4/2012 | Shapland et al. |
| 8,157,785 B2 | 4/2012 | Salinas et al. |
| 8,177,741 B2 | 5/2012 | Hammack et al. |
| 8,252,065 B2 | 8/2012 | Ward |
| 8,328,877 B2 | 12/2012 | Gellman |
| 8,444,623 B2 | 5/2013 | Gelfand et al. |
| 8,486,010 B2 | 7/2013 | Nomura |
| 8,512,795 B2 | 8/2013 | Dias et al. |
| 8,568,387 B2 | 10/2013 | Paz |
| 8,585,675 B2 | 11/2013 | Salinas et al. |
| 8,597,260 B2 | 12/2013 | Tucker |
| 8,597,273 B2 | 12/2013 | Salinas et al. |
| 8,747,388 B2 | 6/2014 | Pandey et al. |
| 8,795,305 B2 | 8/2014 | Martin et al. |
| 8,827,924 B2 | 9/2014 | Paz et al. |
| 8,852,289 B2 | 10/2014 | Whitmore, III |
| 8,865,063 B2 | 10/2014 | Burnett |
| 8,932,320 B1 | 1/2015 | Janardhan et al. |
| 9,014,815 B2 | 4/2015 | Yang et al. |
| 9,060,888 B2 | 6/2015 | Gellman |
| 9,308,348 B2 | 4/2016 | Mulvihill et al. |
| 9,339,636 B1 | 5/2016 | Khan et al. |
| 9,682,220 B2 | 6/2017 | Schertiger et al. |
| 9,744,331 B2 | 8/2017 | Erbey, II et al. |
| 9,750,634 B2 | 9/2017 | Bar-Am |
| 9,788,928 B2 | 10/2017 | Forsell |
| 9,849,224 B2 | 12/2017 | Angwin et al. |
| 9,980,663 B2 | 5/2018 | Wabel et al. |
| 10,182,747 B2 | 1/2019 | Charlez et al. |
| 10,226,606 B2 | 3/2019 | Wan et al. |
| 10,307,566 B2 | 6/2019 | Bishawi |
| 10,449,329 B2 | 10/2019 | Foley et al. |
| 11,040,180 B2 | 6/2021 | Erbey, II et al. |
| 2001/0053936 A1 | 12/2001 | Whitmore, III |
| 2001/0056273 A1 | 12/2001 | Ewers |
| 2002/0052576 A1 | 5/2002 | Massengale |
| 2002/0062148 A1 | 5/2002 | Hart |
| 2002/0068093 A1 | 6/2002 | Trogolo et al. |
| 2002/0082547 A1 | 6/2002 | Deniega et al. |
| 2002/0085951 A1 | 7/2002 | Gelfand et al. |
| 2002/0143292 A1 | 10/2002 | Flinchbaugh |
| 2002/0143389 A1 | 10/2002 | St. Pierre |
| 2002/0177902 A1 | 11/2002 | Rioux et al. |
| 2002/0183852 A1 | 12/2002 | McWeeney |
| 2002/0183853 A1 | 12/2002 | Mitchell et al. |
| 2002/0188246 A1 | 12/2002 | Hayner et al. |
| 2002/0193667 A1 | 12/2002 | McNair |
| 2003/0009132 A1 | 1/2003 | Schwartz et al. |
| 2003/0018291 A1 | 1/2003 | Hill et al. |
| 2003/0060806 A1 | 3/2003 | Ikeguchi |
| 2003/0069534 A1 | 4/2003 | Work et al. |
| 2003/0074082 A1 | 4/2003 | Bottcher et al. |
| 2003/0109930 A1 | 6/2003 | Bluni et al. |
| 2003/0120261 A1 | 6/2003 | Gellman |
| 2003/0135147 A1 | 7/2003 | Rosenberg et al. |
| 2003/0135195 A1 | 7/2003 | Jimenez et al. |
| 2003/0144623 A1 | 7/2003 | Heath et al. |
| 2003/0153970 A1 | 8/2003 | Rao et al. |
| 2003/0171708 A1 | 9/2003 | Segura et al. |
| 2003/0176831 A1 | 9/2003 | Gellman et al. |
| 2003/0181842 A1 | 9/2003 | Gellman |
| 2003/0181887 A1 | 9/2003 | Castillo Deniega et al. |
| 2003/0191452 A1 | 10/2003 | Meglin et al. |
| 2003/0195456 A1 | 10/2003 | Robertson |
| 2003/0195537 A1 | 10/2003 | Dubrul et al. |
| 2003/0199805 A1 | 10/2003 | McWeeney |
| 2003/0216710 A1 | 11/2003 | Hurt |
| 2003/0224033 A1 | 12/2003 | Li et al. |
| 2004/0019358 A1 | 1/2004 | Kear |
| 2004/0054315 A1 | 3/2004 | Levin et al. |
| 2004/0054351 A1 | 3/2004 | Deniega et al. |
| 2004/0057037 A1 | 3/2004 | Ohishi et al. |
| 2004/0073194 A1 | 4/2004 | Olsen et al. |
| 2004/0097891 A1 | 5/2004 | Bolmsjo |
| 2004/0129616 A1 | 7/2004 | Mori et al. |
| 2004/0143209 A1 | 7/2004 | Liu et al. |
| 2004/0147871 A1 | 7/2004 | Burnett |
| 2004/0167415 A1 | 8/2004 | Gelfand et al. |
| 2004/0167634 A1 | 8/2004 | Atala et al. |
| 2004/0193098 A1 | 9/2004 | Wentling et al. |
| 2005/0042240 A1 | 2/2005 | Utterberg et al. |
| 2005/0049575 A1 | 3/2005 | Snell et al. |
| 2005/0049577 A1 | 3/2005 | Snell et al. |
| 2005/0101941 A1 | 5/2005 | Hakky et al. |
| 2005/0107736 A1 | 5/2005 | Landman et al. |
| 2005/0124969 A1 | 6/2005 | Fitzgerald et al. |
| 2005/0124978 A1 | 6/2005 | Kim |
| 2005/0177102 A1 | 8/2005 | Hart et al. |
| 2005/0187564 A1 | 8/2005 | Jayaraman |
| 2005/0240141 A1 | 10/2005 | Aliski et al. |
| 2005/0240280 A1 | 10/2005 | Aliski et al. |
| 2005/0256441 A1 | 11/2005 | Lotan et al. |
| 2005/0256447 A1 | 11/2005 | Richardson et al. |
| 2005/0288722 A1 | 12/2005 | Eigler et al. |
| 2006/0015015 A1 | 1/2006 | Kawamoto et al. |
| 2006/0015089 A1 | 1/2006 | Meglin et al. |
| 2006/0052879 A1 | 3/2006 | Kolb |
| 2006/0074388 A1 | 4/2006 | Dextradeur et al. |
| 2006/0074409 A1 | 10/2006 | Schuermann |
| 2006/0229553 A1 | 10/2006 | Hammack et al. |
| 2006/0229573 A1 | 10/2006 | Lamborne |
| 2006/0259151 A1 | 11/2006 | Ward |
| 2006/0271019 A1 | 11/2006 | Stoller et al. |
| 2007/0010797 A1 | 1/2007 | Nishtala et al. |
| 2007/0010798 A1 | 1/2007 | Stoller et al. |
| 2007/0055198 A1 | 3/2007 | O'Mahony et al. |
| 2007/0073271 A1 | 3/2007 | Brucker et al. |
| 2007/0088333 A1 | 4/2007 | Levin et al. |
| 2007/0112302 A1 | 5/2007 | Yu |
| 2007/0197957 A1 | 8/2007 | Hunter et al. |
| 2007/0208291 A1 | 9/2007 | Patel |
| 2007/0213665 A1 | 9/2007 | Curtin et al. |
| 2007/0219488 A1 | 9/2007 | Francescatti |
| 2007/0255230 A1 | 11/2007 | Gross et al. |
| 2008/0051678 A1 | 2/2008 | Lindahl |
| 2008/0051691 A1 | 2/2008 | Dragoon et al. |
| 2008/0058650 A1 | 3/2008 | Saadat et al. |
| 2008/0097463 A1 | 4/2008 | House |
| 2008/0119907 A1 | 5/2008 | Stahmann |
| 2008/0142023 A1 | 6/2008 | Schmid et al. |
| 2008/0183299 A1 | 7/2008 | Monga et al. |
| 2008/0215247 A1 | 9/2008 | Tonelli et al. |
| 2008/0243091 A1 | 10/2008 | Humphreys et al. |
| 2008/0255550 A1 | 10/2008 | Bell |
| 2008/0281291 A1 | 11/2008 | Tihon et al. |
| 2008/0288082 A1 | 11/2008 | Deal |
| 2008/0312550 A1 | 12/2008 | Nishtala et al. |
| 2009/0024091 A1 | 1/2009 | Li et al. |
| 2009/0030370 A1 | 1/2009 | Nishtala et al. |
| 2009/0030435 A1 | 1/2009 | Burnett et al. |
| 2009/0043229 A1 | 2/2009 | Dunn et al. |
| 2009/0088677 A1 | 4/2009 | Cohen |
| 2009/0093748 A1 | 4/2009 | Patterson et al. |
| 2009/0105719 A1 | 4/2009 | Honey et al. |
| 2009/0143713 A1 | 6/2009 | Van Dam et al. |
| 2009/0162530 A1 | 6/2009 | Nesbitt |
| 2009/0171137 A1 | 7/2009 | Farnan et al. |
| 2009/0171241 A1 | 7/2009 | Garcia et al. |
| 2009/0281507 A1 | 11/2009 | Humphreys |
| 2009/0318844 A1 | 12/2009 | Burnett |
| 2010/0057000 A1 | 3/2010 | Melsheimer et al. |
| 2010/0081148 A1 | 4/2010 | Singbartl et al. |
| 2010/0086580 A1 | 4/2010 | Nyman et al. |
| 2010/0121159 A1 | 5/2010 | Burnett et al. |
| 2010/0191183 A1 | 7/2010 | Tanghoej et al. |

(56) References Cited

U.S. PATENT DOCUMENTS

| | | |
|---|---|---|
| 2010/0204682 A1 | 8/2010 | Tanghoj et al. |
| 2010/0241240 A1 | 9/2010 | Willard et al. |
| 2010/0261985 A1 | 10/2010 | Cohen-Solal et al. |
| 2010/0298857 A1 | 11/2010 | Zook et al. |
| 2010/0312163 A1 | 12/2010 | Forsell |
| 2011/0009799 A1 | 1/2011 | Mullick et al. |
| 2011/0009831 A1 | 1/2011 | Burkholz et al. |
| 2011/0015558 A1 | 1/2011 | Kaye et al. |
| 2011/0077605 A1 | 3/2011 | Karpowicz et al. |
| 2011/0089111 A1 | 4/2011 | Mori et al. |
| 2011/0098683 A1 | 4/2011 | Wiita et al. |
| 2011/0118537 A1 | 5/2011 | Wampler |
| 2011/0132838 A1 | 6/2011 | Curtis et al. |
| 2011/0208319 A1 | 8/2011 | Laster |
| 2011/0230950 A1 | 9/2011 | Knapp |
| 2011/0238163 A1 | 9/2011 | Andrews et al. |
| 2011/0269167 A1 | 11/2011 | Bene |
| 2011/0276024 A1 | 11/2011 | Randolph et al. |
| 2011/0282264 A1 | 11/2011 | Hurt |
| 2011/0301553 A1 | 12/2011 | Goral et al. |
| 2011/0301662 A1 | 12/2011 | Bar-Yoseph et al. |
| 2011/0320008 A1 | 12/2011 | Teague et al. |
| 2012/0029937 A1 | 2/2012 | Neftel et al. |
| 2012/0042427 A1 | 2/2012 | Messier |
| 2012/0053700 A1 | 3/2012 | Rickner |
| 2012/0078226 A1 | 3/2012 | Latere Dwan'isa et al. |
| 2012/0083899 A1 | 4/2012 | Whitmore, III |
| 2012/0107420 A1 | 5/2012 | Breit et al. |
| 2012/0136343 A1 | 5/2012 | Burnett |
| 2012/0154264 A1 | 6/2012 | Wang et al. |
| 2012/0165641 A1 | 6/2012 | Burnett et al. |
| 2012/0179144 A1 | 7/2012 | Carleo |
| 2012/0179145 A1 | 7/2012 | Nishtala et al. |
| 2012/0220926 A1 | 8/2012 | Soykan et al. |
| 2012/0238802 A1 | 9/2012 | Knight et al. |
| 2012/0265020 A1 | 10/2012 | Pandey et al. |
| 2012/0277155 A1 | 11/2012 | VanAntwerp et al. |
| 2012/0316656 A1 | 12/2012 | Deal et al. |
| 2013/0030262 A1 | 1/2013 | Burnett et al. |
| 2013/0066166 A1 | 3/2013 | Burnett et al. |
| 2013/0085468 A1 | 4/2013 | Buydenok |
| 2013/0090648 A1 | 4/2013 | Nagale et al. |
| 2013/0131621 A1 | 5/2013 | Van Holten et al. |
| 2013/0138077 A1 | 5/2013 | O'Day |
| 2013/0150828 A1 | 6/2013 | Conway |
| 2013/0172807 A1 | 7/2013 | Cruz |
| 2013/0172881 A1 | 7/2013 | Hill et al. |
| 2013/0184545 A1 | 7/2013 | Blomqvist et al. |
| 2013/0187563 A1 | 7/2013 | Sasai et al. |
| 2013/0197471 A1 | 8/2013 | Williams et al. |
| 2013/0199998 A1 | 8/2013 | Kelly et al. |
| 2013/0218135 A1 | 8/2013 | Dein |
| 2013/0231640 A1 | 9/2013 | Terry et al. |
| 2013/0231752 A1 | 9/2013 | Rosenbaum et al. |
| 2013/0253409 A1 | 9/2013 | Burnett |
| 2013/0267845 A1 | 10/2013 | Howle et al. |
| 2013/0274644 A1 | 10/2013 | Hertz |
| 2013/0274783 A1 | 10/2013 | Wynberg |
| 2013/0303865 A1 | 11/2013 | Rebec et al. |
| 2013/0303961 A1 | 11/2013 | Wolff et al. |
| 2013/0304082 A1 | 11/2013 | Aklog et al. |
| 2013/0317322 A1 | 11/2013 | Andrijauskas |
| 2013/0331824 A1 | 12/2013 | Kim |
| 2013/0338580 A1 | 12/2013 | Yamatani et al. |
| 2013/0345670 A1 | 12/2013 | Rajagopalan et al. |
| 2014/0031773 A1 | 1/2014 | Mikkaichi |
| 2014/0031787 A1 | 1/2014 | Burnes et al. |
| 2014/0039375 A1 | 2/2014 | Jimenez et al. |
| 2014/0058316 A1 | 2/2014 | Gupta et al. |
| 2014/0073926 A1 | 3/2014 | Rajendran et al. |
| 2014/0074144 A1 | 3/2014 | Shrivastava et al. |
| 2014/0135941 A1 | 5/2014 | Smouse et al. |
| 2014/0142539 A1 | 5/2014 | Salinas et al. |
| 2014/0148648 A1 | 5/2014 | Tycast et al. |
| 2014/0148754 A1 | 5/2014 | Soykan et al. |
| 2014/0155818 A1 | 6/2014 | Salinas et al. |
| 2014/0188248 A1 | 7/2014 | Gandhi |
| 2014/0188249 A1* | 7/2014 | Pendleton ............... A61F 2/95 623/23.66 |
| 2014/0214009 A1 | 7/2014 | Reyes |
| 2014/0228801 A1 | 8/2014 | Keeling |
| 2014/0275984 A1 | 9/2014 | Hermann et al. |
| 2014/0276341 A1 | 9/2014 | Ludin et al. |
| 2014/0276628 A1 | 9/2014 | Gandras et al. |
| 2014/0343515 A1 | 11/2014 | Sylvester et al. |
| 2014/0364820 A1 | 12/2014 | Solazzo et al. |
| 2015/0011855 A1 | 1/2015 | Burnett et al. |
| 2015/0011928 A1 | 1/2015 | Burnett |
| 2015/0017682 A1 | 1/2015 | Adam |
| 2015/0065783 A1* | 3/2015 | Buelna ............... A61B 18/04 606/41 |
| 2015/0080844 A1 | 3/2015 | Donovan et al. |
| 2015/0094548 A1 | 4/2015 | Sabatini et al. |
| 2015/0094644 A1 | 4/2015 | Lenihan et al. |
| 2015/0094696 A1 | 4/2015 | Adams, Jr. et al. |
| 2015/0100009 A1 | 4/2015 | Bearss |
| 2015/0134073 A1 | 5/2015 | Tang et al. |
| 2015/0164370 A1 | 6/2015 | Wabel et al. |
| 2015/0194052 A1 | 7/2015 | Sagan et al. |
| 2015/0223953 A1 | 8/2015 | Pendleton et al. |
| 2015/0224241 A1 | 8/2015 | Fontanazzi et al. |
| 2015/0273120 A1 | 10/2015 | Zamarripa et al. |
| 2015/0283362 A1 | 10/2015 | Shelton et al. |
| 2015/0290411 A1 | 10/2015 | Warrington et al. |
| 2015/0306364 A1 | 10/2015 | Shevgoor |
| 2015/0328027 A1 | 11/2015 | Nishio et al. |
| 2015/0352339 A1 | 12/2015 | Wang |
| 2016/0051176 A1 | 2/2016 | Ramos et al. |
| 2016/0058489 A1 | 3/2016 | Fischell et al. |
| 2016/0183819 A1 | 6/2016 | Burnett et al. |
| 2016/0213881 A9 | 7/2016 | Adams, Jr. et al. |
| 2016/0303303 A1 | 10/2016 | Rovatti et al. |
| 2016/0310711 A1 | 10/2016 | Luxon et al. |
| 2016/0331294 A1 | 11/2016 | Imran et al. |
| 2016/0367747 A1 | 12/2016 | Loske |
| 2017/0020724 A1 | 1/2017 | Burnett et al. |
| 2017/0021128 A1 | 1/2017 | Erbey, II et al. |
| 2017/0095323 A1 | 4/2017 | Garcia |
| 2017/0095641 A1 | 4/2017 | Scarpine et al. |
| 2017/0113000 A1 | 4/2017 | Tobescu et al. |
| 2017/0119519 A1 | 5/2017 | Sambusseti et al. |
| 2017/0128639 A1 | 5/2017 | Erbey, II et al. |
| 2017/0128654 A1 | 5/2017 | Feld |
| 2017/0136222 A1 | 5/2017 | Hakim et al. |
| 2017/0196576 A1 | 7/2017 | Long et al. |
| 2017/0197028 A1 | 7/2017 | Goldsmith |
| 2017/0232153 A1 | 8/2017 | Babu et al. |
| 2017/0266414 A1 | 9/2017 | Rocha-Singh et al. |
| 2017/0325927 A1 | 11/2017 | Gobel |
| 2017/0348507 A1 | 12/2017 | Erbey, II et al. |
| 2017/0348512 A1 | 12/2017 | Orr et al. |
| 2017/0367636 A1 | 12/2017 | Mantinband et al. |
| 2018/0001055 A1 | 1/2018 | Utas et al. |
| 2018/0116751 A1 | 5/2018 | Schwartz et al. |
| 2018/0117288 A1 | 5/2018 | Lindsay et al. |
| 2018/0147330 A1 | 5/2018 | Pend et al. |
| 2018/0169313 A1 | 6/2018 | Schwammenthal et al. |
| 2018/0177458 A1 | 6/2018 | Burnett |
| 2018/0193618 A1 | 7/2018 | Erbey, II et al. |
| 2018/0207412 A1 | 7/2018 | Malek et al. |
| 2018/0344250 A1 | 12/2018 | McKinney et al. |
| 2019/0030303 A1 | 1/2019 | Holman et al. |
| 2019/0091442 A1 | 3/2019 | Erbey, II et al. |
| 2019/0105465 A1 | 4/2019 | Erbey, II et al. |
| 2019/0201662 A1 | 7/2019 | Lad et al. |
| 2019/0240448 A1 | 8/2019 | Murdock |
| 2019/0247615 A1 | 8/2019 | Bishawi |
| 2020/0001045 A1 | 1/2020 | McIntyre |

(56) References Cited

U.S. PATENT DOCUMENTS

| | | | |
|---|---|---|---|
| 2020/0094017 A1 | 3/2020 | Erbey, II et al. | |
| 2021/0178133 A1 | 6/2021 | Walish et al. | |

FOREIGN PATENT DOCUMENTS

| | | | |
|---|---|---|---|
| CA | 2205473 C | 6/2006 | |
| CN | 2175619 Y | 8/1994 | |
| CN | 2562776 Y | 7/2003 | |
| CN | 2588940 Y | 12/2003 | |
| CN | 1479596 A | 3/2004 | |
| CN | 2753382 Y | 1/2006 | |
| CN | 2928043 Y | 8/2007 | |
| CN | 101224148 A | 7/2008 | |
| CN | 101426540 A | 5/2009 | |
| CN | 201814968 U | 5/2011 | |
| CN | 102176928 A | 9/2011 | |
| CN | 202459720 U | 10/2012 | |
| CN | 202526754 U | 11/2012 | |
| CN | 202802478 U | 3/2013 | |
| CN | 103096964 A | 5/2013 | |
| CN | 103203062 A | 7/2013 | |
| CN | 103841905 A | 6/2014 | |
| CN | 203777060 U | 8/2014 | |
| CN | 203842151 U | 9/2014 | |
| CN | 204158867 U | 2/2015 | |
| CN | 204246651 U | 4/2015 | |
| CN | 204446944 U | 7/2015 | |
| CN | 205126495 U | 4/2016 | |
| CN | 106237417 A | 12/2016 | |
| CN | 106473847 A | 3/2017 | |
| CN | 106693092 A | 5/2017 | |
| CN | 107261294 A | 10/2017 | |
| DE | 102012016049 A1 | 2/2014 | |
| EP | 873760 A1 | 10/1998 | |
| EP | 1011803 B1 | 9/2004 | |
| EP | 1980292 A2 | 10/2008 | |
| EP | 3488897 A1 | 5/2019 | |
| EP | 3970775 A1 | 3/2022 | |
| FR | 3052671 A1 * | 12/2017 | ........ A61M 25/0041 |
| FR | 3052671 A1 | 12/2017 | |
| JP | 59111748 A | 6/1984 | |
| JP | H42361 A | 1/1992 | |
| JP | H10504469 | 5/1998 | |
| JP | 2002510536 A | 4/2002 | |
| JP | 2002291879 A | 10/2002 | |
| JP | 200253888 | 11/2002 | |
| JP | 2002537893 A | 11/2002 | |
| JP | 2003530165 A | 10/2003 | |
| JP | 2004215787 A | 8/2004 | |
| JP | 2006516214 A | 6/2006 | |
| JP | 2006526464 A | 11/2006 | |
| JP | 2009505802 A | 2/2009 | |
| JP | 2009238520 A | 10/2009 | |
| JP | 2009537256 A | 10/2009 | |
| JP | 201005282 A | 1/2010 | |
| JP | 2010508984 A | 3/2010 | |
| JP | 2010119737 A | 6/2010 | |
| JP | 2010230618 A | 10/2010 | |
| JP | 2013149498 A | 1/2012 | |
| JP | 2012505022 A | 3/2012 | |
| JP | 2012530575 A | 12/2012 | |
| JP | 2014136116 A | 7/2014 | |
| JP | 2014176689 A | 9/2014 | |
| RU | 2113245 C1 | 6/1998 | |
| RU | 2300399 C1 | 6/2007 | |
| RU | 149161 U1 | 12/2014 | |
| TW | M540625 U | 5/2017 | |
| WO | 9529716 A1 | 11/1995 | |
| WO | 9716218 A1 | 5/1997 | |
| WO | 9816171 A1 | 4/1998 | |
| WO | 9850088 A1 | 11/1998 | |
| WO | 0054701 A1 | 9/2000 | |
| WO | 0160260 A1 | 8/2001 | |
| WO | 6558350 A1 | 12/2001 | |
| WO | 03017870 A1 | 3/2003 | |
| WO | 2004064681 A1 | 8/2004 | |
| WO | 2006017439 A2 | 2/2006 | |
| WO | 2006023589 A2 | 3/2006 | |
| WO | 2006044621 A2 | 4/2006 | |
| WO | 2007001978 A2 | 1/2007 | |
| WO | 2007027830 A1 | 3/2007 | |
| WO | 2008066625 A1 | 6/2008 | |
| WO | 2010082197 A2 | 7/2010 | |
| WO | 2011109570 A2 | 9/2011 | |
| WO | 2011139498 A1 | 11/2011 | |
| WO | 2013022005 A1 | 2/2013 | |
| WO | 2013029622 A1 | 3/2013 | |
| WO | 2014025367 A1 | 2/2014 | |
| WO | 2014043650 A2 | 3/2014 | |
| WO | 2014062225 A1 | 4/2014 | |
| WO | 2015105916 A1 | 7/2015 | |
| WO | 2015157467 A1 | 10/2015 | |
| WO | 2015198333 A1 | 12/2015 | |
| WO | 2016049654 A1 | 3/2016 | |
| WO | 2016103256 A1 | 6/2016 | |
| WO | 2017015345 A2 | 1/2017 | |
| WO | 2017015351 A2 | 1/2017 | |
| WO | 2017019974 A1 | 2/2017 | |
| WO | 2017087182 A1 | 5/2017 | |
| WO | 2018186781 A1 | 10/2018 | |
| WO | 2018200050 A1 | 11/2018 | |
| WO | 2019038730 A1 | 2/2019 | |
| WO | 2020236748 A1 | 11/2020 | |

OTHER PUBLICATIONS

Burr et al.; "Urinary catheter blockage depends on urine pH, calcium and rate of flow"; Spinal Cord; 1997; p. 521-525; vol. 35.

Clinical Practice Guidelines for Chronic Kidney Disease: Evaluation, Classification and Stratification; National Kidney Foundation; Am. J. Kidney Dis.; 2002; p. S1-S266; Suppl. 1.

"The Criteria Committee of the New York Heart Association", (1994), Nomenclature and Criteria for Diagnosis of Diseases of the Heart and Great Vessels, (9th ed.), Boston: Little, Brown & Co. p. 253-256 (Abstract).

Harris et al., "Relationship between patients' outcomes and the changes in serum creatinine and urine output and RIFLE classification in a large critical care cohort database", Kidney International, 2015, p. 369-377, vol. 88.

Jessup et al.; "The Cardiorenal Syndrome—Do We Need a Change of Strategy or a Change of Tactics?"; Journal of the American College of Cardiology; 2009; p. 597-599; vol. 53:7.

Mardis et al., "Comparative Evaluation of Materials Used for Internal Ureteral Stents", Journal of Endourology, 1993, pp. 105-115, vol. 7:2.

Mullens et al.; "Importance of Venous Congestion for Worsening of Renal Function in Advanced Decompensated Heart Failure"; Journal of the American College of Cardiology; 2009; p. 589-596; vol. 53:7.

Peters et al.; "Short and Long-Term Effects of the Angiotensin II Receptor Blocker Irbesartan on Intradialytic Central Hemodynamics: A Randomized Double-Blind Placebo-Controlled One-Year Intervention Trial (the Safir Study)"; PLoS ONE; Jun. 1, 2015; p. 1-22.

"Standard Specification for Ureteral Stents", ASTM International, 2014, Designation F1828-97, p. 1-6.

Verbrugge et al.; "The kidney in congestive heart failure: are natriuresis, sodium, and diuretics really the good, the bad and the ugly?"; European Journal of Heart Failure; 2014; p. 133-142; vol. 16.

Wolf, Jr. et al.; "Comparative Ureteral Microanatomy"; Journal of Endourology; 1996; p. 527-531; vol. 10:6.

Zelenko et al.; "Normal Ureter Size on Unenhanced Helical CT"; American Journal of Roentgenology; 2004; p. 1039-1041; vol. 182.

Johnson et al., "Clinical Practice Guidelines for Chronic Kidney Disease in Adults: Part I. Definition, Disease Stages, Evaluation, Treatment, and Risk Factors", American Family Physician, Sep. 1, 2004, p. 869-876, vol. 70 Issue 5.

(56) References Cited

OTHER PUBLICATIONS

Quadra-Coil | Olympus America | Medical, Ureteral Stents, https://www.medical.olympusamerica.com/products/quadra-coil (downloaded from the Internet Aug. 31, 2022) 2 pages.
Stents—Urology | Olympus America | Medical. Ureteral Stents, https://www.medical.olympusamerica.com/products/stents-Urology (downloaded from the Internet Aug. 31, 2022) 2 pages.
Ureteral stent—Quadra-Coil—Olympus Medical Europa, https://www.medicalexpo.com/prod/olympus-medical-europa/product-69587-661607.html (downloaded from the Internet Aug. 31, 2022) 5 pages.
U.S. Pat. No. 10,307,564 / U.S. Appl. No. 15/214,955, "Ureteral and Bladder Catheters and Methods of Inducing Negative Pressure to Increase Renal Perfusion", Jun. 4, 2019 / filed Jul. 20, 2016.
U.S. Pat. No. 9,744,331 / U.S. Appl. No. 15/215,081, "Ureteral and Bladder Catheters and Methods of Inducing Negative Pressure to Increase Renal Perfusion", Aug. 29, 2017 / filed Jul. 20, 2016.
U.S. Pat. No. 10,512,713 / U.S. Appl. No. 15/411,884, "Method of Removing Excess Fluid from a Patient with Hemodilution", Dec. 24, 2019 / filed Jan. 20, 2017.
U.S. Pat. No. 10/601,664 / U.S. Appl. No. 15/673,706, "Ureteral and Bladder Catheters and Methods of Inducing Negative Pressure to Increase Renal Perfusion", Apr. 7, 2020 / filed Aug. 10, 2017.
U.S. Pat. No. 10,765,834 / U.S. Appl. No. 15/687,064, "Ureteral and Bladder Catheters and Methods of Inducing Negative Pressure to Increase Renal Perfusion", Sep. 8, 2020 / filed Aug. 25, 2017.
U.S. Pat. No. 10,926,062 / U.S. Appl. No. 15/687,083, "Ureteral and Bladder Catheters and Methods of Inducing Negative Pressure to Increase Renal Perfusion", Feb. 23, 2021 / filed Aug. 25, 2017.
U.S. Appl. No. 15/879,976, "Ureteral and Bladder Catheters and Methods of Inducing Negative Pressure to Increase Renal Perfusion", filed Jan. 25, 2018.
U.S. Pat. No. 10,918,827 / U.S. Appl. No. 15/879,869, "Catheter Device and Method for Inducing Negative Pressure in a Patient's Bladder", Feb. 16, 2021 / filed Jan. 25, 2018.
U.S. Appl. No. 15/745,823, "Catheter Device and Method for Inducing Negative Pressure in a Patient's Bladder", filed Jul. 20, 2016.
U.S. Appl. No. 15/879,770, "Systems, Kits and Methods for Inducing Negative Pressure to Increase Renal Function", filed Jan. 25, 2018.
U.S. Pat. No. 10,918,825 / U.S. Appl. No. 16/012,233, "Ureteral and Bladder Catheters and Methods of Inducing Negative Pressure to Increase Renal Perfusion", Feb. 16, 2021 / filed Jun. 19, 2018.
U.S. Appl. No. 16/036,971, "Ureteral and Bladder Catheters and Methods of Inducing Negative Pressure to Increase Renal Perfusion", filed Jul. 17, 2018.
U.S. Appl. No. 16/206,207, "Percutaneous Ureteral Catheter", filed Nov. 30, 2018.
U.S. Appl. No. 16/206,389, "Coated Ureteral Catheter or Ureteral Stent and Method", filed Nov. 30, 2018.
U.S. Pat. No. 10,493,232 / U.S. Appl. No. 16/205,987, "Ureteral Catheters, Bladder Catheters, Systems, Kits and Methods for Inducing Negative Pressure to Increase Renal Function", Dec. 3, 2019 / filed Nov. 30, 2018.
U.S. Pat. No. 10,426,919 / U.S. Appl. No. 16/257,791, "Systems and Methods for Inducing Negative Pressure in a Portion of a Urinary Tract of a Patient", Oct. 1, 2019 filed Jan. 25, 2019.
U.S. Appl. No. 16/390,154, "Ureteral and Bladder Catheters and Methods of Inducing Negative Pressure to Increase Renal Perfusion", filed Apr. 22, 2019.
U.S. Appl. No. 16/542,680, "Systems and Methods for Inducing Negative Pressure in a Portion of a Urinary Tract of a Patient", filed Aug. 16, 2019.
U.S. Appl. No. 16/670,249, "Method of Removing Excess Fluids from a Patient with Hemodilution", filed Oct. 31, 2019.
U.S. Pat. No. 10,799,668 / U.S. Appl. No. 16/662,536, "Ureteral Catheters, Bladder Catheters, Systems, Kits and Methods for Inducing Negative Pressure to Increase Renal Function", Oct. 13, 2020 / filed Oct. 24, 2019.
U.S. Appl. No. 16/662,212, "Catheter and Method for Inducing Negative Pressure in a Patient's Bladder", filed Oct. 24, 2019.
U.S. Appl. No. 16/696,026, "Coated and/or Impregnated Ureteral Catheter or Stent and Method", filed Nov. 26, 2019.
U.S. Appl. No. 16/850,052, "Method of Removing Excess Fluid from a Patient with Venous Congestion", filed Apr. 16, 2020.
U.S. Appl. No. 16/820,781, "Ureteral and Bladder Catheters and Methods of Inducing Negative Pressure to Increase Renal Perfusion", filed Mar. 17, 2020.
U.S. Appl. No. 16/640,210, "Indwelling Pump for Facilitating Removal of Urine from the Urinary Tract", filed Aug. 24, 2018.
U.S. Appl. No. 16/817,773, "Ureteral and Bladder Catheters and Methods of Inducing Negative Pressure to Increase Renal Perfusion", filed Mar. 13, 2020.
U.S. Appl. No. 16/826,347, "Ureteral Catheters, Bladder Catheters, Systems, Kits and Methods for Inducing Negative Pressure to Increase Renal Function", filed Mar. 23, 2020.
U.S. Appl. No. 16/835,973, "Catheter Device and Method for Inducing Negative Pressure in a Patient's Bladder", filed Mar. 31, 2020.
U.S. Appl. No. 16/856,339, "Pump Assembly and System for Inducing Negative Pressure in a Portion of a Urinary Tract of a Patient", filed Apr. 23, 2020.
U.S. Appl. No. 16/872,965, "Ureteral and Bladder Catheters and Methods of Inducing Negative Pressure to Increase Renal Perfusion", filed May 12, 2020.
U.S. Appl. No. 17/077,793, "Ureteral and Bladder Catheters and Methods of Inducing Negative Pressure to Increase Renal Perfusion", filed Oct. 22, 2020.
U.S. Appl. No. 17/089,757, "Catheter Device and Method for Inducing Negative Pressure in a Patient's Bladder", filed Nov. 5, 2020.
U.S. Appl. No. 17/154,004, "Negative Pressure Therapy System", filed Jan. 20, 2021.
U.S. Appl. No. 17/152,636, "Systems, Kits and Methods for Inducing Negative Pressure to Increase Renal Function", filed Jan. 19, 2021.
Mordi et al., "Renal and Cardiovascular Effects of sodium-glucose cotransporter 2 (SGLT2) inhibition with loop Diuretics in diabetic patents with Chronic Heart Failure (REEDE-CHF): protocol for a randomised controlled double-blind cross-over trail". BJM open, 2017, vol. 7, pp. 1-9.
Damman et al., "Increased Central Venous Pressure Is Associated With Impaired Renal Function and Mortality in a Broad Spectrum of Patients With Cardiovascular Disease", 2009, Journal of the American College of Cardiology, vol. 53:7, pp. 582-588.
Dixon et al., "The musculature of the human renal calices, pelvis and upper ureter", J, Anat., 1982, vol. 135, pp. 129-137.
Gregersen et al., "Regional Differences Exist in Elastic Wall Properties in the Ureter", SJUN, 1996, vol. 30, pp. 343-348.
Kiil, "Urinary Flow and Ureteral Peristalsis" in: Lutzeyer W., Melchior H. (Eds.) Urodynamics, 1973, Springer, Berlin, Heidelberg (pp. 57-70).
Lala et al., "Relief and Recurrence of Congestion During and After Hospitalization for Acute Heart Failure: Insights from DOSE-AHF and CARRESS-HF", Circ Heart Fail, 2015, vol. 8:4, pp. 741-748.
Legrand et al. "Association between systemic hemodynamics and septic acute kidney injury in critically ill patients: a retrospective observational study", Critical Care, 2013, vol. 17:R278, pp. 1-8.
Nohria et al., "Cardiorenal Interactions Insights from the ESCAPE Trial", Heart Failure, 2008, vol. 51:13, pp. 1268-1274.
Uthoff et al., "Central venous pressure and impaired renal function in patients with acute heart failure", European Journal of Heart Failure, 2011. vol. 13, pp. 432-439.
Walker, "Annals of Surgery" 1913, Lippincott Williams & Wilkins, p. 58, Figures 3 and 9.
Webb, "Percutaneous Renal Surgery: A Practical Clinical Handbook", 2016, Springer International Publishing, Switzerland, p. 92.
Woodburne et al., "The Uretal Lumen during Peristalsis", Am. J. Anat., 1972. vol. 133, pp. 255-258.

* cited by examiner

URETERAL AND BLADDER CATHETERS AND METHODS OF INDUCING NEGATIVE PRESSURE TO INCREASE RENAL PERFUSION

CROSS REFERENCE TO RELATED APPLICATIONS

This application is a continuation of U.S. patent application Ser. No. 15/879,976 filed Jan. 25, 2018, which is a continuation-in-part of U.S. patent application Ser. No. 15/687,064 filed Aug. 25, 2017, now issued as U.S. Pat. No. 10,765,834, which is a continuation-in-part of U.S. patent application Ser. No. 15/411,884 filed Jan. 20, 2017, now issued as U.S. Pat. No. 10,512,713, which is a continuation-in-part of U.S. patent application Ser. No. 15/214,955 filed Jul. 20, 2016, now issued as U.S. Pat. No. 10,307,564, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in its entirety.

Also, U.S. patent application Ser. No. 15/879,976, filed Jan. 25, 2018, is a continuation-in-part of U.S. patent application Ser. No. 15/687,083 filed Aug. 25, 2017, which is a continuation-in-part of U.S. patent application Ser. No. 15/411,884 filed Jan. 20, 2017, now issued as U.S. Pat. No. 10,512,713, which is a continuation-in-part of U.S. patent application Ser. No. 15/214,955 filed Jul. 20, 2016, now issued as U.S. Pat. No. 10,307,564, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in its entirety.

Also, U.S. patent application Ser. No. 15/879,976 filed Jan. 25, 2018 is a continuation-in-part of U.S. patent application Ser. No. 15/745,823 filed Jan. 18, 2018, which is the U.S. national phase of PCT/US2016/043101, filed Jul. 20, 2016, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in its entirety.

Also, U.S. patent application Ser. No. 15/879,976 filed Jan. 25, 2018 claims the benefit of U.S. Provisional Application No. 62/489,789 filed Apr. 25, 2017 and U.S. Provisional Application No. 62/489,831 filed Apr. 25, 2017.

BACKGROUND

Technical Field

The present disclosure relates to methods and devices for treating impaired renal function across a variety of disease states and, in particular, to catheter devices, assemblies, and methods for collection of urine and/or inducement of negative pressure in the kidney(s), renal pelvis of the kidney(s), ureter(s), and/or bladder.

Background

The renal or urinary system includes a pair of kidneys, each kidney being connected by a ureter to the bladder, and a urethra for draining urine produced by the kidneys from the bladder. The kidneys perform several vital functions for the human body including, for example, filtering the blood to eliminate waste in the form of urine. The kidneys also regulate electrolytes (e.g., sodium, potassium and calcium) and metabolites, blood volume, blood pressure, blood pH, fluid volume, production of red blood cells, and bone metabolism. Adequate understanding of the anatomy and physiology of the kidneys is useful for understanding the impact that altered hemodynamics other fluid overload conditions have on their function.

In normal anatomy, the two kidneys are located retroperitoneally in the abdominal cavity. The kidneys are bean-shaped encapsulated organs. Urine is formed by nephrons, the functional unit of the kidney, and then flows through a system of converging tubules called collecting ducts. The collecting ducts join together to form minor calyces, then major calyces, which ultimately join near the concave portion of the kidney (renal pelvis). A major function of the renal pelvis is to direct urine flow to the ureter. Urine flows from the renal pelvis into the ureter, a tube-like structure that carries the urine from the kidneys into the bladder. The outer layer of the kidney is called the cortex, and is a rigid fibrous encapsulation. The interior of the kidney is called the medulla. The medulla structures are arranged in pyramids.

Each kidney is made up of approximately one million nephrons. Each nephron includes the glomerulus, Bowman's capsule, and tubules. The tubules include the proximal convoluted tubule, the loop of Henle, the distal convoluted tubule, and the collecting duct. The nephrons contained in the cortex layer of the kidney are distinct from the anatomy of those contained in the medulla. The principal difference is the length of the loop of Henle. Medullary nephrons contain a longer loop of Henle, which, under normal circumstances, allows greater regulation of water and sodium reabsorption than in the cortex nephrons.

The glomerulus is the beginning of the nephron, and is responsible for the initial filtration of blood. Afferent arterioles pass blood into the glomerular capillaries, where hydrostatic pressure pushes water and solutes into Bowman's capsule. Net filtration pressure is expressed as the hydrostatic pressure in the afferent arteriole minus the hydrostatic pressure in Bowman's space minus the osmotic pressure in the efferent arteriole.

Net Filtration Pressure=Hydrostatic Pressure (Afferent Arteriole)−Hydrostatic Pressure (Bowman's Space)−Osmotic Pressure (Efferent Arteriole)  (Equation 1)

The magnitude of this net filtration pressure defined by Equation 1 determines how much ultra-filtrate is formed in Bowman's space and delivered to the tubules. The remaining blood exits the glomerulus via the efferent arteriole. Normal glomerular filtration, or delivery of ultra-filtrate into the tubules, is about 90 ml/min/1.73 m$^2$.

The glomerulus has a three-layer filtration structure, which includes the vascular endothelium, a glomerular basement membrane, and podocytes. Normally, large proteins such as albumin and red blood cells, are not filtered into Bowman's space. However, elevated glomerular pressures and mesangial expansion create surface area changes on the basement membrane and larger fenestrations between the podocytes allowing larger proteins to pass into Bowman's space.

Ultra-filtrate collected in Bowman's space is delivered first to the proximal convoluted tubule. Re-absorption and secretion of water and solutes in the tubules is performed by a mix of active transport channels and passive pressure gradients. The proximal convoluted tubules normally reabsorb a majority of the sodium chloride and water, and nearly all glucose and amino acids that were filtered by the glomerulus. The loop of Henle has two components that are designed to concentrate wastes in the urine. The descending limb is highly water permeable and reabsorbs most of the remaining water. The ascending limb reabsorbs 25% of the remaining sodium chloride, creating a concentrated urine, for example, in terms of urea and creatinine. The distal convoluted tubule normally reabsorbs a small proportion of sodium chloride, and the osmotic gradient creates conditions for the water to follow.

Under normal conditions, there is a net filtration of approximately 14 mmHg. The impact of venous congestion can be a significant decrease in net filtration, down to approximately 4 mmHg. See Jessup M., *The cardiorenal syndrome: Do we need a change of strategy or a change of tactics?*, JACC 53(7):597-600, 2009 (hereinafter "Jessup"). The second filtration stage occurs at the proximal tubules. Most of the secretion and absorption from urine occurs in tubules in the medullary nephrons. Active transport of sodium from the tubule into the interstitial space initiates this process. However, the hydrostatic forces dominate the net exchange of solutes and water. Under normal circumstances, it is believed that 75% of the sodium is reabsorbed back into lymphatic or venous circulation. However, because the kidney is encapsulated, it is sensitive to changes in hydrostatic pressures from both venous and lymphatic congestion. During venous congestion the retention of sodium and water can exceed 85%, further perpetuating the renal congestion. See Verbrugge et al., *The kidney in congestive heart failure: Are natriuresis, sodium, and diuretics really the good, the bad and the ugly? European Journal of Heart Failure* 2014: 16,133-42 (hereinafter "Verbrugge").

Venous congestion can lead to a prerenal form of acute kidney injury (AKI). Prerenal AKI is due to a loss of perfusion (or loss of blood flow) through the kidney. Many clinicians focus on the lack of flow into the kidney due to shock. However, there is also evidence that a lack of blood flow out of the organ due to venous congestion can be a clinically important sustaining injury. See Damman K, *Importance of venous congestion for worsening renal function in advanced decompensated heart failure*, JACC 17:589-96, 2009 (hereinafter "Damman").

Prerenal AKI occurs across a wide variety of diagnoses requiring critical care admissions. The most prominent admissions are for sepsis and Acute Decompensated Heart Failure (ADHF). Additional admissions include cardiovascular surgery, general surgery, cirrhosis, trauma, burns, and pancreatitis. While there is wide clinical variability in the presentation of these disease states, a common denominator is an elevated central venous pressure. In the case of ADHF, the elevated central venous pressure caused by heart failure leads to pulmonary edema, and, subsequently, dyspnea in turn precipitating the admission. In the case of sepsis, the elevated central venous pressure is largely a result of aggressive fluid resuscitation. Whether the primary insult was low perfusion due to hypovolemia or sodium and fluid retention, the sustaining injury is the venous congestion resulting in inadequate perfusion.

Hypertension is another widely recognized state that creates perturbations within the active and passive transport systems of the kidney(s). Hypertension directly impacts afferent arteriole pressure and results in a proportional increase in net filtration pressure within the glomerulus. The increased filtration fraction also elevates the peritubular capillary pressure, which stimulates sodium and water re-absorption. See Verbrugge.

Because the kidney is an encapsulated organ, it is sensitive to pressure changes in the medullary pyramids. The elevated renal venous pressure creates congestion that leads to a rise in the interstitial pressures. The elevated interstitial pressures exert forces upon both the glomerulus and tubules. See Verbrugge. In the glomerulus, the elevated interstitial pressures directly oppose filtration. The increased pressures increase the interstitial fluid, thereby increasing the hydrostatic pressures in the interstitial fluid and peritubular capillaries in the medulla of the kidney. In both instances, hypoxia can ensue leading to cellular injury and further loss of perfusion. The net result is a further exacerbation of the sodium and water re-absorption creating a negative feedback. See Verbrugge, 133-42. Fluid overload, particularly in the abdominal cavity is associated with many diseases and conditions, including elevated intra-abdominal pressure, abdominal compartment syndrome, and acute renal failure. Fluid overload can be addressed through renal replacement therapy. See Peters, C. D., *Short and Long-Term Effects of the Angiotensin II Receptor Blocker Irbesartanon Intradialytic Central Hemodynamics: A Randomized Double-Blind Placebo-Controlled One-Year Intervention Trial (the SAFIR Study)*, PLoS ONE (2015) 10(6): e0126882. doi:10.1371/journal.pone.0126882 (hereinafter "Peters"). However, such a clinical strategy provides no improvement in renal function for patients with the cardiorenal syndrome. See Bart B, *Ultrafiltration in decompensated heart failure with cardiorenal syndrome*, NEJM 2012; 367:2296-2304 (hereinafter "Bart").

In view of such problematic effects of fluid retention, devices and methods for improving removal of urine from the urinary tract and, specifically for increasing quantity and quality of urine output from the kidneys, are needed.

SUMMARY

In some examples, a ureteral catheter for placement in a kidney, renal pelvis, and/or in a ureter adjacent to the renal pelvis of a patient is provided and comprises: an elongated tube comprising a proximal end, a distal end, and a sidewall extending between the proximal end and the distal end of the tube defining at least one drainage lumen extending through the tube; and an expandable retention portion configured to transition from a retracted position to a deployed position and which, in the deployed position, defines a three-dimensional shape positioned to maintain fluid flow from the kidney through at least the distal end of the tube.

In some examples, a method is provided for facilitating urine output from the kidney of a patient, comprising: (a) inserting a ureteral catheter into at least one of the patient's kidney, renal pelvis or in the ureter adjacent to the renal pelvis, wherein the catheter comprises: an elongated tube comprising a proximal end, a distal end, and a sidewall extending between the proximal end and the distal end of the tube defining at least one drainage lumen extending through the tube; and an expandable retention portion configured to be deployed from the distal end of the tube and, when deployed, defines a three-dimensional shape positioned to maintain fluid flow from the kidney through at least the distal end of the tube; (b) deploying the expandable retention portion in the patient's kidney, renal pelvis or in the ureter adjacent to the renal pelvis to maintain the distal end of the tube at a desired position in the kidney, renal pelvis or in the ureter adjacent to the renal pelvis of the patient; and (c)

applying negative pressure to the drainage lumen of the tube through a proximal portion thereof for a period of time to facilitate urine output from the kidney.

In some examples, a ureteral catheter is provided for placement in a kidney, renal pelvis and/or in a ureter adjacent to the renal pelvis of a patient, comprising: an elongated tube comprising a proximal end, a distal end, and a sidewall extending between the proximal end and the distal end of the tube defining at least one drainage lumen extending through the tube; and a expandable retention portion configured to transition from a retracted position to a deployed position and which, in the deployed position, is configured to maintain the distal end of the tube in the kidney, renal pelvis and/or in the ureter adjacent to the renal pelvis of the patient and to maintain fluid flow from the kidney through at least the distal end of the tube, wherein the expandable retention portion comprises at least one flexible member comprising: a first end positioned within a cylindrical space defined by an outer surface of the sidewall of the elongated tube and extending distally from the distal end of the tube along a central axis of the expandable retention portion; and a distal-most portion relative to the distal end of the elongated tube, which extends radially outwardly from the cylindrical space.

In some examples, a system is provided for inducing negative pressure in a portion of a urinary tract of a patient, the system comprising: at least one ureteral catheter comprising: an elongated tube comprising a proximal end, a distal end, and a sidewall extending between the proximal end and the distal end of the tube defining at least one drainage lumen extending through the tube; and an expandable retention portion configured to be deployed from the distal end of the tube and, when deployed, defines a three-dimensional shape positioned to maintain fluid flow from the kidney through at least the distal end of the tube; and a pump in fluid communication with the drainage lumen, the pump being configured for inducing a negative pressure in a portion of the urinary tract of the patient to draw fluid through the drainage lumen of the ureteral catheter.

Non-limiting examples of the present invention will now be described in the following numbered clauses:

Clause 1: A ureteral catheter for placement in a kidney, renal pelvis, and/or in a ureter adjacent to the renal pelvis of a patient, comprising: an elongated tube comprising a proximal end, a distal end, and a sidewall extending between the proximal end and the distal end of the tube defining at least one drainage lumen extending through the tube; and an expandable retention portion configured to transition from a retracted position to a deployed position and which, in the deployed position, defines a three-dimensional shape positioned to maintain fluid flow from the kidney through at least the distal end of the tube.

Clause 2: The ureteral catheter of clause 1, wherein, when deployed, the three-dimensional shape is positioned to maintain patency of fluid flow between the kidney and the proximal end of the tube such that at least a portion of the fluid flow flows through the expandable retention portion.

Clause 3: The ureteral catheter of clauses 1 or 2, wherein, when deployed, the expandable retention portion is configured to inhibit mucosal or uroendothelium tissue of the ureter or renal pelvis from occluding at least a portion of the expandable retention portion or distal end of the tube.

Clause 4: The ureteral catheter of any of clauses 1-3, wherein, when deployed, the expandable portion maintains patency of the distal end of the tube in at least one of the kidney, renal pelvis or in a ureter adjacent to the renal pelvis of a patient.

Clause 5: The ureteral catheter of any of clauses 1-4, wherein an area of two-dimensional slices of the three-dimensional shape defined by the deployed expandable retention portion in a plane transverse to a central axis of the expandable retention portion increases towards a distal end of the expandable retention portion.

Clause 6: The ureteral catheter of clause 5, wherein an area of a distal-most two dimensional slice of the three-dimensional shape is greater than a cross-sectional area of the distal end of the tube.

Clause 7: The ureteral catheter of any of clauses 1-6, wherein the elongated tube has an outer diameter of from about 0.33 mm to about 3.0 mm.

Clause 8: The ureteral catheter of any of clauses 1-7, wherein the elongated tube has an inner diameter of about 0.16 mm to about 2.40 mm.

Clause 9: The ureteral catheter of any of clauses 1-8, wherein a maximum cross sectional area of the three-dimensional shape defined by the deployed expandable retention portion in a plane transverse to a central axis of the expandable retention portion is up to about 350 $mm^2$.

Clause 10: The ureteral catheter of any of clauses 1-9, wherein a maximum cross sectional area of the three-dimensional shape defined by the deployed expandable retention portion in a plane transverse to a central axis of the expandable retention portion is from about 10 $mm^2$ to about 350 $mm^2$.

Clause 11: The ureteral catheter of any of clauses 1-10, wherein an axial length of the expandable portion from a proximal end to a distal end thereof is from about 5 mm to about 100 mm.

Clause 12: The ureteral catheter of any of clauses 1-11, wherein the central axis of the expandable retention portion is co-linear with a central axis of the tube.

Clause 13: The ureteral catheter of any of clauses 1-12, wherein the distal end of the tube is at least partially enclosed by the three-dimensional shape defined by the expandable retention portion.

Clause 14: The ureteral catheter of any of clauses 1-13, wherein the expandable retention portion comprises at least two elongated members extending from the distal end of the tube.

Clause 15: The ureteral catheter of clause 14, wherein at least one of the elongated members is biased to form structure sufficient to maintain a position and volume of the three-dimensional shape defined by the deployed expandable portion.

Clause 16: The ureteral catheter of clause 14, wherein at least one of the elongated member is biased to form a structure sufficient to maintain a position and volume of the three-dimensional shape defined by the deployed expandable portion when negative pressure is exposed to the ureter and/or kidney.

Clause 17: The ureteral catheter of any of clauses 1-16, wherein the expandable retention portion comprises a flexible material biased to a deployed position.

Clause 18: The ureteral catheter of clause 17, wherein the flexible material comprises a shape memory material.

Clause 19: The ureteral catheter of clauses 17 or 18, wherein the flexible material comprises one or more of nitinol, titanium, chromium, silicone, polyethylene, polyethylene terephthalate, polyurethane, and polyvinyl chloride.

Clause 20: The ureteral catheter of any of clauses 1-19, wherein the expandable retention portion is attached to a portion of an inner surface and/or an outer surface of the tube.

Clause 21: The ureteral catheter of any of clauses 1-20, wherein the expandable retention portion comprises at least two elongated members connected to a central portion, which extends through at least a portion of the at least one drainage lumen defined by the tube.

Clause 22: The ureteral catheter of any of clauses 1-21, wherein the expandable retention portion comprises at least one elongated member comprising a first end and a second end, each of which are at least partially enclosed within the drainage lumen defined by the tube, and a middle portion protruding from the distal end of the tube.

Clause 23: The ureteral catheter of any of clauses 1-22, wherein the expandable retention portion comprises at least one elongated member comprising at least a first bend in a first direction and a second bend in a second direction, wherein the second direction is not co-planer with the first direction.

Clause 24: The ureteral catheter of any of clauses 1-13 and 17-20, wherein the expandable retention portion comprises an elongated central member extending from the distal end of the tube and at least one flexible expandable disc having a central portion connected to the central member and a peripheral portion extending around the central member.

Clause 25: The ureteral catheter of clause 24, wherein the at least one disc has a diameter of from about 1.5 mm to about 25 mm.

Clause 26: The ureteral catheter of clauses 24 or 25, wherein the at least one disc comprises at least two struts and a circumferential ring, and wherein each of the at least two struts comprise a first end connected to the central member and a second end connected to the circumferential ring.

Clause 27: The ureteral catheter of any of clauses 24-26, wherein the at least one disc of the expandable portion comprises at least a first disc connected to the central member and a second disc connected to the central member at a position distal to the first member.

Clause 28: The ureteral catheter of clause 27, wherein a diameter of the second disc is greater than or equal to a diameter of the first disc.

Clause 29: The ureteral catheter of any of clauses 1-13 and 17-20, wherein the three-dimensional space defined by the expandable retention portion encloses at least a portion of the distal end of the elongated tube.

Clause 30: The ureteral catheter of clause 29, wherein the expandable retention portion comprises at least one annular member extending around the tube and at least one strut connecting the annular member to a portion of the tube.

Clause 31: The ureteral catheter of clause 30, wherein the at least one annular member comprises straight portions and curved portions arranged to form a circuitous pattern.

Clause 32: The ureteral catheter of clause 31, wherein the circuitous pattern comprises one or more of a zig-zig pattern, a sinusoidal pattern, a square-wave pattern, and any combination thereof.

Clause 33: The ureteral catheter of clause 29, wherein the expandable retention portion comprises: at least two annular members extending around the tube, the at least two annular members arranged such that portions of one of the annular members cross portions of the other annular member; and at least two struts connecting the annular members to the tube.

Clause 34: A method for facilitating urine output from the kidney of a patient, comprising: (a) inserting a ureteral catheter into at least one of the patient's kidney, renal pelvis or in the ureter adjacent to the renal pelvis, wherein the catheter comprises: an elongated tube comprising a proximal end, a distal end, and a sidewall extending between the proximal end and the distal end of the tube defining at least one drainage lumen extending through the tube; and an expandable retention portion configured to be deployed from the distal end of the tube and, when deployed, defines a three-dimensional shape positioned to maintain fluid flow from the kidney through at least the distal end of the tube; (b) deploying the expandable retention portion in the patient's kidney, renal pelvis or in the ureter adjacent to the renal pelvis to maintain the distal end of the tube at a desired position in the kidney, renal pelvis or in the ureter adjacent to the renal pelvis of the patient; and (c) applying negative pressure to the drainage lumen of the tube through a proximal portion thereof for a period of time to facilitate urine output from the kidney.

Clause 35: The method of clause 34, wherein the expandable retention portion is configured to inhibit mucosal or uroendothelium tissue of the ureter and/or renal pelvis from occluding at least the distal end of the tube.

Clause 36: The method of clauses 34 or 35, wherein the expandable retention portion comprises at least two elongated members extending from the distal end of the tube bent to form a structure sufficient to maintain a position and volume of the three-dimensional shape defined by the deployed expandable portion.

Clause 37: The method of any of clauses 34-36, wherein the expandable retention portion comprises a flexible material biased to the expanded position of the expandable retention portion.

Clause 38: The method of clause 37, wherein the flexible material comprises a shape memory material.

Clause 39: The method of any of clauses 34-38, wherein at least a portion of the expandable retention portion is mounted to an inner surface and/or an outer surface of the tube.

Clause 40: The method of any of clauses 34-39, wherein the expandable retention portion comprises a central member, which extends through at least a portion of the at least one drainage lumen, and at least two elongated members having a first end connected to a central member and a second end extending from the distal end of the tube.

Clause 41: The method of any of clauses 34-40, wherein a maximum cross sectional area of the three-dimensional shape defined by the deployed expandable retention portion in a plane transverse to a central axis of the expandable retention portion is from about 10 mm$^2$ to 350 mm$^2$.

Clause 42: A ureteral catheter for placement in a kidney, renal pelvis and/or in a ureter adjacent to the renal pelvis of a patient, comprising: an elongated tube comprising a proximal end, a distal end, and a sidewall extending between the proximal end and the distal end of the tube defining at least one drainage lumen extending through the tube; and an expandable retention portion configured to transition from a retracted position to a deployed position and which, in the deployed position, is configured to maintain the distal end of the tube in the kidney, renal pelvis and/or in the ureter adjacent to the renal pelvis of the patient and to maintain fluid flow from the kidney through at least the distal end of the tube, wherein the expandable retention portion comprises at least one flexible member comprising: a first end positioned within a cylindrical space defined by an outer surface of the sidewall of the elongated tube and extending distally from the distal end of the tube along a central axis of the expandable retention portion; and a distal-most portion relative to the distal end of the elongated tube, which extends radially outwardly from the cylindrical space.

Clause 43: The ureteral catheter of clause 40, wherein the expandable retention portion comprises at least two elongated flexible members, and wherein an area of a two-dimensional slice defined by the at least two flexible members in a plane transverse to a central axis of the expandable retention portion is greater than an area of a cross-section of the distal end of the elongated tube.

Clause 44: The ureteral catheter of clauses 42 or 43, wherein the expandable retention portion comprises a flexible material biased to the deployed position of the expandable retention portion.

Clause 45: The ureteral catheter of clause 44, wherein the flexible material comprises a shape memory material.

Clause 46: The ureteral catheter of any of clauses 42-45, wherein a cross-sectional area of the distal-most portion of the expandable retention portion is from about 10 mm$^2$ to 350 mm$^2$.

Clause 47: The ureteral catheter of any of clauses 42-46, wherein an axial length of the expandable portion from a proximal end to a distal end thereof is from about 5 mm to 100 mm.

Clause 48: The ureteral catheter of any of clauses 42-47, wherein the elongated tube has an outer diameter of from about 0.33 mm to 3.0 mm.

Clause 49: A system for inducing negative pressure in a portion of a urinary tract of a patient, the system comprising: at least one ureteral catheter comprising: an elongated tube comprising a proximal end, a distal end, and a sidewall extending between the proximal end and the distal end of the tube defining at least one drainage lumen extending through the tube; and an expandable retention portion configured to be deployed from the distal end of the tube and, when deployed, defines a three-dimensional shape positioned to maintain fluid flow from the kidney through at least the distal end of the tube; and a pump in fluid communication with the drainage lumen, the pump being configured for inducing a negative pressure in a portion of the urinary tract of the patient to draw fluid through the drainage lumen of the ureteral catheter.

Clause 50: The system of clause 49, wherein the expandable retention portion of the ureteral catheter is configured to inhibit mucosal or uroendothelium tissue of the ureter and/or renal pelvis from occluding at least the distal end of the tube.

Clause 51: The system of clauses 49 or 50, wherein, when deployed, the expandable portion maintains patency of the distal end of the tube in the kidney, renal pelvis and/or in a ureter adjacent to the renal pelvis of a patient.

Clause 52: The system of any of clauses 49-51, wherein the expandable retention portion of the ureteral catheter comprises at least two elongated flexible members, and wherein an area of a two-dimensional slice defined by the at least two flexible members in a plane transverse to a central axis of the expandable retention portion is greater than a cross-sectional area of the distal end of the elongated tube.

Clause 53: The system of any of clauses 49-52, wherein the expandable retention portion comprises a flexible material biased to the deployed position.

Clause 54: The system of clause 53, wherein the flexible material comprises a shape memory material.

Clause 55: The system of any of clauses 49-54, wherein the pump is configured to generate the position and/or negative pressure in a proximal end of the drainage lumen.

Clause 56: The system of any of clauses 49-55, wherein the pump applies a negative pressure of about 100 mmHg or less to a proximal end of the drainage lumen.

Clause 57: The system of any of clauses 49-56, wherein the pump is configured to operate at one of three pressure levels selected by a user, the pressure levels generating a negative pressure of 2 to 125 mmHg.

Clause 58: The system of any of clauses 49-57, wherein the pump is configured to alternate between generating negative pressure and generating positive pressure.

Clause 59: The system of any of clauses 49-58, wherein the pump has a sensitivity of about 10 mmHg or less.

Clause 60: The system of any of clauses 49-59, further comprising a bladder catheter placed in a bladder to maintain fluid flow from the bladder through the bladder catheter.

Clause 61: A catheter for placement in a bladder of a patient, comprising: an elongated tube comprising a proximal end, a distal end, and a sidewall extending between the proximal end and the distal end of the tube defining at least one drainage lumen extending through the tube; and an expandable retention portion configured to transition from a retracted position to a deployed position and which, in the deployed position, defines a three-dimensional shape positioned to maintain fluid flow from the bladder through at least a portion of an interior of the three-dimensional shape and through at least the distal end of the tube.

Clause 62: The catheter of clause 61, wherein, when deployed, the three-dimensional shape is positioned to maintain patency of fluid flow between the bladder and the proximal end of the tube such that at least a portion of the fluid flow flows through the expandable retention portion.

Clause 63: The catheter of clauses 61 or 62, wherein, when deployed, the expandable portion maintains patency of the distal end of the tube in the bladder of a patient.

Clause 64: The catheter of any of clauses 61-63, wherein an area of two-dimensional slices of the three-dimensional shape defined by the deployed expandable retention portion in a plane transverse to a central axis of the expandable retention portion increases towards a distal end of the expandable retention portion.

Clause 65: The catheter of clause 64, wherein an area of a distal-most two dimensional slice of the three-dimensional shape is greater than a cross-sectional area of the distal end of the tube.

Clause 66: The catheter of any of clauses 61-65, wherein a maximum cross sectional area of the three-dimensional shape defined by the deployed expandable retention portion in a plane transverse to a central axis of the expandable retention portion is up to about 1000 mm$^2$.

Clause 67: The catheter of any of clauses 61-66, wherein a maximum cross sectional area of the three-dimensional shape defined by the deployed expandable retention portion in a plane transverse to a central axis of the expandable retention portion is from about 100 mm$^2$ to about 1000 mm$^2$.

Clause 68: The catheter of any of clauses 61-67, wherein an axial length of the expandable portion from a proximal end to a distal end thereof is from about 5 mm to about 100 mm.

Clause 69: The catheter of any of clauses 61-68, wherein the central axis of the expandable retention portion is co-linear with a central axis of the tube.

Clause 70: The catheter of any of clauses 61-69, wherein the distal end of the tube is at least partially enclosed by the three-dimensional shape defined by the expandable retention portion.

Clause 71: The catheter of any of clauses 61-70, wherein the expandable retention portion comprises at least two elongated members extending from the distal end of the tube.

Clause 72: The catheter of clause 71, wherein at least one of the elongated members is biased to form structure sufficient to maintain a position and volume of the three-dimensional shape defined by the deployed expandable portion.

Clause 73: The catheter of clause 71, wherein at least one of the elongated member is biased to form a structure sufficient to maintain a position and volume of the three-dimensional shape defined by the deployed expandable portion when negative pressure is exposed to the bladder.

Clause 74: The catheter of any of clauses 61-73, wherein the expandable retention portion comprises a flexible material biased to a deployed position.

Clause 75: The catheter of clause 74, wherein the flexible material comprises a shape memory material.

Clause 76: The catheter of clauses 74 or 75, wherein the flexible material comprises one or more of nitinol, titanium, chromium, silicone, polyethylene, polyethylene terephthalate, polyurethane, and polyvinyl chloride.

Clause 77: The catheter of any of clauses 61-76, wherein the expandable retention portion is attached to a portion of an inner surface and/or an outer surface of the tube.

Clause 78: The catheter of any of clauses 61-77, wherein the expandable retention portion comprises at least two elongated members connected to a central portion, which extends through at least a portion of the at least one drainage lumen defined by the tube.

Clause 79: The catheter of any of clauses 61-78, wherein the expandable retention portion comprises at least one elongated member comprising a first end and a second end, each of which are at least partially enclosed within the drainage lumen defined by the tube, and a middle portion protruding from the distal end of the tube.

Clause 80: The catheter of any of clauses 61-79, wherein the expandable retention portion comprises at least one elongated member comprising at least a first bend in a first direction and a second bend in a second direction, wherein the second direction is not co-planer with the first direction.

Clause 81: The catheter of any of clauses 61-70 and 74-77, wherein the expandable retention portion comprises an elongated central member extending from the distal end of the tube and at least one flexible expandable disc having a central portion connected to the central member and a peripheral portion extending around the central member.

Clause 82: The catheter of clause 80, wherein the at least one disc has a diameter of from about 1.5 mm to about 25 mm Clause 83: The catheter of clauses 81 or 82, wherein the at least one disc comprises at least two struts and a circumferential ring, and wherein each of the at least two struts comprise a first end connected to the central member and a second end connected to the circumferential ring.

Clause 84: The catheter of any of clauses 81-84, wherein the at least one disc of the expandable portion comprises at least a first disc connected to the central member and a second disc connected to the central member at a position distal to the first member.

Clause 85: The catheter of clause 84, wherein a diameter of the second disc is greater than or equal to a diameter of the first disc.

Clause 86: The catheter of any of clauses 61-70 and 74-77, wherein the three-dimensional space defined by the expandable retention portion encloses at least a portion of the distal end of the elongated tube.

Clause 87: The catheter of clause 86, wherein the expandable retention portion comprises at least one annular member extending around the tube and at least one strut connecting the annular member to a portion of the tube.

Clause 88: The catheter of clause 87, wherein the at least one annular member comprises straight portions and curved portions arranged to form a circuitous pattern.

Clause 89: The catheter of claim 88, wherein the circuitous pattern comprises one or more of a zig-zig pattern, a sinusoidal pattern, a square-wave pattern, and any combination thereof.

Clause 90: The catheter of clause 86, wherein the expandable retention portion comprises: at least two annular members extending around the tube, the at least two annular members arranged such that portions of one of the annular members cross portions of the other annular member; and at least two struts connecting the annular members to the tube.

Clause 91: A method for facilitating urine output from the bladder of a patient, comprising: (a) inserting a catheter into at least one of the patient's bladder, wherein the catheter comprises: an elongated tube comprising a proximal end, a distal end, a sidewall extending between the proximal end and the distal end of the tube defining at least one drainage lumen extending through the tube, and at least one opening for urine to pass through the distal end and/or sidewall of the drainage lumen; and an expandable retention portion configured to be deployed from the distal end of the tube and, when deployed, defines a three-dimensional shape positioned to maintain fluid flow from the bladder through at least the distal end of the tube; (b) deploying the expandable retention portion in the patient's bladder to maintain the distal end of the tube at a desired position in the bladder of the patient; and (c) applying negative pressure to the drainage lumen of the tube through a proximal portion thereof for a period of time to facilitate urine output from the bladder.

Clause 92: The method of clause 91, wherein, when deployed, the three-dimensional shape is positioned to maintain patency of fluid flow between the bladder and the proximal end of the tube such that at least a portion of the fluid flow flows through the expandable retention portion.

Clause 93: The method of clauses 91 or 92, wherein the expandable retention portion comprises at least two elongated members extending from the distal end of the tube bent to form a structure sufficient to maintain a position and volume of the three-dimensional shape defined by the deployed expandable portion.

Clause 94: The method of any of clauses 91-93, wherein the expandable retention portion comprises a flexible material biased to the expanded position of the expandable retention portion.

Clause 95: The method of clause 94, wherein the flexible material comprises a shape memory material.

Clause 96: The method of any of clauses 91-95, wherein at least a portion of the expandable retention portion is mounted to an inner surface and/or an outer surface of the tube.

Clause 97: The method of any of clauses 91-96, wherein the expandable retention portion comprises a central member, which extends through at least a portion of the at least one drainage lumen, and at least two elongated members having a first end connected to a central member and a second end extending from the distal end of the tube.

Clause 98: The method of any of clauses 91-97, wherein a maximum cross sectional area of the three-dimensional shape defined by the deployed expandable retention portion in a plane transverse to a central axis of the expandable retention portion is from about 100 mm$^2$ to 1000 mm$^2$.

Clause 99: A catheter for placement in a bladder of a patient, comprising: an elongated tube comprising a proximal end, a distal end, and a sidewall extending between the proximal end and the distal end of the tube defining at least one drainage lumen extending through the tube; and an expandable retention portion configured to transition from a retracted position to a deployed position and which, in the deployed position, is configured to maintain the distal end of the tube in the bladder of the patient and to maintain fluid flow from the bladder through at least the distal end of the tube, wherein the expandable retention portion comprises at least one flexible member comprising: a first end positioned within a cylindrical space defined by an outer surface of the sidewall of the elongated tube and extending distally from the distal end of the tube along a central axis of the expandable retention portion; and a distal-most portion relative to the distal end of the elongated tube, which extends radially outwardly from the cylindrical space.

Clause 100: The catheter of clause 99, wherein the expandable retention portion comprises at least two elongated flexible members, and wherein an area of a two-dimensional slice defined by the at least two flexible members in a plane transverse to a central axis of the expandable retention portion is greater than an area of a cross-section of the distal end of the elongated tube.

Clause 101: The catheter of clauses 99 or 100, wherein the expandable retention portion comprises a flexible material biased to the deployed position of the expandable retention portion.

Clause 102: The catheter of clause 101, wherein the flexible material comprises a shape memory material.

Clause 103: The catheter of any of clauses 99-102, wherein a cross-sectional area of the distal-most portion of the expandable retention portion is from about 100 mm$^2$ to 1000 mm$^2$.

Clause 104: The catheter of any of clauses 99-103, wherein an axial length of the expandable retention portion from a proximal end to a distal end thereof is from about 5 mm to 100 mm.

Clause 105: A system for inducing negative pressure in a portion of a urinary tract of a patient, the system comprising: at least one catheter comprising: an elongated tube comprising a proximal end, a distal end, and a sidewall extending between the proximal end and the distal end of the tube defining at least one drainage lumen extending through the tube; and an expandable retention portion configured to be deployed from the distal end of the tube and, when deployed, defines a three-dimensional shape positioned to maintain fluid flow from the bladder through at least the distal end of the tube; and a pump in fluid communication with the drainage lumen, the pump being configured for inducing a negative pressure in a portion of the urinary tract of the patient to draw fluid through the drainage lumen of the catheter.

Clause 106: The system of clause 105, wherein, when deployed, the three-dimensional shape is positioned to maintain patency of fluid flow between the bladder and the proximal end of the tube such that at least a portion of the fluid flow flows through the expandable retention portion.

Clause 107: The system of clauses 105 or 106, wherein, when deployed, the expandable portion maintains patency of the distal end of the tube in the bladder of a patient.

Clause 108: The system of any of clauses 105-107, wherein the expandable retention portion of the catheter comprises at least two elongated flexible members, and wherein an area of a two-dimensional slice defined by the at least two flexible members in a plane transverse to a central axis of the expandable retention portion is greater than a cross-sectional area of the distal end of the elongated tube.

Clause 109: The system of any of clauses 104-107, wherein the expandable retention portion comprises a flexible material biased to the deployed position.

Clause 110: The system of clause 109, wherein the flexible material comprises a shape memory material.

Clause 111: The system of any of clauses 105-110, wherein the pump is configured to generate the position and/or negative pressure in a proximal end of the drainage lumen.

Clause 112: The system of any of clauses 105-111, wherein the pump applies a negative pressure of about 100 mmHg or less to a proximal end of the drainage lumen.

Clause 113: The system of any of clauses 105-112, wherein the pump is configured to operate at one of three pressure levels selected by a user, the pressure levels generating a negative pressure of 2 to 125 mmHg.

Clause 114: The system of any of clauses 105-113, wherein the pump is configured to alternate between generating negative pressure and generating positive pressure.

Clause 115: The system of any of clauses 105-114, wherein the pump has a sensitivity of about 10 mmHg or less.

Clause 116: The system of any of clauses 105-115, further comprising a ureteral catheter for placement into at least one of the patient's kidney, renal pelvis or in the ureter adjacent to the renal pelvis, wherein the ureteral catheter terminates in the bladder.

Clause 117: The system of clause 116, wherein the ureteral catheter comprises: an elongated tube comprising a proximal end, a distal end, and a sidewall extending between the proximal end and the distal end of the tube defining at least one drainage lumen extending through the tube; and an expandable retention portion configured to transition from a retracted position to a deployed position and which, in the deployed position, defines a three-dimensional shape positioned to maintain fluid flow from the kidney through at least the distal end of the tube.

Clause 118: The system of any of clauses 105-117, further comprising a ureteral stent for placement into at least one of the patient's kidney, renal pelvis or in the ureter adjacent to the renal pelvis, wherein the ureteral stent terminates in the bladder.

Clause 119: A method for removing fluid from the urinary tract of a patient, the method comprising: deploying a ureteral stent or ureteral catheter into a ureter of a patient to maintain patency of fluid flow between a kidney and a bladder of the patient; deploying a bladder catheter into the bladder of the patient, wherein the bladder catheter comprises a distal end configured to be positioned in a patient's bladder, a drainage lumen portion having a proximal end, and a sidewall extending therebetween; and applying negative pressure to the proximal end of the bladder catheter to induce negative pressure in a portion of the urinary tract of the patient to remove fluid from the urinary tract of the patient, wherein at least one of the ureteral catheter and bladder catheter comprise an elongated tube comprising a proximal end, a distal end, and a sidewall extending between the proximal end and the distal end of the tube defining at least one drainage lumen extending through the tube; and an expandable retention portion configured to transition from a retracted position to a deployed position and which, in the deployed position, defines a three-dimensional shape positioned to maintain fluid flow from the bladder through at least a portion of an interior of the three-dimensional shape and through at least the distal end of the tube.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended clauses with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION OF THE INVENTION

Figure 1:
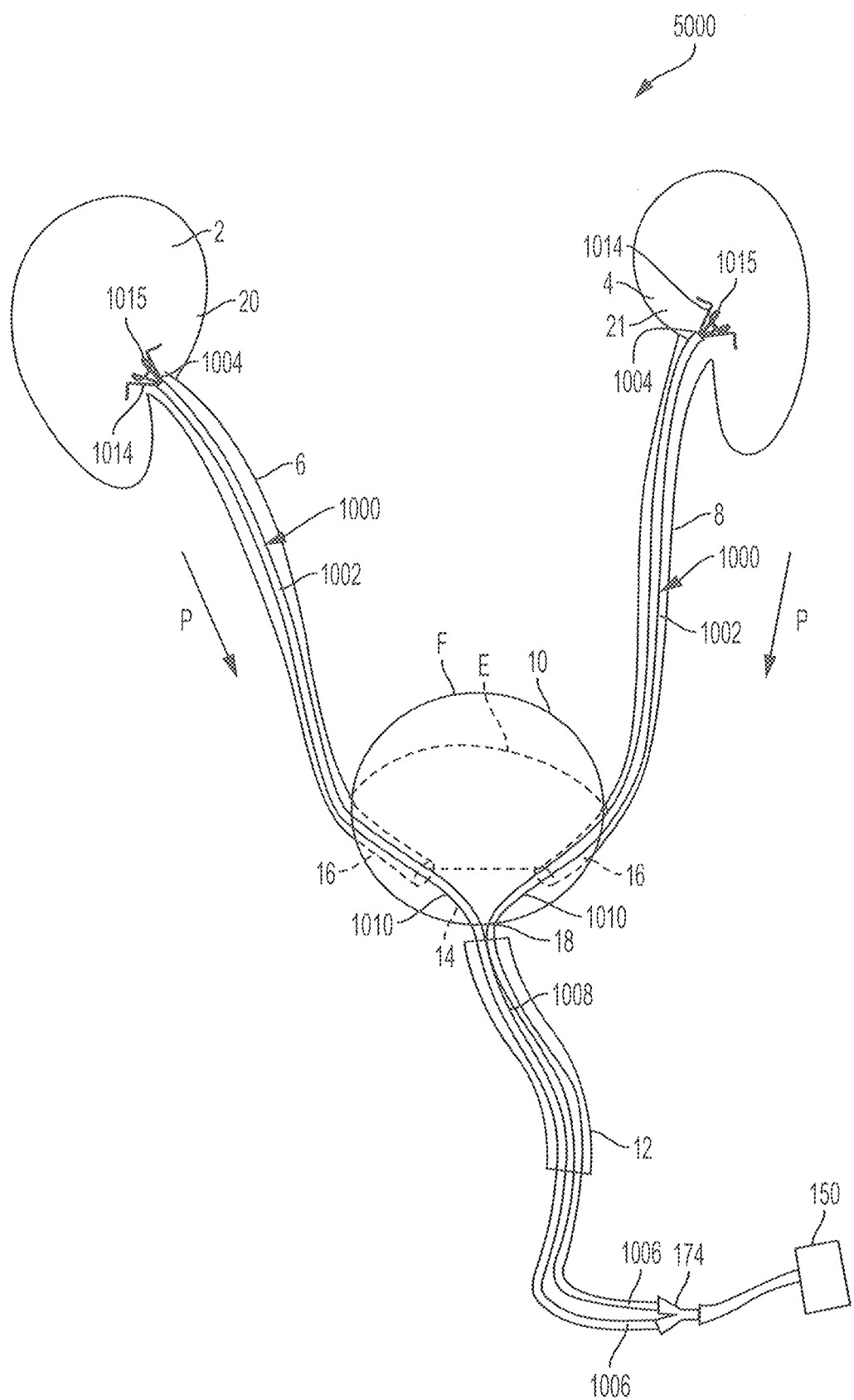
FIG. 1 is a schematic drawing of an indwelling portion of a urine collection assembly deployed in a urinary tract of a patient, according to an example of the present invention.

As used herein, the singular form of "a", "an", and "the" include plural referents unless the context clearly states otherwise.

As used herein, the terms "right", "left", "top", and derivatives thereof shall relate to the invention as it is oriented in the drawing figures. The term "proximal" refers to the portion of the catheter device that is manipulated or contacted by a user and/or to a portion of an indwelling catheter nearest to the urinary tract access site. The term "distal" refers to the opposite end of the catheter device that is configured to be inserted into a patient and/or to the portion of the device that is inserted farthest into the patient's urinary tract. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

As used herein, "maintain patency of fluid flow between a kidney and a bladder of the patient" means establishing, increasing or maintaining flow of fluid, such as urine, from the kidneys through the ureter(s), ureteral stent(s) and/or ureteral catheter(s) to the bladder. As used herein, "fluid" means urine and any other fluid from the urinary tract.

Fluid retention and venous congestion are central problems in the progression to advanced renal disease. Excess sodium ingestion coupled with relative decreases in excretion leads to isotonic volume expansion and secondary compartment involvement. In some examples, the present invention is generally directed to devices and methods for facilitating drainage of urine or waste from the bladder, ureter, and/or kidney(s) of a patient. In some examples, the present invention is generally directed to devices and methods for inducing a negative pressure in the bladder, ureter, and/or kidney(s) of a patient. While not intending to be bound by any theory, it is believed that applying a negative pressure to the bladder, ureter, and/or kidney(s) can offset the medullary nephron tubule re-absorption of sodium and water in some situations. Offsetting re-absorption of sodium and water can increase urine production, decrease total body sodium, and improve erythrocyte production. Since the intra-medullary pressures are driven by sodium and, therefore, volume overload, the targeted removal of excess sodium enables maintenance of volume loss. Removal of volume restores medullary hemostasis. Normal urine production is 1.48-1.96 L/day (or 1-1.4 ml/min).

Fluid retention and venous congestion are also central problems in the progression of prerenal Acute Kidney Injury (AKI). Specifically, AKI can be related to loss of perfusion or blood flow through the kidney(s). Accordingly, in some examples, the present invention facilitates improved renal hemodynamics and increases urine output for the purpose of relieving or reducing venous congestion. Further, it is anticipated that treatment and/or inhibition of AKI positively impacts and/or reduces the occurrence of other conditions, for example, reduction or inhibition of worsening renal function in patients with NYHA Class III and/or Class IV heart failure. Classification of different levels of heart failure are described in *The Criteria Committee of the New York Heart Association*, (1994), *Nomenclature and Criteria for Diagnosis of Diseases of the Heart and Great Vessels*, (9th ed.), Boston: Little, Brown & Co. pp. 253-256, the disclosure of which is incorporated by reference herein in its entirety. Reduction or inhibition of episodes of AKI and/or chronically decreased perfusion may also be a treatment for Stage 4 and/or Stage 5 chronic kidney disease. Chronic kidney disease progression is described in National Kidney Foundation, K/DOQI *Clinical Practice Guidelines for Chronic Kidney Disease: Evaluation, Classification and Stratification*. Am. J. Kidney Dis. 39:S1-S266, 2002 (Suppl. 1), the disclosure of which is incorporated by reference herein in its entirety.

With reference to FIG. 1, the urinary tract comprises a patient's right kidney 2 and left kidney 4. As discussed above, the kidneys 2, 4 are responsible for blood filtration and clearance of waste compounds from the body through urine. Urine produced by the right kidney 2 and the left kidney 4 is drained into a patient's bladder 10 through tubules, namely a right ureter 6 and a left ureter 8. For example, urine may be conducted through the ureters 6, 8 by peristalsis of the ureter walls, as well as by gravity. The ureters 6, 8 enter the bladder 10 through a ureter orifice or opening 16. The bladder 10 is a flexible and substantially hollow structure adapted to collect urine until the urine is excreted from the body. The bladder 10 is transitionable from an empty position (signified by reference line E) to a full position (signified by reference line F). Normally, when the bladder 10 reaches a substantially full state, urine is permitted to drain from the bladder 10 to a urethra 12 through a urethral sphincter or opening 18 located at a lower portion of the bladder 10. Contraction of the bladder 10 can be responsive to stresses and pressure exerted on a trigone region 14 of the bladder 10, which is the triangular region extending between the ureteral openings 16 and the urethral opening 18. The trigone region 14 is sensitive to stress and pressure, such that as the bladder 10 begins to fill, pressure on the trigone region 14 increases. When a threshold pressure on the trigone region 14 is exceeded, the bladder 10 begins to contract to expel collected urine through the urethra 12.

In some examples, a method is provided for facilitating urine output from the kidney, comprising: (a) inserting a catheter of the present invention as disclosed herein into at least one of a patient's kidney, renal pelvis or in the ureter adjacent to the renal pelvis; and (b) applying negative pressure to the proximal portion of the tube defining a drainage lumen of the catheter for a period of time to facilitate urine output from the kidney. Specific characteristics of exemplary ureteral catheters of the present invention are described in detail herein.

Delivering negative pressure into the kidney area of a patient has a number of anatomical challenges for at least three reasons. First, the urinary system is composed of highly pliable tissues that are easily deformed. Medical textbooks often depict the bladder as a thick muscular structure that can remain in a fixed shape regardless of the volume of urine contained within the bladder. However, in reality, the bladder is a soft deformable structure. The bladder shrinks to conform to the volume of urine contained in the bladder. An empty bladder more closely resembles a deflated latex balloon than a ball. In addition, the mucosal lining on the interior of the bladder is soft and susceptible to irritation and damage. It is desirable to avoid drawing the urinary system tissue into the orifices of the catheter to maintain adequate fluid flow therethrough and avoid injury to the surrounding tissue.

Second, the ureters are small tube-like structures that can expand and contract to transport urine from the renal pelvis to the bladder. This transport occurs in two ways: peristaltic activity and by a pressure gradient in an open system. In the peristaltic activity, a urine portion is pushed ahead of a contractile wave, which almost completely obliterates the lumen. The wave pattern initiates in the renal pelvis area, propagates along the ureter, and terminates in the bladder. Such a complete occlusion interrupts the fluid flow and can prevent negative pressure delivered in the bladder from reaching the renal pelvis without assistance. The second type of transport, by pressure gradient through a wide-open ureter, may be present during large urine flow. The pressure head in the renal pelvis is not caused by contraction of the smooth muscles of the upper urinary tract, but rather is generated by the flow of urine, and therefore reflects arterial blood pressure. Kiil F., "Urinary Flow and Ureteral Peristalsis" in: Lutzeyer W., Melchior H. (eds) Urodynamics. Springer, Berlin, Heidelberg (pp. 57-70) (1973).

Third, the renal pelvis is at least as pliable as the bladder. The thin wall of the renal pelvis can expand to accommodate multiple times the normal volume, for example as occurs in patients having hydronephrosis.

While not intending to be bound by any theory, it is believed that the tissues of the renal pelvis and bladder may be flexible enough to be drawn inwardly during delivery of negative pressure to somewhat conform to the shape and volume of the tool being used to deliver negative pressure. As such, a three dimensional shape that maintains a three dimensional void volume that can transmit the negative pressure to at least one calyx is believed to be helpful to delivery negative pressure to the nephrons. In addition, given the flexibility of the tissues, the protection of these tissues from the openings that lead to the lumen of the tool is desirable. The catheters discussed herein can be useful for delivering negative pressure, positive pressure, or can be used at ambient pressure, or any combination thereof.

Exemplary Ureteral Catheters:

Referring to FIG. 1, a urine collection assembly 5000 includes an exemplary ureteral catheter 1000 that comprises: an elongated tube 1002 for draining fluid such as urine from at least one of a patient's kidney 2, 4, renal pelvis 20, 21 or in the ureter 6, 8 adjacent to the renal pelvis 20, 21. The elongated tube 1002 comprises: a distal end 1004 configured to be positioned in a patient's kidney 2, 4, renal pelvis 20, 21 and/or in the ureter 6, 8 adjacent to the renal pelvis 20, 21; a proximal end 1006 through which fluid 1008 is drained to the bladder 10 or outside of the body of the patient (e.g., a portion of the tube 1002 extending from the urethra 12 to an external fluid collection container and/or a pump); and a sidewall 1010 extending between the proximal end 1006 and the distal end 1004 of the tube 1002 defining at least one drainage lumen (see reference L of FIG. 5) formed from the tube 1002 extending through the tube 1002.

The tube 1002 can have any suitable length to accommodate anatomical differences for gender and/or patient size. In some examples, the tube 1002 has a length from about 30 cm to about 120 cm. Further, the elongated tube 1002 can have an outer diameter of from about 0.33 mm to about 3.0 mm. The elongated tube 1002 can also have an inner diameter of about 0.16 mm to about 2.40 mm. It is appreciated that the outer and inner diameters of the elongated tube 1002 can include any of the subranges of the previously described ranges.

The tube 1002 can be formed from any suitable flexible and/or deformable material. Such materials facilitate advancing and/or positioning the tube 1002 in the bladder 10 and ureters 6, 8. Non-limiting examples of such materials include biocompatible polymers, polyvinyl chloride, polytetrafluoroethylene (PTFE) such as Teflon®, silicon coated latex, or silicon. At least a portion or all of the catheter device 1000, particularly the tube 1002, can be coated with a hydrophilic coating to facilitate insertion and/or removal and/or to enhance comfort. In some examples, the coating is a hydrophobic and/or lubricious coating. For example, suitable coatings can comprise ComfortCoat® hydrophilic coating which is available from Koninklijke DSM N.V. or hydrophilic coatings comprising polyelectrolyte(s) such as are disclosed in U.S. Pat. No. 8,512,795, which is incorporated herein by reference. In some examples, the tube 1002 is impregnated with or formed from a material viewable by fluoroscopic imaging. For example, the biocompatible polymer which forms the tube 1002 can be impregnated with barium sulfate or a similar radiopaque material. As such, the structure and position of the tube 1002 is visible to fluoroscopy.

The proximal end 1006 of the tube 1002 is essentially free of or free of openings. While not intending to be bound by any theory, it is believed that when negative pressure is applied at the proximal end 1006 of the tube 1002, that openings in the proximal portion of the tube 1002 may be undesirable as such openings may diminish the negative pressure at the distal portion 1014 of the ureteral catheter 1000 and thereby diminish the draw or flow of fluid or urine from the kidney 2, 4, and renal pelvis 20, 21 of the kidney 2, 4. It is desirable that the flow of fluid from the ureter 6, 8 and/or kidney 2, 4 is not prevented by occlusion of the ureter 6, 8 and/or kidney 2, 4 by the catheter 1000. Also, while not intending to be bound by any theory, it is believed that when negative pressure is applied at the proximal end 1006, ureter 6, 8 tissue may be drawn against or into openings along the proximal end 1006 of the tube 1002, which may irritate the tissues.

Referring to FIG. 1, a distal portion 1014 of the ureteral catheter 1000 further comprises a retention portion 1015 for maintaining the distal portion 1014 of the tube 1002 and drainage lumen in the ureter 6, 8 and/or kidney 2, 4. The retention portion 1015 is expandable to permit positioning of the retention portion 1015 in the ureter 6, 8, renal pelvis 20, 21, and/or kidney 2, 4. For example, the retention portion 1015 is desirably sufficiently expandable to absorb forces exerted on the catheter 1000 and to prevent such forces from being translated to the ureters 6, 8. Further, if the retention portion 1015 is pulled in the proximal direction (reference P in FIG. 1) toward the patient's bladder 10, the retention portion 1015 is sufficiently flexible to begin to unwind, straighten or collapse so that it can be drawn in the lumen of the tube 1002 and, optionally, through the ureter 6, 8.

Figure 2A:
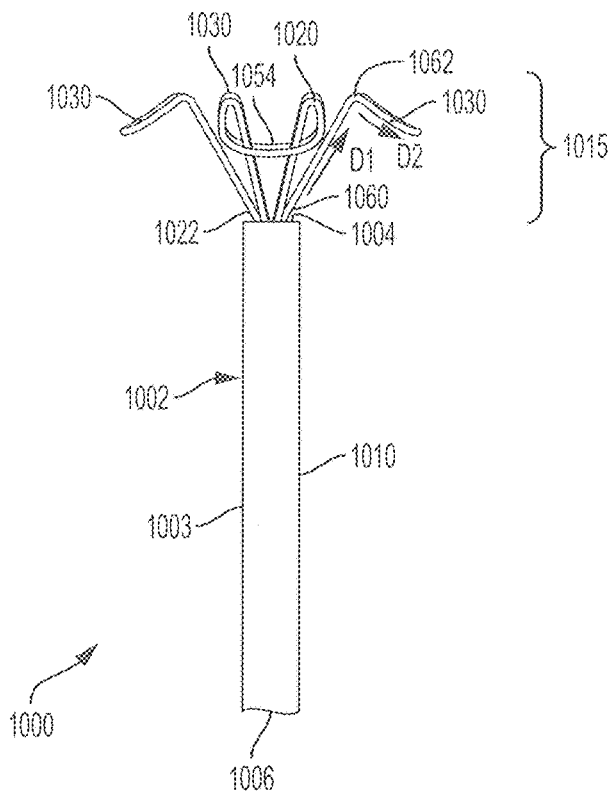
FIG. 2A is a front view of a ureteral catheter having a deployed retention portion according to an example of the present invention.
Figure 2B:
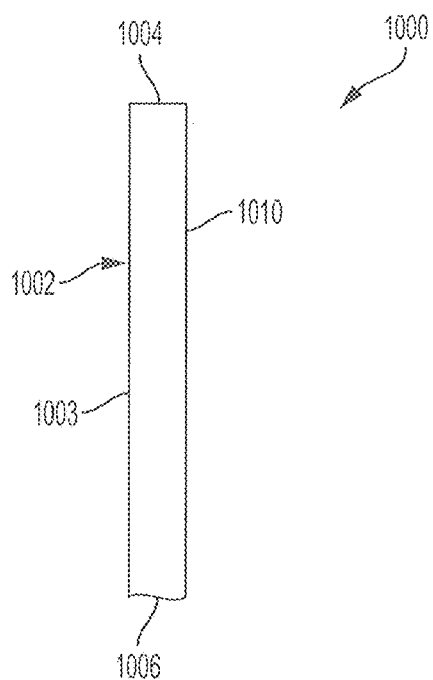
FIG. 2B is a front view of the ureteral catheter shown in FIG. 2A but having a retracted retention portion according to an example of the present invention.
Figure 3A:
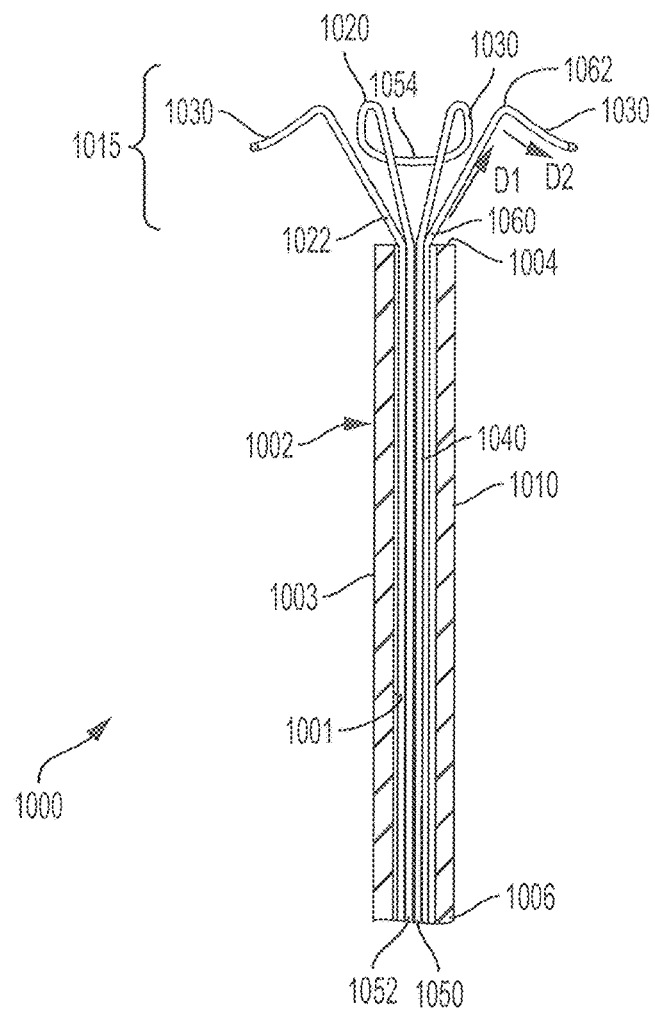
FIG. 3A is a front cross-sectional view of a ureteral catheter having a deployed retention portion according to an example of the present invention.
Figure 3B:
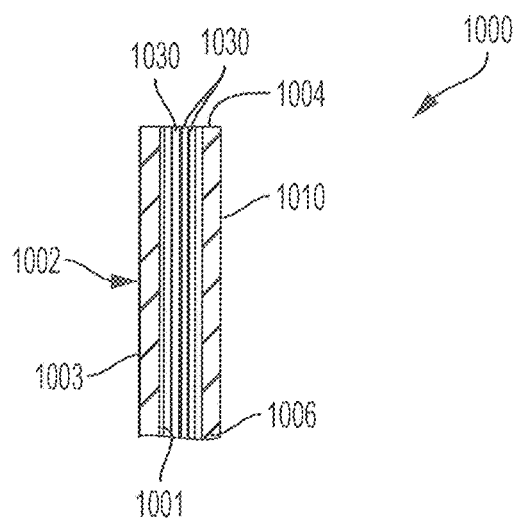
FIG. 3B is a front cross-sectional view of the ureteral catheter shown in FIG. 3A but having a retracted retention portion according to an example of the present invention.

As such, referring to FIGS. 2A-3B for example, the retention portion 1015 is configured to transition from a retracted position (FIGS. 2B and 3) to a deployed position (FIGS. 2A and 3). In the deployed position, the retention portion 1015 defines a three-dimensional shape positioned to maintain fluid flow from the kidney 2, 4 through at least the distal end 1004 of the tube 1002.

In some examples, the retention portion 1015 comprises a three-dimensional shape that is positioned to maintain patency of fluid flow between the kidney 2, 4 and the proximal end 1006 of the tube 1002 such that at least a portion of the fluid flows through the expandable retention portion 1015. For instance, when deployed, the expandable retention portion 1015 can be configured to inhibit mucosal or uroendothelium tissue of the ureter 6, 8 or renal pelvis 20, 21 from occluding at least a portion of the expandable retention portion 1015 or distal end 1004 of the tube 1002. In addition, in some examples, the expandable retention portion 1015 maintains patency of the distal end 1004 of the tube 1002 in at least one of the kidney 2, 4, renal pelvis 20, 21 or in a ureter 6, 8 adjacent to the renal pelvis 20, 21 of a patient.

The three-dimensional shape defined by the deployed expandable retention portion 1015 can be configured to occupy a particular area. For example, and as shown in FIGS. 2A and 3A for example, an area of two-dimensional slices of the three-dimensional shape defined by the deployed expandable retention portion 1015 in a plane transverse to a central axis of the expandable retention portion 1015 increases towards a distal end 1020 of the expandable retention portion 1015. The "central axis" of the expandable retention portion 1015 refers to a straight and/or curved axis extending through the expandable retention portion 1015 in an axial or longitudinal direction.

The area of the distal-most end 1020 two dimensional slice of the three-dimensional shape can also be greater than a cross-sectional area of the distal end 1004 of the tube 1002. In some examples, the maximum cross sectional area of the three-dimensional shape defined by the deployed expandable retention portion 1015 in a plane transverse to a central axis of the expandable retention portion 1015 is up to about 350 mm$^2$. In certain examples, the maximum cross sectional area of the three-dimensional shape defined by the deployed expandable retention portion 1015 in a plane transverse to a central axis of the expandable retention portion 1015 is from about 10 mm$^2$ to about 350 mm$^2$.

With respect to the length of the retention portion 1015, an axial length of the expandable retention portion 1015 from a proximal end 1022 to a distal end 1020 thereof can be from about 5 mm to about 100 mm. As further shown in FIGS. 2A-8B, the central axis of the expandable retention portion 1015 can be co-linear with a central axis of the tube 1002. In some examples, the distal end 1004 of the tube 1002 is at least partially enclosed by the three-dimensional shape defined by the expandable retention portion 1015.

In some examples, the expandable retention portion 1015 is attached to a portion of the tube 1002. For instance, referring to FIG. 3A, the expandable retention portion 1015 can be attached to a portion of the inner surface 1001 of the tube 1002, the outer surface 1003 of the tube 1002, or both.

The retention portion 1015 can be formed from a flexible material biased to a deployed position of the retention portion 1015. As such, the material of the retention portion 1015 automatically deploys the retention portion 1015 when the retention portion 1015 is extended from the tube 1002. In some examples, the flexible material comprises a shape memory material. As used herein, a "shape memory material" refers to a material that is capable of returning to its original shape without the use of an external stimulus. Non-limiting examples of flexible materials that can be used to form the retention portion 1015 include nitinol, titanium, chromium, silicone, polyethylene, polyethylene terephthalate, polyurethane, polyvinyl chloride, and any combination thereof.

In some examples, as shown in FIGS. 2A and 3A, the expandable retention portion 1015 comprises at least two, such as at least three or at least four, elongated members 1030 extending from the distal end 1004 of the tube 1002. As shown in FIG. 3A, the elongated members 1030 can extend through at least a portion of the lumen formed through the interior of the tube 1002 and out from the distal end 1004 of the tube 1002. Further, at least one of the elongated members 1030 is biased to form a structure sufficient to maintain a position and volume of the three-dimensional shape defined by the deployed expandable retention portion 1015. For example, at least one of the elongated members 1030 can be biased to form a structure sufficient to maintain a position and volume of the three-dimensional shape defined by the deployed expandable retention portion 1015 when negative pressure is exposed to the ureter 6, 8 and/or kidney 2, 4.

Figure 4:
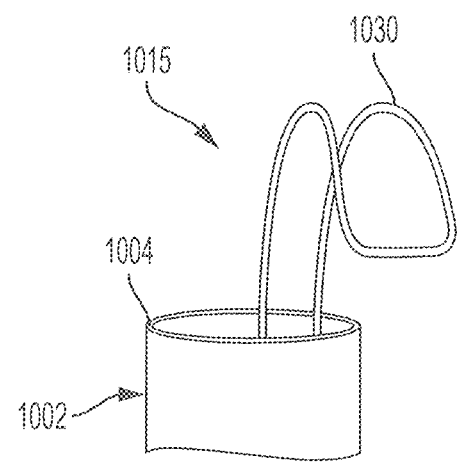
FIG. 4 is an exploded perspective view of a distal end of an elongated tube of a ureteral catheter having a deployed retention portion according to an example of the present invention.

FIG. 4 further illustrates an expanded view of an elongated member 1030 extending from the distal end 1004 of the tube 1002. As shown in FIG. 4, the elongated member 1030 is biased to form a structure sufficient to maintain a position and volume of the three-dimensional shape defined by the deployed expandable retention portion 1015.

In some examples, referring to FIG. 3A, at least two, such as at least three or at least four, of the elongated members 1030 are connected to a central portion 1040, such as a central member in some examples, which extends through at least a portion of the at least one drainage lumen defined by the tube 1002 and, optionally, from the distal end 1004 of the tube 1002. The elongated members 1030 can be connected at or to the central portion 1040 using various materials and techniques known in the art for connecting materials that form the elongated members 1030.

In some examples, referring again to FIG. 3A, the expandable retention portion 1015 comprises at least one elongated member 1030 having a first end 1050 and a second end 1052 that can be enclosed within the drainage lumen defined by the tube 1002. As further shown in FIGS. 2A, 3A, and 5, a middle portion 1054 protrudes from the distal end 1004 of the tube 1002. It is appreciated that the middle portion 1054 is biased to form structure sufficient to maintain a position and volume of the three-dimensional shape defined by the deployed expandable retention portion 1015.

The previously described elongated members 1030 can have various shapes that are configured to maintain a position and volume of the three-dimensional shape defined by the deployed expandable retention portion 1015. For example, and as shown in FIGS. 2A and 3A, at least one elongated members 1030 can comprise at least a first bend 1060 in a first direction "D1" and a second bend 1062 in a second direction "D2". In some examples, the second direction "D2" is not co-planer with the first direction "D1".

Figure 5:
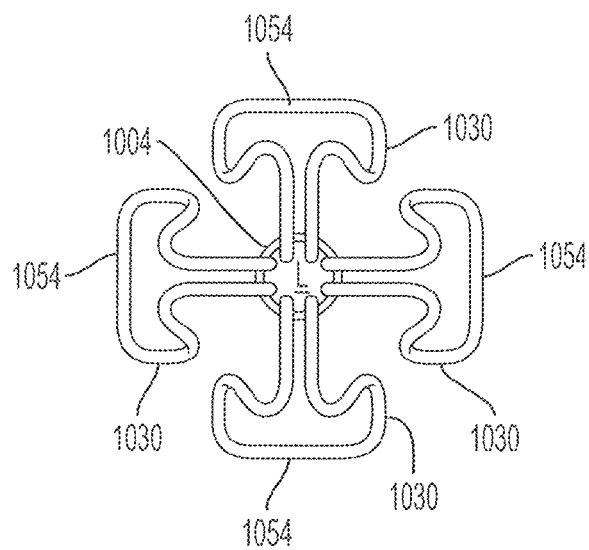
FIG. 5 is top view of the ureteral catheter shown in FIG. 2A according to an example of the present invention.

As previously described, the retention portion 1015 can be retracted into the lumen of the elongated tube 1002. As such, the elongated members 1030 previously described can be retracted into the lumen of the elongated tube 1002. FIGS. 2B and 3B illustrate elongated members 1030 that are retracted and drawn into the lumen of the elongated tube 1002. Further, FIG. 5 illustrates the lumen (reference L) formed from the tube 1002.

The retention portion 1015 can also comprise different configurations. In some examples, referring to FIGS. 6 and 7, the portion 1015 comprises an elongated central member 1070 extending from the distal end 1004 of the tube 1002 and at least one flexible expandable disc 1072 having a central portion 1074 connected to the central member 1070 and a peripheral portion 1076 extending around the central member 1070.

In some examples, the retention portion 1015 comprises more than one flexible expandable disc 1072, such as at least two or at least three flexible expandable discs 1072. For instance, the retention portion 1015 can comprise at least a first flexible expandable disc 1072 connected to the central member 1070 and a second flexible expandable disc 1080 connected to the central member 1070 at a position distal to the first disc 1072. It is appreciated that the retention portion 1015 can include additional flexible expandable discs 1072 that are proximal or distal to the first and/or second flexible expandable disc 1072, 1080 such as, for example, a third flexible expandable disc 1082.

Figure 6:
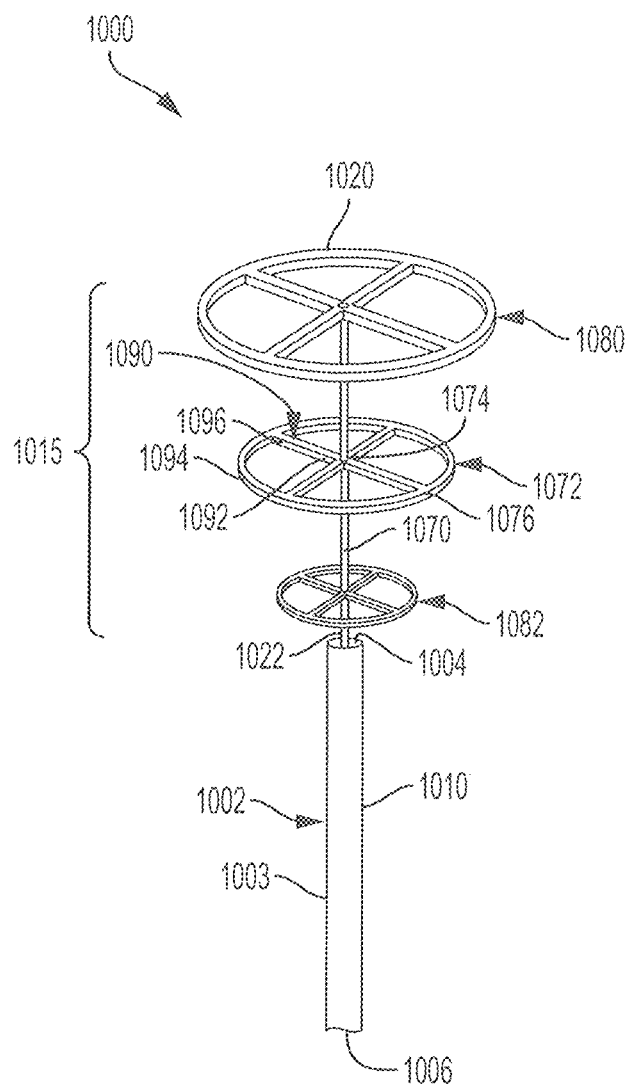
FIG. 6 is a perspective view of a ureteral catheter having a deployed retention portion according to another example of the present invention.
Figure 7:
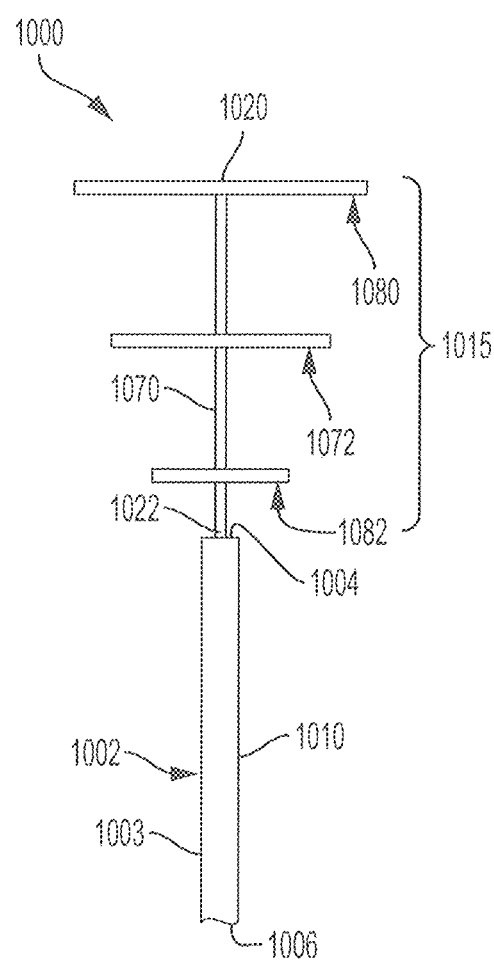
FIG. 7 is a front view of the ureteral catheter shown in FIG. 6.
Figure 8A:
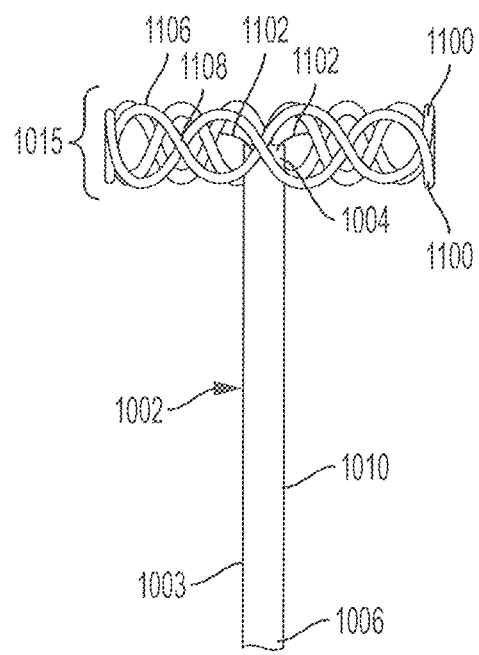
FIG. 8A is a front view of a ureteral catheter having a deployed retention portion according to yet another example of the present invention.
Figure 8B:
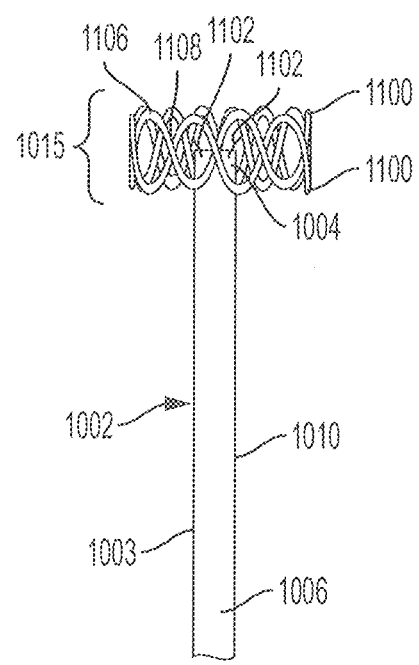
FIG. 8B is a front view of the ureteral catheter shown in FIG. 8A but having a collapsed retention portion according to an example of the present invention.

Further, each disc 1072, such as discs 1072, 1080, 1082 shown in FIGS. 6 and 7, can have a diameter of from about 1.5 mm to about 25 mm. Further, the various discs 1072, 1080, 1082 can have the same or different diameter. For example, the diameter of the second disc 1080 can be greater than or equal to a diameter of the first disc 1072, and the diameter of the first disc 1080 can be greater than or equal to a diameter of the third disc 1082. In some examples, as shown in FIGS. 6 and 7, the diameter of the discs 1072, 1080, 1082 increase from the proximal end 1022 to the distal end 1020 of the retention portion 1015.

In some examples, referring to FIGS. 6 and 7, the flexible expandable discs 1072, 1080, 1082 can comprise at least two struts 1090, such as at least three struts 1090 or at least four struts 1090, and a circumferential ring 1094 formed by the peripheral portion 1076. Each strut 1090 can comprise a first end 1092 connected to the central member 1070 and a second end 1096 connected to the circumferential ring 1094. When the retention member 1015 comprises multiple discs 1072, 1080, 1082, one or more including all of the discs 1072, 1080, 1082 can independently comprise at least two struts 1090 and a circumferential ring 1094 as previously described.

The retention portion 1015 comprising the at least one flexible expandable disc 1072 can be retracted into the lumen of the elongated tube 1002. As such, the flexible expandable discs 1072, 1080, 1082 previously described can be retracted into the lumen of the elongated tube 1002.

As previously described, the distal end 1004 of the tube 1002 can be at least partially enclosed by the three-dimensional shape defined by the expandable retention portion 1015. In some examples, referring to FIGS. 8A and 8B, the retention portion 1015 comprises at least one annular member 1100 extending around the tube 1002 and at least one strut 1102 connecting the annular member 1100 to a portion of the tube 1002 such that the at least one annular member 1100 extending around the tube 1002 at least partially encloses the distal end 1004 of the tube 1002. The at least one annular member 1100 can comprise straight portions 1106 and curved portions 1108 arranged to form a circuitous pattern. In some examples, the circuitous pattern comprises one or more of a zig-zig pattern, a sinusoidal pattern, a square-wave pattern, or any combination thereof.

Referring again to FIGS. 8A and 8B, the expandable retention portion 1015 can comprise at least two annular members 1100 extending around the tube 1002. The at least two annular members 1100 can be arranged such that portions of one of the annular members 1100 cross portions of the other annular member 1100. Further, at least two struts 1102 can connect the annular members 1100 to the tube 1002.

The retention portion 1015 comprising the annular member(s) 1100 can be retracted into the elongated tube 1002. As such, the annular member(s) 1100 previously described can be retracted into the lumen of the elongated tube 1002.

As indicated, the previously described ureteral catheters 1000 can be placed in a kidney 2, 4, renal pelvis 20, 21, and/or in a ureter 6, 8 adjacent to the renal pelvis of a patient. In some examples, the ureteral catheter 1000 comprising a retention member 1015 can be deployed into a patient's urinary tract and more specifically in the renal pelvis 20, 21 region/kidney 2, 4 using a conduit through the urethra 12 and into the bladder 10. Further, if the retention portion 1015 is pulled in the proximal direction P toward the patient's bladder 10, the retention portion 1015 can be sufficiently flexible to begin to collapse so that it can be drawn through the ureter 6, 8. To deploy the ureteral catheter 1000, the medical professional would insert a cystoscope into the urethra 12 to provide a channel for tools to enter the bladder 10. The ureteral orifice would be visualized and guide wire would be inserted through the cystoscope and ureter until the tip of the guide wire reaches the renal pelvis 20, 21. The cystoscope likely would be removed, and a "pusher tube" would be fed over the guide wire up to the renal pelvis 20, 21. The guidewire would be removed while the "pusher tube" stays in place to act as deployment sheath. The ureteral catheter 1000 would be inserted through the pusher tube/sheath and the catheter tip would be actuated once it extends beyond the end of the pusher tube/sheath. The retention member 1015 would expand radially to assume the deployed position.

Systems for Inducing Negative Pressure

Figure 9:
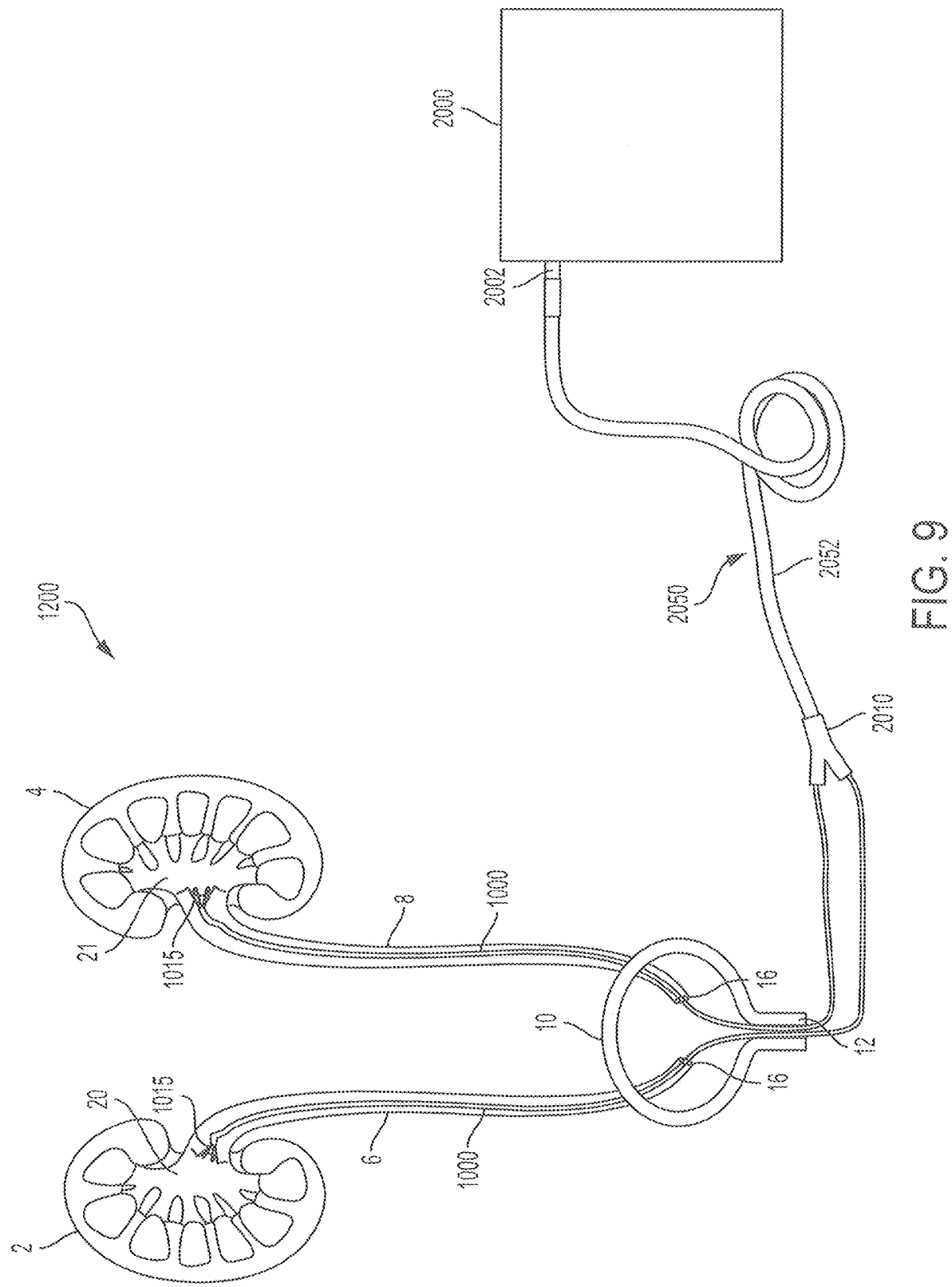
FIG. 9 is a schematic drawing of another example of an indwelling portion of a urine collection assembly deployed in a urinary tract of a patient, according to an example of the present invention.

With reference to FIG. 9, an exemplary system 1200 for inducing negative pressure in a urinary tract of a patient for increasing renal perfusion is illustrated. The system 1200 comprises one or two ureteral catheters 1000 connected to a fluid pump 2000 for generating the negative pressure. More specifically, the patient's urinary tract comprises the patient's right kidney 2 and left kidney 4. The kidneys 2, 4 are responsible for blood filtration and clearance of waste compounds from the body through urine. Urine produced by the right kidney 2 and the left kidney 4 is drained into a patient's bladder 10 through tubules, namely a right ureter 6 and a left ureter 8, which are connected to the kidneys at the renal pelvis 20, 21. Urine may be conducted through the ureters 6, 8 by peristalsis of the ureter walls, as well as by gravity. The ureters 6, 8 enter the bladder 10 through a ureter orifice or opening 16. The bladder 10 is a flexible and substantially hollow structure adapted to collect urine until the urine is excreted from the body.

Referring to FIG. 1, the bladder 10 is transitionable from an empty position (signified by reference line E) to a full position (signified by reference line F). Normally, when the bladder 10 reaches a substantially full state, urine is permitted to drain from the bladder 10 to a urethra 12 through a urethral sphincter or opening 18 located at a lower portion of the bladder 10. Contraction of the bladder 10 can be responsive to stresses and pressure exerted on a trigone region 14 of the bladder 10, which is the triangular region extending between the ureteral openings 16 and the urethral opening 18. The trigone region 14 is sensitive to stress and pressure, such that as the bladder 10 begins to fill, pressure on the trigone region 14 increases. When a threshold pressure on the trigone region 14 is exceeded, the bladder 10 begins to contract to expel collected urine through the urethra 12.

Figure 10:
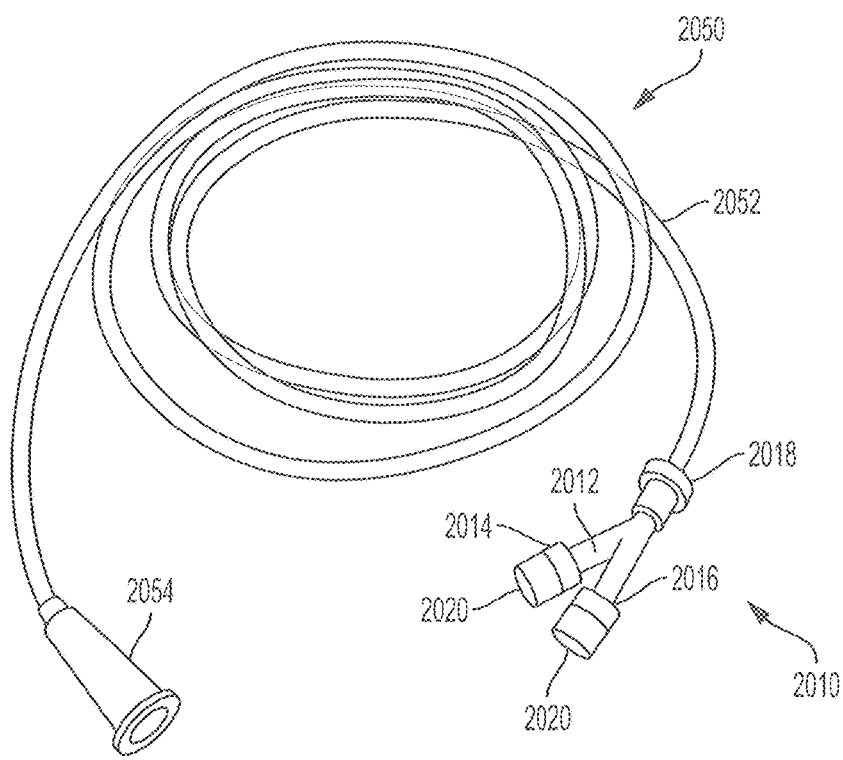
FIG. 10 is a perspective view of a tubing assembly and y-connector for connecting a ureteral catheter to a fluid pump according to an example of the disclosure.
Figure 11:
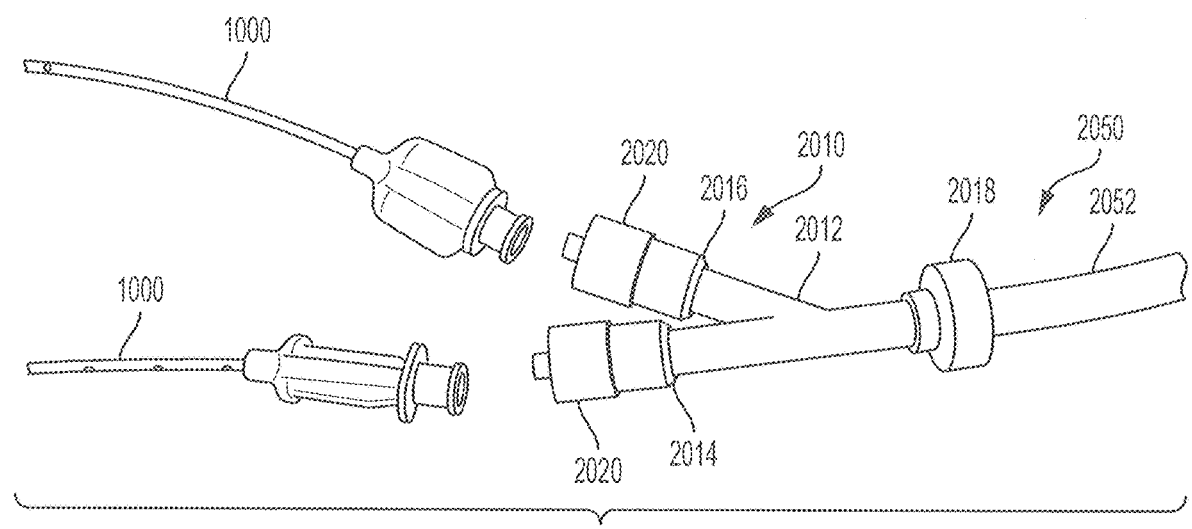
FIG. 11 is a perspective view of ureteral catheters being connected to the y-connector of FIG. 10 according to an example of the present disclosure.

As shown in FIG. 9, distal portions of the ureteral catheter(s) 1000 are deployed in the renal pelvis 20, 21 near the kidneys 2, 4. Proximal portions of one or more of the catheter(s) 1000 are connected to a single outflow port 2002 of a fluid pump 2000 through a y-connector 2010 and tubing set 2050. An exemplary y-connector 2010 and tubing set 2050 connected thereto are shown in FIGS. 10 and 11. Referring to FIGS. 10 and 11, the y-connector 2010 comprises a tubular body 2012 formed from a rigid plastic material, the body 2012 comprising two inflow ports 2014, 2016 and a single outflow port comprising a one-way check valve 2018 to prevent backflow. The inflow ports 2014, 2016 can comprise a connector portion 2020, such as a luer lock connector, screw connector, or similar mechanism as is known in the art for receiving the proximal end of the catheters 1000. The proximal ends of catheters 1000 have a corresponding structure for mounting to the y-connector 2010. The tubing set 2050 comprises a length of flexible medical tubing 2052 extending between the one-way check valve 2018 of the y-connector 2010 and a funnel-shaped connector 2054 configured to engage the outflow port 2002 of a fluid pump 2000 as shown in FIG. 9. The shape and size of the funnel-shaped connector 2054 can be selected based on the type of pump 2000 being used. In some examples, the funnel-shaped connector 2054 can be manufactured with a distinctive configuration so that it can only be connected to a particular pump type, which is deemed to be safe for inducing negative pressure in a patient's bladder, ureter, or kidneys. In other examples, as described herein, the connector 2054 can be a more generic configuration adapted for attachment to a variety of different types of fluid pumps.

In some examples, the pump 2000 applies a negative pressure of about 100 mmHg or less to a proximal end of the drainage lumen. The pump 2000 can also be configured to operate at one of three pressure levels selected by a user in which the pressure levels generate a negative pressure of 2 mmHg to 125 mmHg for example. Further, in some examples, the pump 2000 is configured to alternate between generating negative pressure and generating positive pressure. In some examples, the pump 2000 also has a sensitivity of about 10 mmHg or less.

System 1200 is but one example of a negative pressure system for inducing negative pressure that can be used with the ureteral catheters 1000 disclosed herein. Other systems and urine collection assemblies which can be used with catheters 1000. In addition, catheter(s) 1000 can be connected to separate sources of negative pressure. In other examples, one or more catheter(s) 1000 can be connected to a negative pressure source, while other caterer(s) 1000 can be connected to an unpressurized fluid collection container.
Exemplary Urine Collection Assemblies:

As previously described, and as shown in FIG. 1, a urine collection assembly 5000 including ureteral catheters 1000 is configured to be positioned within the urinary tract of a patient. For example, distal ends 1014 of the ureteral catheters 1000 can be configured to be deployed in the patient's ureters 2, 4 and, in particular, in a renal pelvis 20, 21 area of the kidneys 6, 8.

In some examples, the urine collection assembly 5000 can comprise two separate ureteral catheters 1000, such as a first catheter 1000 disposed in or adjacent to the renal pelvis 20 of the right kidney 2 and a second catheter 1000 disposed in or adjacent to the renal pelvis 21 of the left kidney 4. The catheters 1000 can be separate for their entire lengths, or can be held in proximity to one another by a clip, ring, clamp, or other type of connection mechanism (e.g., connector 150) to facilitate placement or removal of the catheters 1000. In some examples, catheters 1000 can merge or be connected together to form a single drainage lumen. In other examples, the catheters 1000 can be inserted through or enclosed within another catheter, tube, or sheath along portions or segments thereof to facilitate insertion and retraction of the catheters 1000 from the body. For example, a bladder catheter can be inserted over and/or along the same guidewire as the ureteral catheters 1000, thereby causing the ureteral catheters 1000 to extend from the distal end of the bladder catheter. In some examples, when a separate bladder catheter is used, the ureteral catheter 1000 terminates in the bladder 10.

In some examples, and as previously described, the ureteral catheter 1000 can comprise: an elongated tube 1002 for draining fluid such as urine from at least one of a patient's kidney 2, 4, renal pelvis 20, 21 or in the ureter 6, 8 adjacent to the renal pelvis 20, 21. The elongated tube 1002 comprises: a distal end 1004 configured to be positioned in a patient's kidney 2, 4, renal pelvis 20, 21 and/or in the ureter 6, 8 adjacent to the renal pelvis 20, 21; a proximal end 1006 through which fluid 1008 is drained to the bladder 10 or outside of the body of the patient (e.g., a portion of the tube 1002 extending from the urethra 12 to an external fluid collection container and/or pump 2000); and a sidewall 1010 extending between the proximal end 1006 and the distal end 1004 of the tube 1002 defining at least one drainage lumen extending through the tube 1002. In some examples, the tube 1002 terminates in another indwelling catheter and/or drainage lumen, such as in a drainage lumen of the bladder catheter. In that case, fluid drains from the proximal end of the ureteral catheter 1002 and is directed from the body through the additional indwelling catheter and/or drainage lumen.

As indicated, the ureteral catheters 1000 can be connected to the bladder catheter to provide a single drainage lumen for urine, or the ureteral catheter(s) 1000 can drain via separate tube(s) from the bladder catheter. The bladder catheter can comprise a deployable seal and/or anchor for anchoring, retaining, and/or providing passive fixation for indwelling portions of the urine collection assembly 5000 and, in some examples, to prevent premature and/or untended removal of assembly components during use. The anchor is configured to be located adjacent to the lower wall of the patient's bladder 10 to prevent patient motion and/or forces applied to indwelling catheters 1000 from translating to the ureters. The bladder catheter comprises an interior of which defines a drainage lumen configured to conduct urine from the bladder 10 to an external urine collection container.

In some examples, the bladder catheter size can range from about 8 Fr to about 24 Fr. In some examples, the bladder catheter can have an external diameter ranging from about 2.7 to about 8 mm. In some examples, the bladder catheter can have an internal diameter ranging from about 2.16 to about 6.2 mm. The bladder catheter can be available in different lengths to accommodate anatomical differences for gender and/or patient size. For example, the average female urethra length is only a few inches, so the length of a tube can be rather short. The average urethra length for males is longer due to the penis and can be variable. It is possible that woman can use bladder catheters with longer length tubes provided that the excess tubing does not increase difficulty in manipulating and/or preventing contamination of sterile portions of the catheter. In some examples, a sterile and indwelling portion of the bladder catheter can range from about 1 inch to 3 inches (for women) to about 20 inches for men. The total length of the bladder catheter including sterile and non-sterile portions can be from one to several feet.

Exemplary bladder catheters and urine collection assemblies that can be used with the ureteral catheters 1000 of the present invention are described in paragraphs [0394] to [0414] and the corresponding figures of U.S. Publication No. 2017/0348507, which is incorporated by reference herein.

Bladder Catheter

Figure 21:
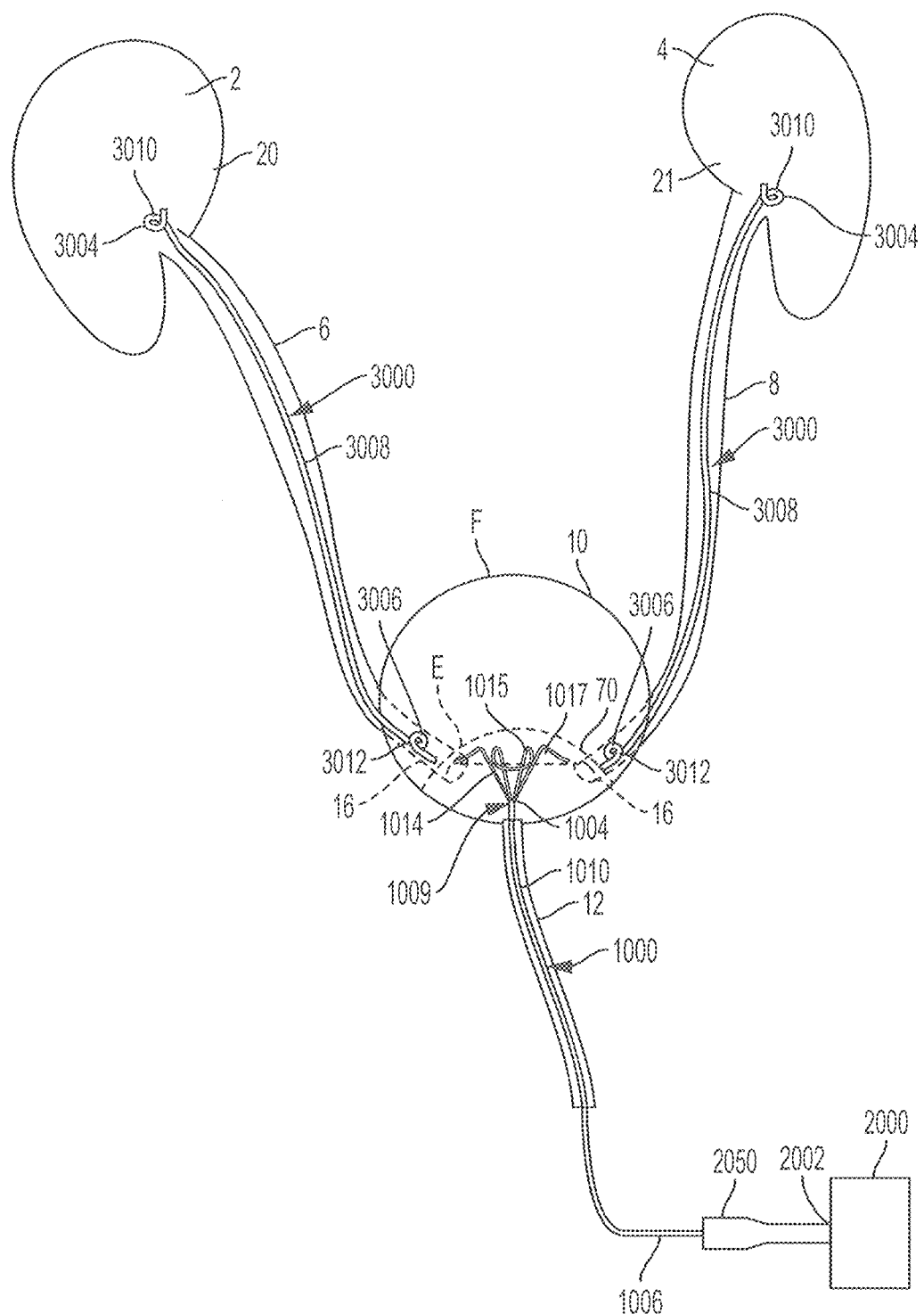
FIG. 21 is a schematic drawing of an indwelling portion of a urine collection assembly deployed in a urinary tract of a patient that includes ureteral stents and a bladder catheter, according to an example of the present invention.

In some examples, referring to FIG. 21, the previously described ureteral catheters 1000 are used as a bladder catheter. For instance, any of the previously described ureteral catheters 1000 comprising any one of the previously described retention portions 1015 can be placed in the bladder 10 to facilitate urine output from the bladder 10. The catheters 1000 can be placed in the bladder 10 such that the distal end 1004 of the tube 1002 and retention portion 1015 are positioned in the bladder 10 with the elongated tube 1002 extending out from the bladder 10 and into the urethra of the patient. The tube 1002 can also include at least one opening 1009 for urine to pass through the distal end 1004 and/or sidewall 1010 of the drainage lumen. When placed in the bladder 10, the catheters 1000 can be used with any of the previously described additional components including, but not limited to, a deployable seal, anchor, and/or a pump 2000 for inducing negative pressure.

It is appreciated that the dimensions of the catheters 1000 when used in the bladder 10 will be adjusted to fit the bladder 10. In some examples, the catheter 1000 is adjusted to a size that can range from about 8 Fr to about 24 Fr, an external diameter ranging from about 2.7 to about 8 mm, and an internal diameter ranging from about 2.16 to about 6.2 mm. The catheters 1000 when used in the bladder 10 can be available in different lengths to accommodate anatomical differences for gender and/or patient size such as previously described with other bladder catheters 116.

Further, the maximum cross sectional area of the three-dimensional shape defined by the deployed expandable retention portion in a plane transverse to a central axis of the expandable retention portion can be up to about 1000 mm$^2$, or from about 100 mm$^2$ to about 1000 mm$^2$. The axial length of the expandable portion from a proximal end to a distal end thereof can also be from about 5 mm to about 100 mm.

As previously described, the bladder 10 is transitionable from an empty position (signified by reference line E) to a full position (signified by reference line F). Referring again to FIG. 21, when the bladder is in the empty position E, the bladder superior wall 70 can be positioned adjacent to and/or conform to the periphery 1017 of the distal end 1004 and/or retention portion 1015 of the bladder catheter 1000.

In some examples, a method is also provided for facilitating urine output from the bladder 10 using the previously described catheters 1000. The method comprises: inserting a catheter 1000 of the present invention as disclosed herein into at the bladder 10; deploying the expandable retention portion 1015 in the patient's bladder 10 to maintain the distal end 1004 of the tube 1002 at a desired position in the bladder 10 of the patient; and applying negative pressure to the proximal portion of the tube 1002 of the catheter 1000 for a period of time to facilitate urine output from the bladder 10. The elongated tube 1002 also includes at least one opening at the distal end 1004 and/or sidewall 1010 to facilitate removal of fluids.

It is appreciated that the previously described catheters 1000 can be used in the bladder 10 and in the kidney, renal pelvis, and/or in a ureter adjacent to the renal pelvis of a patient as previously described. For instance, the present invention can comprise: a ureteral catheter 1000 placed in a kidney, renal pelvis, and/or in a ureter adjacent to the renal pelvis of a patient as shown in FIG. 1; and a bladder catheter 1000 placed in the bladder as shown in FIG. 21. The catheters 1000 can include any of the catheters 1000 and retention portions 1015 described herein. Further, the ureteral catheter 1000 can be placed in one or both kidneys, renal pelvises, and/or ureters adjacent to the renal pelvises.

In some examples, when the previously described ureteral catheters 1000 are used as a bladder catheter in the bladder 10, different ureteral catheters other than those previously described can be placed in the kidney, renal pelvis, and/or in a ureter adjacent to the renal pelvis. Such ureteral catheters are described in paragraphs [0018] to [0240] and the corresponding figures of U.S. Publication No. 2017/0348507, which is incorporated by reference herein.

In other examples, when the previously described ureteral catheters 1000 are used as a bladder catheter in the bladder 10, a ureteral stent 3000 is placed in the kidney, renal pelvis, and/or in a ureter adjacent to the renal pelvis. As shown in FIG. 21, the stent 3000 can comprise: a distal end 3004 placed in the kidney, renal pelvis, and/or in a ureter adjacent to the renal pelvis; a proximal end 3006 that terminates in the bladder 10; and a sidewall 3008 that extends between the distal end 3004 and proximal end 3006. Further, the ureteral stent 3000 can be placed in one or both kidneys, renal pelvises, and/or ureters adjacent to the renal pelvises.

In some examples, a method is provided for removing fluid from the urinary tract of a patient, the method comprising: deploying a ureteral stent 3000 or ureteral catheter into a ureter of a patient to maintain patency of fluid flow between a kidney 2, 4 and a bladder 10 of the patient; deploying a bladder catheter 1000 into the bladder of the patient, wherein the bladder catheter 1000 comprises the catheters 1000 described herein in which a distal end 1004 of a tube 1002 is configured to be positioned in a patient's bladder 10, a proximal end 1006 of the tube 1002 extends out of the bladder 10, and a sidewall 1010 extending therebetween; and applying negative pressure to the proximal end 1006 of the catheter 1000 to induce negative pressure in a portion of the urinary tract of the patient to remove fluid from the urinary tract of the patient.

Exemplary Ureteral Stents:

As previously described, and as shown in FIG. 21, the present invention can include the previously described ureteral catheters 1000 used as a bladder catheter in the bladder 10, and a ureteral stent 3000 placed one or both of the kidneys, renal pelvises, and/or ureters adjacent to the renal pelvises.

In some examples, the ureteral stent 3000 comprises an elongated body comprising a proximal end 3006, a distal end 3004, a longitudinal axis, and at least one drainage channel that extends along the longitudinal axis from the proximal end 3006 to the distal end 3004 to maintain patency of fluid flow between a kidney and a bladder of the patient. In some examples, the ureteral stent 3000 further comprises a pigtail coil or loop(s) 3010 or 3012 on at least one of the proximal end 3006 or the distal end 3006. In some examples, the body of the ureteral stent 3000 further comprises at least one perforation on a sidewall 3008 thereof. In other examples, the body of the ureteral stent 3000 is essentially free of or free of perforation(s) on a sidewall thereof.

Some examples of ureteral stents 3000 that can be useful in the present systems and methods include CONTOUR™ ureteral stents, CONTOUR VL™ ureteral stents, POLARIS™ Loop ureteral stents, POLARIS™ Ultra ureteral stents, PERCUFLEX™ ureteral stents, PERCUFLEX™ Plus ureteral stents, STRETCH™ VL Flexima ureteral stents, each of which are commercially available from Boston Scientific Corporation of Natick, Massachusetts See "Ureteral Stent Portfolio", a publication of Boston Scientific Corp., (July 2010), hereby incorporated by reference herein. The CONTOUR™ and CONTOUR VL™ ureteral stents are constructed with soft Percuflex™ Material that becomes soft at body temperature and is designed for a 365-day indwelling time. Variable length coils on distal and proximal ends allow for one stent to fit various ureteral lengths. The fixed length stent can be 6 F-8 F with lengths ranging from 20 cm-30 cm, and the variable length stent can be 4.8 F-7 F with lengths of 22-30 cm. Other examples of suitable ureteral stents include INLAY® ureteral stents, INLAY® OPTIMA® ureteral stents, BARDEX®double pigtail ureteral stents, and FLUORO-4™ silicone ureteral stent, each of which are commercially available from C.R. Bard, Inc. of Murray Hill, NJ See "Ureteral Stents", http://www.bardmedical.com/products/kidney-stone-management/ureteral-stents/(Jan. 21, 2018), hereby incorporated by reference herein.

The stents 3000 can be deployed in one or both of the patient's kidneys or kidney area (renal pelvis or ureters adjacent to the renal pelvis), as desired. Typically, these stents 3000 are deployed by inserting a stent having a nitinol wire therethrough through the urethra and bladder up to the kidney, then withdrawing the nitinol wire from the stent, which permits the stent to assume a deployed configuration. Many of the above stents have a planar loop 3010 on the distal end 3004 (to be deployed in the kidney), and some also have a planar loop 3012 on the proximal end 3006 of the stent 3000 which is deployed in the bladder. When the nitinol wire is removed, the stent 3000 assumes the prestressed planar loop shape 3010 or 3012 at the distal 3004 and/or proximal 3006 ends. To remove the stent 3000, a nitinol wire is inserted to straighten the stent 3000 and the stent 3000 is withdrawn from the ureter and urethra.

Other examples of suitable ureteral stents 3000 are disclosed in PCT Patent Application Publication WO 2017/019974, which is incorporated by reference herein. In some examples, as shown, for example, in FIGS. 1-7 of WO 2017/019974 and in FIG. 22 herein (same as FIG. 1 of WO 2017/019974), the ureteral stent 100 can comprise: an elongated body 101 comprising a proximal end 102, a distal end 104, a longitudinal axis 106, an outer surface 108, and an inner surface 110, wherein the inner surface 110 defines a transformable bore 111 that extends along the longitudinal axis 106 from the proximal end 102 to the distal end 104; and at least two fins 112 projecting radially away from the outer surface 108 of the body 101; wherein the transformable bore 111 comprises: (a) a default orientation 113A (shown on the left in FIG. 22) comprising an open bore 114 defining a longitudinally open channel 116; and (b) a second orientation 113B (shown on the right in FIG. 22) comprising an at least essentially closed bore 118 or closed bore defining a longitudinally essentially closed drainage channel 120 along the longitudinal axis 106 of the elongated body 101, wherein the transformable bore 111 is moveable from the default orientation 113A to the second orientation 113B upon radial compression forces 122 being applied to at least a portion of the outer surface 108 of the body 101.

Figure 22:
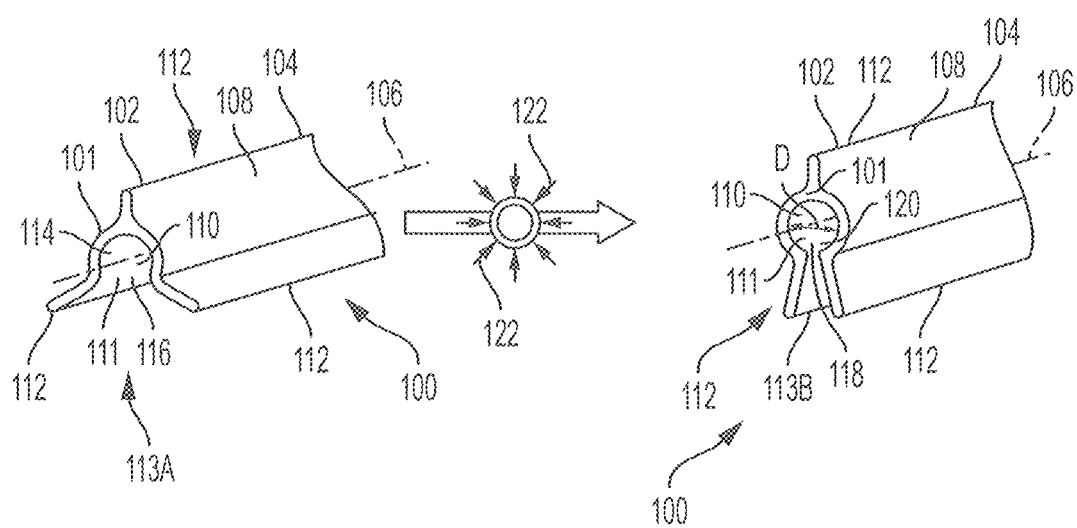
FIG. 22 is a dimetric view of an example of a prior art transformable ureteral stent according to FIG. 1 of PCT Patent Application Publication WO 2017/019974, wherein the image on the left represents the uncompressed state of the stent and the image on the right represents the compressed state of the stent.

In some examples, as shown in FIG. 22, the drainage channel 120 of the ureteral stent 100 has a diameter D which is reduced upon the transformable bore 111 moving from the default orientation 113A to the second orientation 113B, wherein the diameter is reducible up to the point above where urine flow through the transformable bore 111 would be reduced. In some examples, the diameter D is reduced by up to about 40% upon the transformable bore 111 moving from the default orientation 113A to the second orientation 113B. In some examples, the diameter D in the default orientation 113A can range from about 0.75 to about 5.5 mm, or about 1.3 mm or about 1.4 mm. In some examples, the diameter D in the second orientation 113B can range from about 0.4 to about 4 mm, or about 0.9 mm.

In some examples, one or more fins 112 comprise a flexible material that is soft to medium soft based on the Shore hardness scale. In some examples, the body 101 comprises a flexible material that is medium hard to hard based on the Shore hardness scale. In some examples, one or more fins have a durometer between about 15 A to about 40 A. In some examples, the body 101 has a durometer between about 80A to about 90 A. In some examples, one or more fins 112 and the body 101 comprise a flexible material that is medium soft to medium hard based on the Shore hardness scale, for example having a durometer between about 40 A to about 70 A.

In some examples, one or more fins 112 and the body 101 comprise a flexible material that is medium hard to hard based on the Shore hardness scale, for example having a durometer between about 85 A to about 90 A.

In some examples, the default orientation 113A and the second orientation 113B support fluid or urine flow around the outer surface 108 of the stent 100 in addition to through the transformable bore 111.

In some examples, one or more fins 112 extend longitudinally from the proximal end 102 to the distal end 104. In some examples, the stent has two, three or four fins.

In some examples, the outer surface 108 of the body has an outer diameter in the default orientation 113A ranging from about 0.8 mm to about 6 mm, or about 3 mm. In some examples, the outer surface 108 of the body has an outer diameter in the second orientation 113B ranging from about 0.5 mm to about 4.5 mm, or about 1 mm. In some examples, one or more fins have a width or tip ranging from about 0.25 mm to about 1.5 mm, or about 1 mm, projecting from the outer surface 108 of the body in a direction generally perpendicular to the longitudinal axis.

In some examples, the radial compression forces are provided by at least one of normal ureter physiology, abnormal ureter physiology, or application of any external force. In some examples, the ureteral stent 100 purposefully adapts to a dynamic ureteral environment, the ureteral stent 100 comprising: an elongated body 101 comprising a proximal end 102, a distal end 104, a longitudinal axis 106, an outer surface 108, and an inner surface 110, wherein the inner surface 110 defines a transformable bore 111 that extends along the longitudinal axis 106 from the proximal end 102 to the distal end 104; wherein the transformable bore 111 comprises: (a) a default orientation 113A comprising an open bore 114 defining a longitudinally open channel 116; and (b) a second orientation 113B comprising an at least essentially closed bore 118 defining a longitudinally essentially closed channel 120, wherein the transformable bore is moveable from the default orientation 113A to the second orientation 113B upon radial compression forces 122 being applied to at least a portion of the outer surface 108 of the body 101, wherein the inner surface 110 of the body 101 has a diameter D which is reduced upon the transformable bore 111 moving from the default orientation 113A to the second orientation 113B, wherein the diameter is reducible up to the point above where fluid flow through the transformable bore 111 would be reduced. In some examples, the diameter D is reduced by up to about 40% upon the transformable bore 111 moving from the default orientation 113A to the second orientation 113B.

Figure 23:
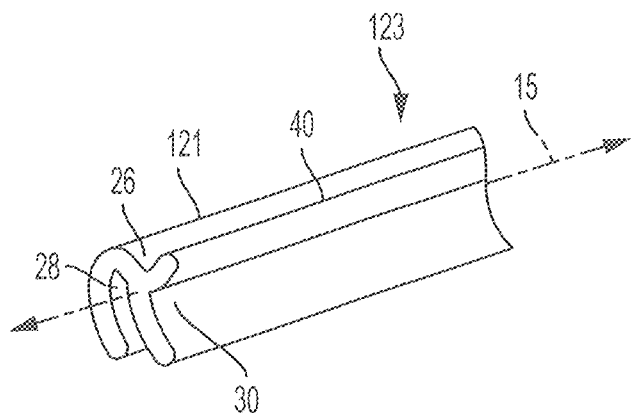
FIG. 23 is a perspective view of an example of a prior art ureteral stent according to FIG. 4 of US Patent Application Publication No. 2002/0183853 A1.
Figure 24:
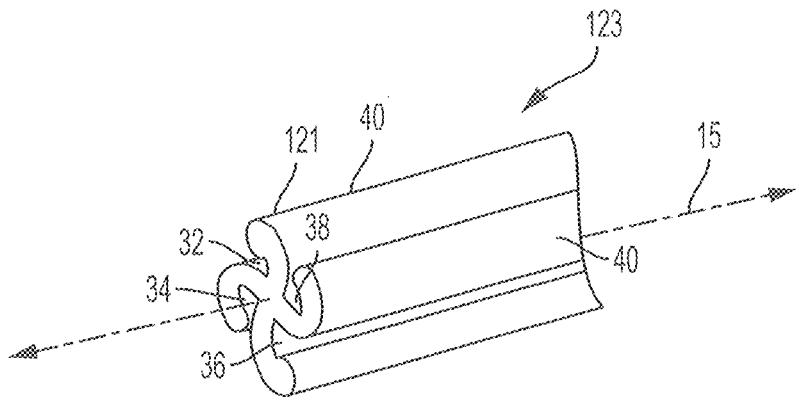
FIG. 24 is a perspective view of an example of a prior art ureteral stent according to FIG. 5 of US Patent Application Publication No. 2002/0183853 A1.
Figure 25:
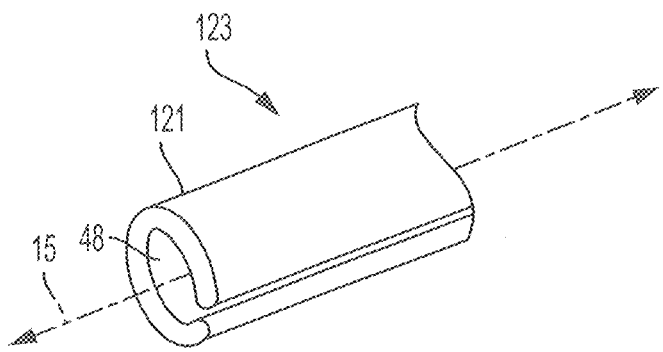
FIG. 25 is a perspective view of an example of a prior art ureteral stent according to FIG. 7 of US Patent Application Publication No. 2002/0183853 A1.

Other examples of suitable ureteral stents are disclosed in US Patent Application Publication US 2002/0183853 A1, which is incorporated by reference herein. In some examples, as shown, for example, in FIGS. 4, 5 and 7 of US 2002/0183853 A1 and in FIGS. 23-25 herein (same as FIGS. 4, 5 and 7 of US 2002/0183853 A1), the ureteral stent comprises an elongated, body 10 comprising a proximal end 121, a distal end 141 (not shown), a longitudinal axis 15, and at least one drainage channel (for example, 26, 28, 30 in FIGS. 4; 32, 34, 36 and 38 in FIGS. 24; and 48 in FIG. 25) that extends along the longitudinal axis 15 from the proximal end 121 to the distal end 141 to maintain patency of fluid flow between a kidney and a bladder of the patient. In some examples, the at least one drainage channel is partially open along at least a longitudinal portion thereof. In some examples, the at least one drainage channel is closed along at least a longitudinal portion thereof. In some examples, the at least one drainage channel is closed along the longitudinal length thereof. In some examples, the ureteral stent is radially compressible. In some examples, the ureteral stent is radially compressible to narrow the at least one drainage channel. In some examples, the elongated body 123 comprises at least one external fin 40 along the longitudinal axis 15 of the elongated body 123. In some examples, the elongated body comprises one to four drainage channels. The diameter of the drainage channel can be the same as described above.

Figure 12A:
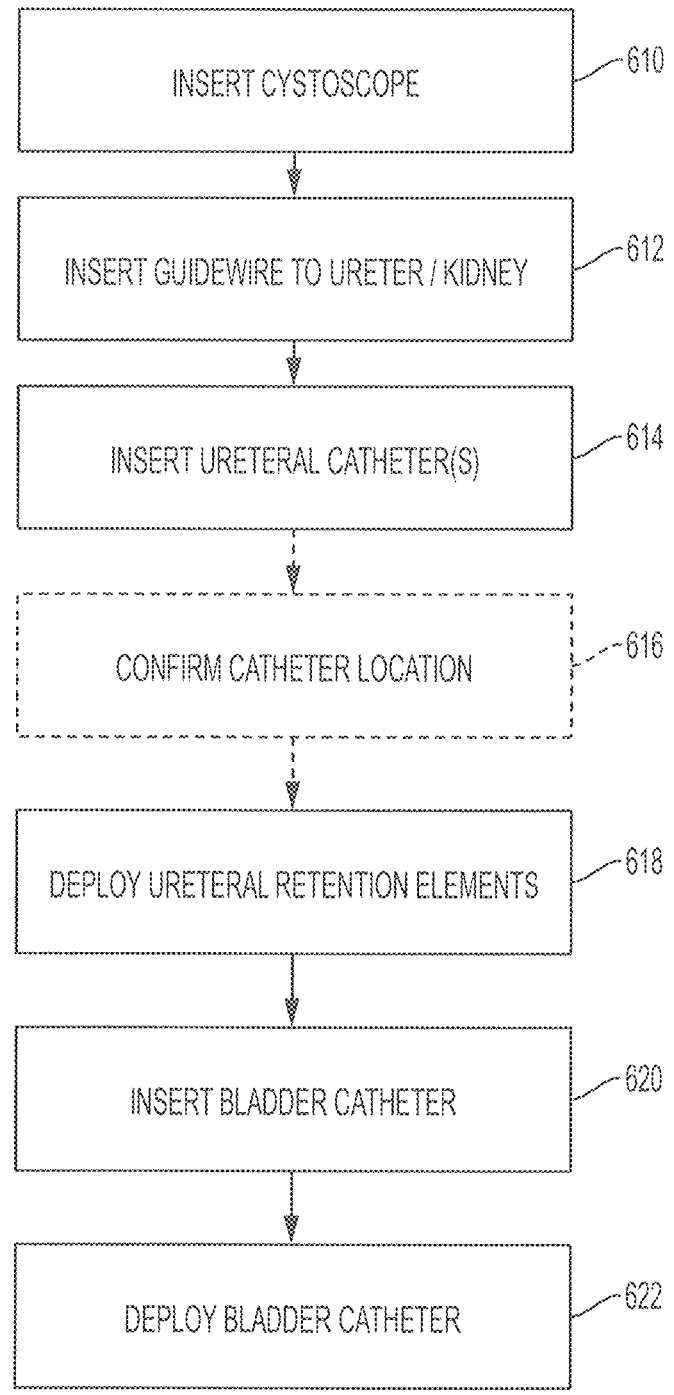
FIG. 12A is a flow chart illustrating a process for insertion and deployment of a ureteral catheter or urine collection assembly according to an example of the present invention.

Method of Insertion of a Urine Collection Assembly:

With reference to FIG. 12A, steps for positioning a fluid collection assembly in a patient's body and, optionally, for inducing negative pressure in a patient's ureter and/or kidneys are illustrated. As shown at box 610, a medical professional or caregiver inserts a flexible or rigid cystoscope through the patient's urethra and into the bladder to obtain visualization of the ureteral orifices or openings. Once suitable visualization is obtained, as shown at box 612, a guidewire is advanced through the urethra, bladder, ureteral opening, ureter, and to a desired fluid collection position, such as the renal pelvis of the kidney. Once the guidewire is advanced to the desired fluid collection position, a ureteral catheter of the present invention (examples of which are discussed in detail above) is inserted over the guidewire to the fluid collection position, as shown at box 614. In some examples, the location of the ureteral catheter can be confirmed by fluoroscopy, as shown at box 616. Once the position of the distal end of the catheter is confirmed, as shown at box 618, the retention portion of the ureteral catheter can be deployed. For example, the guidewire can be removed from the catheter, thereby allowing the distal end and/or retention portion to transition to a deployed position. In some examples, the deployed distal end portion of the catheter does not entirely occlude the ureter and/or renal pelvis, such that urine is permitted to pass outside the catheter and through the ureters into the bladder. Since moving the catheter can exert forces against urinary tract tissues, avoiding complete blockage of the ureters avoids application of force to the ureter sidewalls, which may cause injury.

After the ureteral catheter is in place and deployed, the same guidewire can be used to position a second ureteral catheter in the other ureter and/or kidney using the same insertion and positioning methods described herein. For example, the cystoscope can be used to obtain visualization of the other ureteral opening in the bladder, and the guidewire can be advanced through the visualized ureteral opening to a fluid collection position in the other ureter. A catheter can be drawn alongside the guidewire and deployed in the manner described herein. Alternatively, the cystoscope and guidewire can be removed from the body. The cystoscope can be reinserted into the bladder over the first ureteral catheter. The cystoscope is used, in the manner described above, to obtain visualization of the ureteral opening and to assist in advancing a second guidewire to the second ureter and/or kidney for positioning of the second ureteral catheter. Once the ureteral catheters are in place, in some examples, the guidewire and cystoscope are removed. In other examples, the cystoscope and/or guidewire can remain in the bladder to assist with placement of the bladder catheter.

Optionally, a bladder catheter can also be used. Once the ureteral catheters are in place, as shown at box 620, the medical professional or caregiver can insert a distal end of a bladder catheter in a collapsed or contracted state through the urethra of the patient and into the bladder. The bladder catheter can be a conventional Foley bladder catheter or a bladder catheter of the present invention as discussed in detail above. Once inserted in the bladder, as shown at box 622, an anchor connected to and/or associated with the bladder catheter is expanded to a deployed position. For example, when an expandable or inflatable catheter is used, fluid may be directed through an inflation lumen of the bladder catheter to expand a balloon structure located in the patient's bladder. In some examples, the bladder catheter is inserted through the urethra and into the bladder without using a guidewire and/or cystoscope. In other examples, the bladder catheter is inserted over the same guidewire used to position the ureteral catheters. Accordingly, when inserted in this manner, the ureteral catheters can be arranged to extend from the distal end of the bladder catheter and, optionally, proximal ends of the ureteral catheters can be arranged to terminate in a drainage lumen of the bladder catheter.

In some examples, the urine is permitted to drain by gravity or peristalsis from the urethra. In other examples, a negative pressure is induced in the ureteral catheter and/or bladder catheter to facilitate drainage of the urine.

Figure 12B:
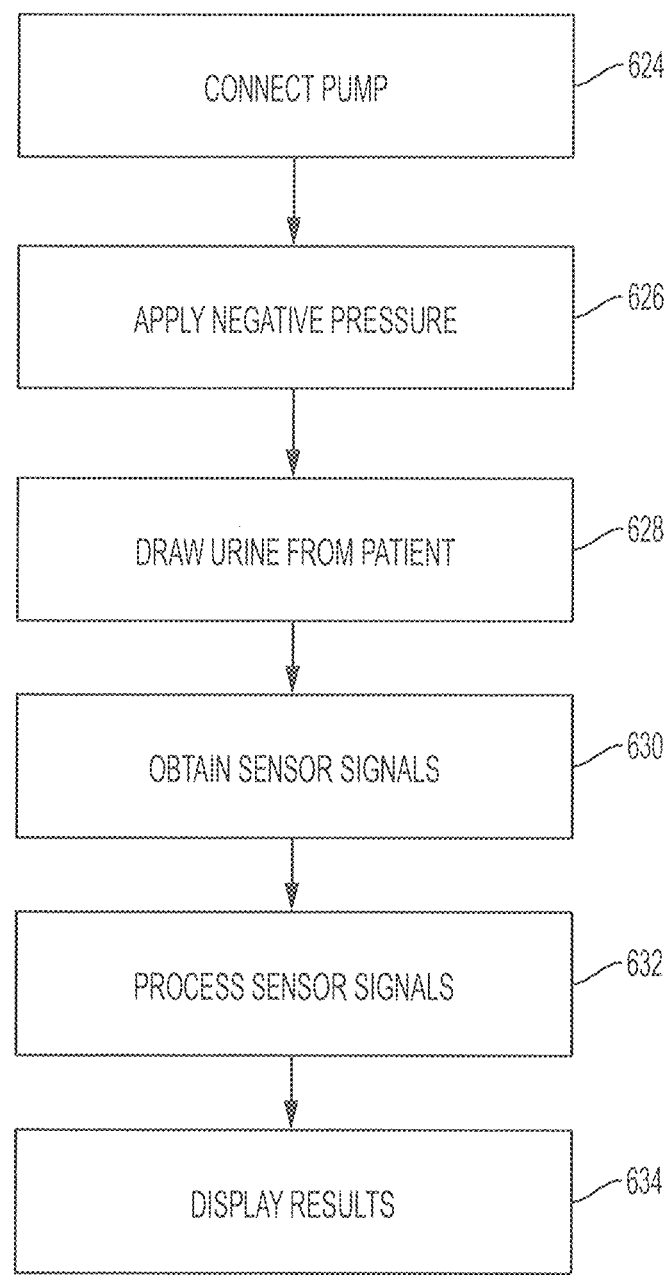
FIG. 12B is a flow chart illustrating a process for applying negative pressure using a ureteral catheter or urine collection assembly according to an example of the present invention.

With reference to FIG. 12B, steps for using the urine collection assembly for inducement of negative pressure in the ureter(s) and/or kidney(s) are illustrated. As shown at box 624, after the indwelling portions of the bladder and/or ureteral catheters are correctly positioned and anchoring/retention structures are deployed, the external proximal ends of the catheter(s) are connected to fluid collection or pump assemblies. For example, the ureteral catheter(s) can be connected to a pump for inducing negative pressure at the patient's renal pelvis and/or kidney. In a similar manner, the bladder catheter can be connected directly to a urine collection container for gravity drainage of urine from the bladder or connected to a pump for inducing negative pressure at the bladder.

Once the catheter(s) and pump assembly are connected, negative pressure is applied to the renal pelvis and/or kidney and/or bladder through the drainage lumens of the ureteral catheters and/or bladder catheter, as shown at box 626. The negative pressure is intended to counter congestion mediated interstitial hydrostatic pressures due to elevated intra-abdominal pressure and consequential or elevated renal venous pressure or renal lymphatic pressure. The applied negative pressure is therefore capable of increasing flow of filtrate through the medullary tubules and of decreasing water and sodium re-absorption.

In some examples, mechanical stimulation can be provided to portions of the ureters and/or renal pelvis to supplement or modify therapeutic affects obtained by application of negative pressure. For example, mechanical stimulation devices, such as linear actuators and other known devices for providing, for example, vibration waves, disposed in distal portions of the ureteral catheter(s) can be actuated. While not intending to be bound by theory, it is believed that such stimulation effects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy. In some examples, the mechanical stimulation can comprise pulsating stimulation. In other examples, low levels of mechanical stimulation can be provided continuously as negative pressure is being provided through the ureteral catheter(s). In other examples, inflatable portions of the ureteral catheter could be inflated and deflated in a pulsating manner to stimulate adjacent nerve and muscle tissue, in a similar manner to actuation of the mechanical stimulation devices described herein.

As a result of the applied negative pressure, as shown at box 628, urine is drawn into the catheter at the plurality of drainage ports at the distal end thereof, through the drainage lumen of the catheter, and to a fluid collection container for disposal. As the urine is being drawn to the collection container, at box 630, sensors disposed in the fluid collection system provide a number of measurements about the urine that can be used to assess the volume of urine collected, as well as information about the physical condition of the patient and composition of the urine produced. In some examples, the information obtained by the sensors is processed, as shown at box 632, by a processor associated with the pump and/or with another patient monitoring device and, at box 634, is displayed to the user via a visual display of an associated feedback device.

Figure 13:
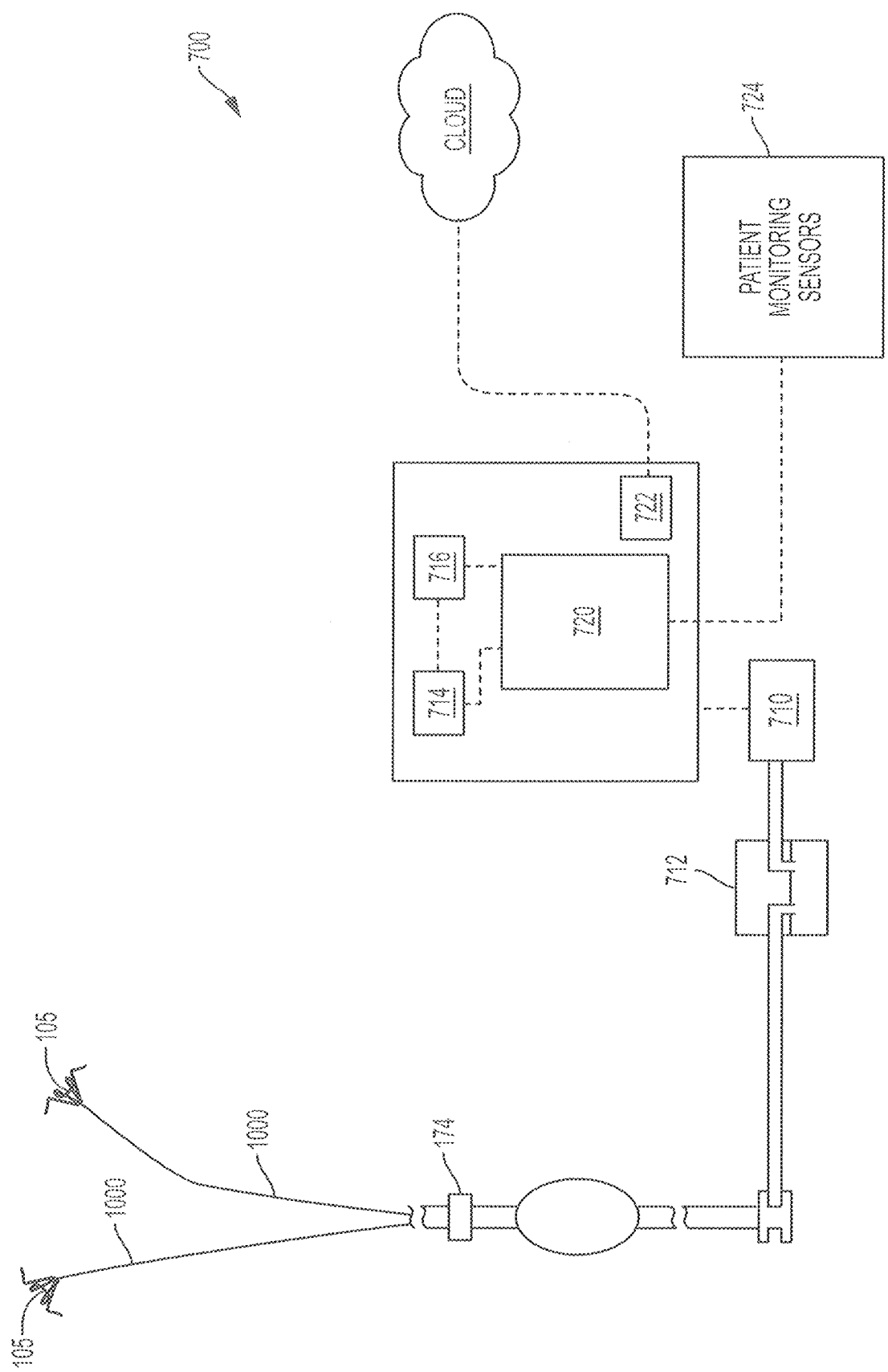
FIG. 13 is a schematic drawing of a system for inducing negative pressure to the urinary tract of a patient according to an example of the present invention.

Exemplary Fluid Collection System:

Having described an exemplary urine collection assembly and method of positioning such an assembly in the patient's body, with reference to FIG. 13, a system 700 for inducing negative pressure to a patient's ureter(s) and/or kidney(s) will now be described. The system 700 can comprise the ureteral catheter(s), bladder catheter or the urine collection assembly described hereinabove. As shown in FIG. 13, ureteral catheters 1000 and/or the bladder catheter are connected to one or more fluid collection containers 712 for collecting urine drawn from the renal pelvis and/or bladder. In some examples, the bladder catheter and the ureteral catheters 1000 are connected to different fluid collection containers 712. The fluid collection container 712 connected to the ureteral catheter(s) 1000 can be in fluid communication with an external fluid pump 710 for generating negative pressure in the ureter(s) and kidney(s) through the ureteral catheter(s) 1000. As discussed herein, such negative pressure can be provided for overcoming interstitial pressure and forming urine in the kidney or nephron. In some examples, a connection between the fluid collection container 712 and pump 710 can comprise a fluid lock or fluid barrier to prevent air from entering the renal pelvis or kidney in case of incidental therapeutic or non-therapeutic pressure changes. For example, inflow and outflow ports of the fluid container can be positioned below a fluid level in the container. Accordingly, air is prevented from entering medical tubing or the catheter through either the inflow or outflow ports of the fluid container 712. As discussed previously, external portions of the tubing extending between the fluid collection container 712 and the pump 710 can include one or more filters to prevent urine and/or particulates from entering the pump 710.

As shown in FIG. 13, the system 700 further comprises a controller 714, such as a microprocessor, electronically coupled to the pump 710 and having or associated with computer readable memory 716. In some examples, the memory 716 comprises instructions that, when executed, cause the controller 714 to receive information from sensors 174 located on or associated with portions of the assembly. Information about a condition of the patient can be determined based on information from the sensors 174. Information from the sensors 174 can also be used to determine and implement operating parameters for the pump 710.

In some examples, the controller 714 is incorporated in a separate and remote electronic device in communication with the pump 710, such as a dedicated electronic device, computer, tablet PC, or smart phone. Alternatively, the controller 714 can be included in the pump 710 and, for example, can control both a user interface for manually operating the pump 710, as well as system functions such as receiving and processing information from the sensors 174.

The controller 714 is configured to receive information from the one or more sensors 174 and to store the information in the associated computer-readable memory 716. For example, the controller 714 can be configured to receive information from the sensor 174 at a predetermined rate, such as once every second, and to determine a conductance based on the received information. In some examples, the algorithm for calculating conductance can also include other sensor measurements, such as urine temperature, to obtain a more robust determination of conductance.

The controller 714 can also be configured to calculate patient physical statistics or diagnostic indicators that illustrate changes in the patient's condition over time. For example, the system 700 can be configured to identify an amount of total sodium excreted. The total sodium excreted may be based, for example, on a combination of flow rate and conductance over a period of time.

With continued reference to FIG. 13, the system 700 can further comprise a feedback device 720, such as a visual display or audio system, for providing information to the user. In some examples, the feedback device 720 can be integrally formed with the pump 710. Alternatively, the feedback device 720 can be a separate dedicated or a multipurpose electronic device, such as a computer, laptop computer, tablet PC, smart phone, or other handheld electronic devices. The feedback device 720 is configured to receive the calculated or determined measurements from the controller 714 and to present the received information to a user via the feedback device 720. For example, the feedback device 720 may be configured to display current negative pressure (in mmHg) being applied to the urinary tract. In other examples, the feedback device 720 is configured to display current flow rate of urine, temperature, current conductance in mS/m of urine, total urine produced during the session, total sodium excreted during the session, other physical parameters, or any combination thereof.

In some examples, the feedback device 720 further comprises a user interface module or component that allows the user to control operation of the pump 710. For example, the user can engage or turn off the pump 710 via the user interface. The user can also adjust pressure applied by the pump 710 to achieve a greater magnitude or rate of sodium excretion and fluid removal.

Optionally, the feedback device 720 and/or pump 710 further comprise a data transmitter 722 for sending information from the device 720 and/or pump 710 to other electronic devices or computer networks. The data transmitter 722 can utilize a short-range or long-range data communications protocol. An example of a short-range data transmission protocol is Bluetooth®. Long-range data transmission networks include, for example, Wi-Fi or cellular networks. The data transmitter 722 can send information to a patient's physician or caregiver to inform the physician or caregiver about the patient's current condition. Alternatively, or in addition, information can be sent from the data transmitter 722 to existing databases or information storage locations, such as, for example, to include the recorded information in a patient's electronic health record (EHR).

With continued reference to FIG. 13, in addition to the urine sensors 174, in some examples, the system 700 further comprises one or more patient monitoring sensors 724. Patient monitoring sensors 724 can include invasive and non-invasive sensors for measuring information about the patient's urine composition, as discussed in detail above, blood composition (e.g., hematocrit ratio, analyte concentration, protein concentration, creatinine concentration) and/or blood flow (e.g., blood pressure, blood flow velocity). Hematocrit is a ratio of the volume of red blood cells to the total volume of blood. Normal hematocrit is about 25% to 40%, and preferably about 35% and 40% (e.g., 35% to 40% red blood cells by volume and 60% to 65% plasma).

Non-invasive patient monitoring sensors 724 can include pulse oximetry sensors, blood pressure sensors, heart rate sensors, and respiration sensors (e.g., a capnography sensor). Invasive patient monitoring sensors 724 can include invasive blood pressure sensors, glucose sensors, blood velocity sensors, hemoglobin sensors, hematocrit sensors, protein sensors, creatinine sensors, and others. In still other examples, sensors may be associated with an extracorporeal blood system or circuit and configured to measure parameters of blood passing through tubing of the extracorporeal system. For example, analyte sensors, such as capacitance sensors or optical spectroscopy sensors, may be associated with tubing of the extracorporeal blood system to measure parameter values of the patient's blood as it passes through the tubing. The patient monitoring sensors 724 can be in wired or wireless communication with the pump 710 and/or controller 714.

In some examples, the controller 714 is configured to cause the pump 710 to provide treatment for a patient based information obtained from the urine analyte sensor 174 and/or patient monitoring sensors 724, such as blood monitoring sensors. For example, pump 710 operating parameters can be adjusted based on changes in the patient's blood hematocrit ratio, blood protein concertation, creatinine concentration, urine output volume, urine protein concentration (e.g., albumin), and other parameters. For example, the controller 714 can be configured to receive information about a blood hematocrit ratio or creatinine concentration of the patient from the patient monitoring sensors 724 and/or analyte sensors 174. The controller 714 can be configured to adjust operating parameters of the pump 710 based on the blood and/or urine measurements. In other examples, hematocrit ratio may be measured from blood samples periodically obtained from the patient. Results of the tests can be manually or automatically provided to the controller 714 for processing and analysis.

As discussed herein, measured hematocrit values for the patient can be compared to predetermined threshold or clinically acceptable values for the general population. Generally, hematocrit levels for females are lower than for males. In other examples, measured hematocrit values can be compared to patient baseline values obtained prior to a surgical procedure. When the measured hematocrit value is increased to within the acceptable range, the pump 710 may be turned off ceasing application of negative pressure to the ureter or kidneys. In a similar manner, the intensity of negative pressure can be adjusted based on measured parameter values. For example, as the patient's measured parameters begin to approach the acceptable range, intensity of negative pressure being applied to the ureter and kidneys can be reduced. In contrast, if an undesirable trend (e.g., a decrease in hematocrit value, urine output rate, and/or creatinine clearance) is identified, the intensity of negative pressure can be increased in order to produce a positive physiological result. For example, the pump 710 may be configured to begin by providing a low level of negative pressure (e.g., between about 0.1 mmHg and 10 mmHg). The negative pressure may be incrementally increased until a positive trend in patient creatinine level is observed. However, generally, negative pressure provided by the pump 710 will not exceed about 50 mmHg.

Figure 14A:
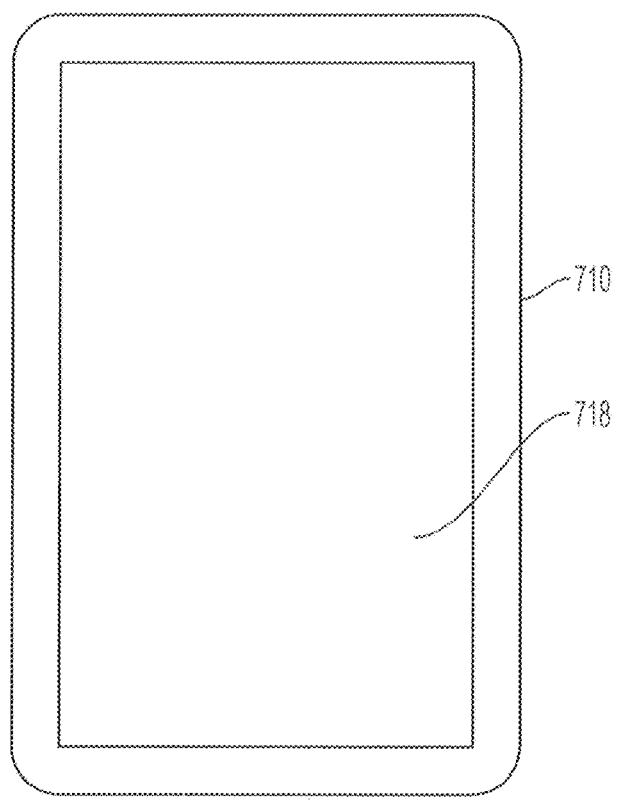
FIG. 14A is a plan view of a pump for use with the system of FIG. 13 according to an example of the present invention.
Figure 14B:
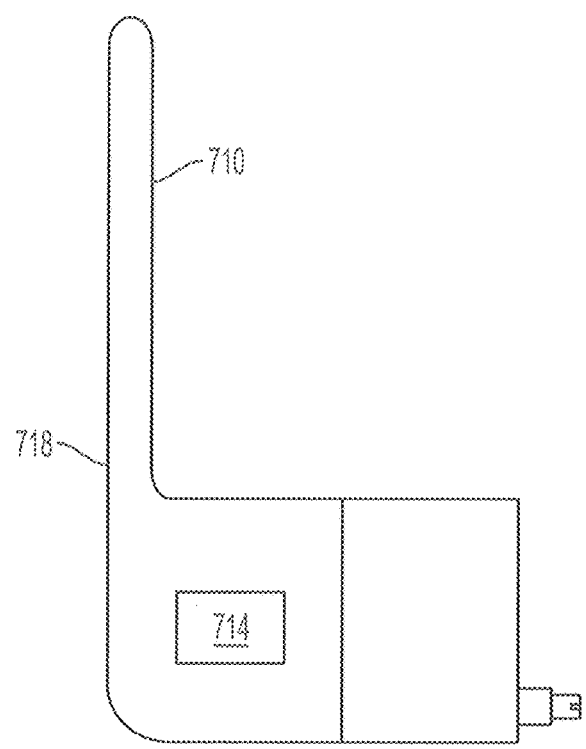
FIG. 14B is a side elevation view of the pump of FIG. 14A.

With reference to FIGS. 14A and 14B, an exemplary pump 710 for use with the system is illustrated. In some examples, the pump 710 is a micro-pump configured to draw fluid from the catheter(s) 1000 and having a sensitivity or accuracy of about 10 mmHg or less. Desirably, the pump 710 is capable of providing a range of flow of urine between 0.05 ml/min and 3 ml/min for extended periods of time, for example, for about 8 hours to about 24 hours per day, for one (1) to about 30 days or longer. At 0.2 ml/min, it is anticipated that about 300 mL of urine per day is collected by the system 700. The pump 710 can be configured to provide a negative pressure to the bladder of the patient, the negative pressure ranging between about 0.1 mmHg and 50 mmHg or about 5 mmHg to about 20 mmHg (gauge pressure at the pump 710). For example, a micro-pump manufactured by Langer Inc. (Model BT100-2J) can be used with the presently disclosed system 700. Diaphragm aspirator pumps, as well as other types of commercially available pumps, can also be used for this purpose. Peristaltic pumps can also be used with the system 700. In other examples, a piston pump, vacuum bottle, or manual vacuum source can be used for providing negative pressure. In other examples, the system can be connected to a wall suction source, as is available in a hospital, through a vacuum regulator for reducing negative pressure to therapeutically appropriate levels.

In some examples, at least a portion of the pump assembly can be positioned within the patient's urinary tract, for example within the bladder. For example, the pump assembly can comprise a pump module and a control module coupled to the pump module, the control module being configured to direct motion of the pump module. At least one (one or more) of the pump module, the control module, or the power supply may be positioned within the patient's urinary tract. The pump module can comprise at least one pump element positioned within the fluid flow channel to draw fluid through the channel. Some examples of suitable pump assemblies, systems and methods of use are disclosed in U.S. Patent Application No. 62/550,259, entitled "Indwelling Pump for Facilitating Removal of Urine from the Urinary Tract", filed concurrently herewith, which is incorporated by reference herein in its entirety.

In some examples, the pump 710 is configured for extended use and, thus, is capable of maintaining precise suction for extended periods of time, for example, for about 8 hours to about 24 hours per day, for 1 to about 30 days or longer. Further, in some examples, the pump 710 is configured to be manually operated and, in that case, includes a control panel 718 that allows a user to set a desired suction value. The pump 710 can also include a controller or processor, which can be the same controller that operates the system 700 or can be a separate processor dedicated for operation of the pump 710. In either case, the processor is configured for both receiving instructions for manual operation of the pump and for automatically operating the pump 710 according to predetermined operating parameters. Alternatively, or in addition, operation of the pump 710 can be controlled by the processor based on feedback received from the plurality of sensors associated with the catheter.

In some examples, the processor is configured to cause the pump 710 to operate intermittently. For example, the pump 710 may be configured to emit pulses of negative pressure followed by periods in which no negative pressure is provided. In other examples, the pump 710 can be configured to alternate between providing negative pressure and positive pressure to produce an alternating flush and pump effect. For example, a positive pressure of about 0.1 mmHg to 20 mmHg, and preferably about 5 mmHg to 20 mmHg can be provided followed by a negative pressure ranging from about 0.1 mmHg to 50 mmHg.

Treatment for Removing Excess Fluid from a Patient with Hemodilution

According to another aspect of the disclosure, a method for removing excess fluid from a patient with hemodilution is provided. In some examples, hemodilution can refer to an increase in a volume of plasma in relation to red blood cells and/or a reduced concentration of red blood cells in circulation, as may occur when a patient is provided with an excessive amount of fluid. The method can involve measuring and/or monitoring patient hematocrit levels to determine when hemodilution has been adequately addressed. Low hematocrit levels are a common post-surgical or post-trauma condition that can lead to undesirable therapeutic outcomes. As such, management of hemodilution and confirming that hematocrit levels return to normal ranges is a desirable therapeutic result for surgical and post-surgical patient care.

Figure 15:
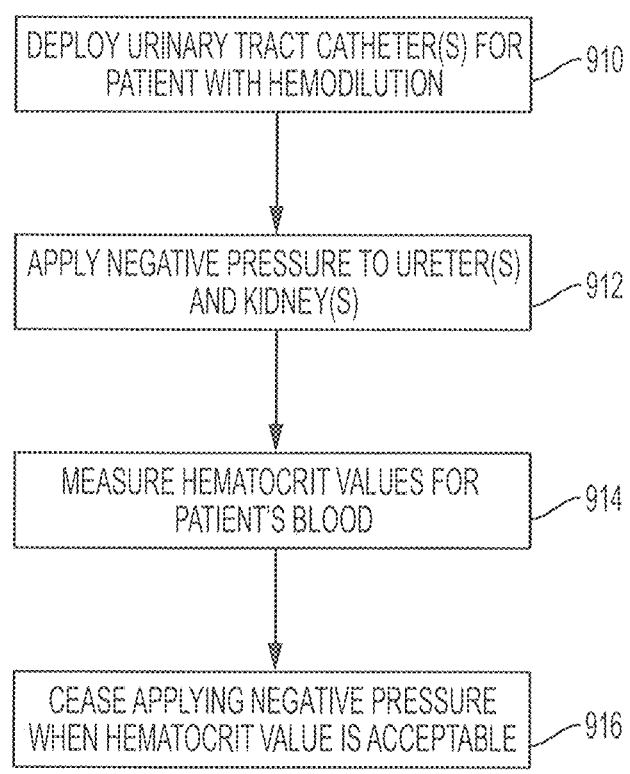
FIG. 15 is a flow chart illustrating a process for reducing creatinine and/or protein levels of a patient according to an example of the disclosure.

Steps for removing excess fluid from a patient using the devices and systems described herein are illustrated in FIG. 15. As shown in FIG. 15, the treatment method comprises deploying a urinary tract catheter, such as a ureteral catheter, in the ureter and/or kidney of a patient such that flow of urine from the ureter and/or kidney, as shown at box 910. The catheter may be placed to avoid occluding the ureter and/or kidney. In some examples, a fluid collecting portion of the catheter may be positioned in the renal pelvis of the patient's kidney. In some examples, a ureter catheter may be positioned in each of the patient's kidneys. In other examples, a urine collection catheter may be deployed in the bladder or ureter. In some examples, the ureteral catheter comprises one or more of any of the retention portions described herein.

As shown at box 912, the method further comprises applying negative pressure to the ureter and/or kidney through the catheter to induce production of urine in the kidney(s) and to extract urine from the patient. Desirably, negative pressure is applied for a period of time sufficient to reduce the patient's blood creatinine levels by a clinically significant amount.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when sufficient treatment has been provided. For example, as shown at box 914, the method may further comprise monitoring the patient to determine when to cease applying negative pressure to the patient's ureter and/or kidneys. In a preferred and non-limiting example, a patient's hematocrit level is measured. For example, patient monitoring devices may be used to periodically obtain hematocrit values. In other examples, blood samples may be drawn periodically to directly measure hematocrit. In some examples, concentration and/or volume of urine expelled from the body through the catheter may also be monitored to determine a rate at which urine is being produced by the kidneys. In a similar manner, expelled urine output may be monitored to determine protein concentration and/or creatinine clearance rate for the patient. Reduced creatinine and protein concentration in urine may be indicative of over-dilution and/or depressed renal function. Measured values can be compared to the predetermined threshold values to assess whether negative pressure therapy is improving patient condition, and should be modified or discontinued. For example, as discussed herein, a desirable range for patient hematocrit may be between 25% and 40%. In other preferred and non-limiting examples, as described herein, patient body weight may be measured and compared to a dry body weight. Changes in measured patient body weight demonstrate that fluid is being removed from the body. As such, a return to dry body weight represents that hemodilution has been appropriately managed and the patient is not over-diluted.

As shown at box 916, a user may cause the pump to cease providing negative pressure therapy when a positive result is identified. In a similar manner, patient blood parameters may be monitored to assess effectiveness of the negative pressure being applied to the patient's kidneys. For example, a capacitance or analyte sensor may be placed in fluid communication with tubing of an extracorporeal blood management system. The sensor may be used to measure information representative of blood protein, oxygen, creatinine, and/or hematocrit levels. Measured blood parameter values may be measured continuously or periodically and compared to various threshold or clinically acceptable values. Negative pressure may continue to be applied to the patient's kidney or ureter until a measured parameter value falls within a clinically acceptable range. Once a measured values fails within the threshold or clinically acceptable range, as shown at box 916, application of negative pressure may cease.

Treatment of Patients Undergoing a Fluid Resuscitation Procedure

According to another aspect of the disclosure, a method for removing excess fluid for a patient undergoing a fluid resuscitation procedure, such as coronary graft bypass surgery, by removing excess fluid from the patient is provided. During fluid resuscitation, solutions such as saline solutions and/or starch solutions, are introduced to the patient's bloodstream by a suitable fluid delivery process, such as an intravenous drip. For example, in some surgical procedures, a patient may be supplied with between 5 and 10 times a normal daily intake of fluid. Fluid replacement or fluid resuscitation can be provided to replace bodily fluids lost through sweating, bleeding, dehydration, and similar processes. In the case of a surgical procedure such as coronary graft bypass, fluid resuscitation is provided to help maintain a patient's fluid balance and blood pressure within an appropriate rate. Acute kidney injury (AKI) is a known complication of coronary artery graft bypass surgery. AKI is associated with a prolonged hospital stay and increased morbidity and mortality, even for patients who do not progress to renal failure. See Kim, et al., *Relationship between a perioperative intravenous fluid administration strategy and acute kidney injury following off-pump coronary artery bypass surgery: an observational study, Critical Care* 19:350 (1995). Introducing fluid to blood also reduces hematocrit levels which has been shown to further increase mortality and morbidity. Research has also demonstrated that introducing saline solution to a patient may depress renal functional and/or inhibit natural fluid management processes. As such, appropriate monitoring and control of renal function may produce improved outcomes and, in particular, may reduce post-operative instances of AKI.

Figure 16:
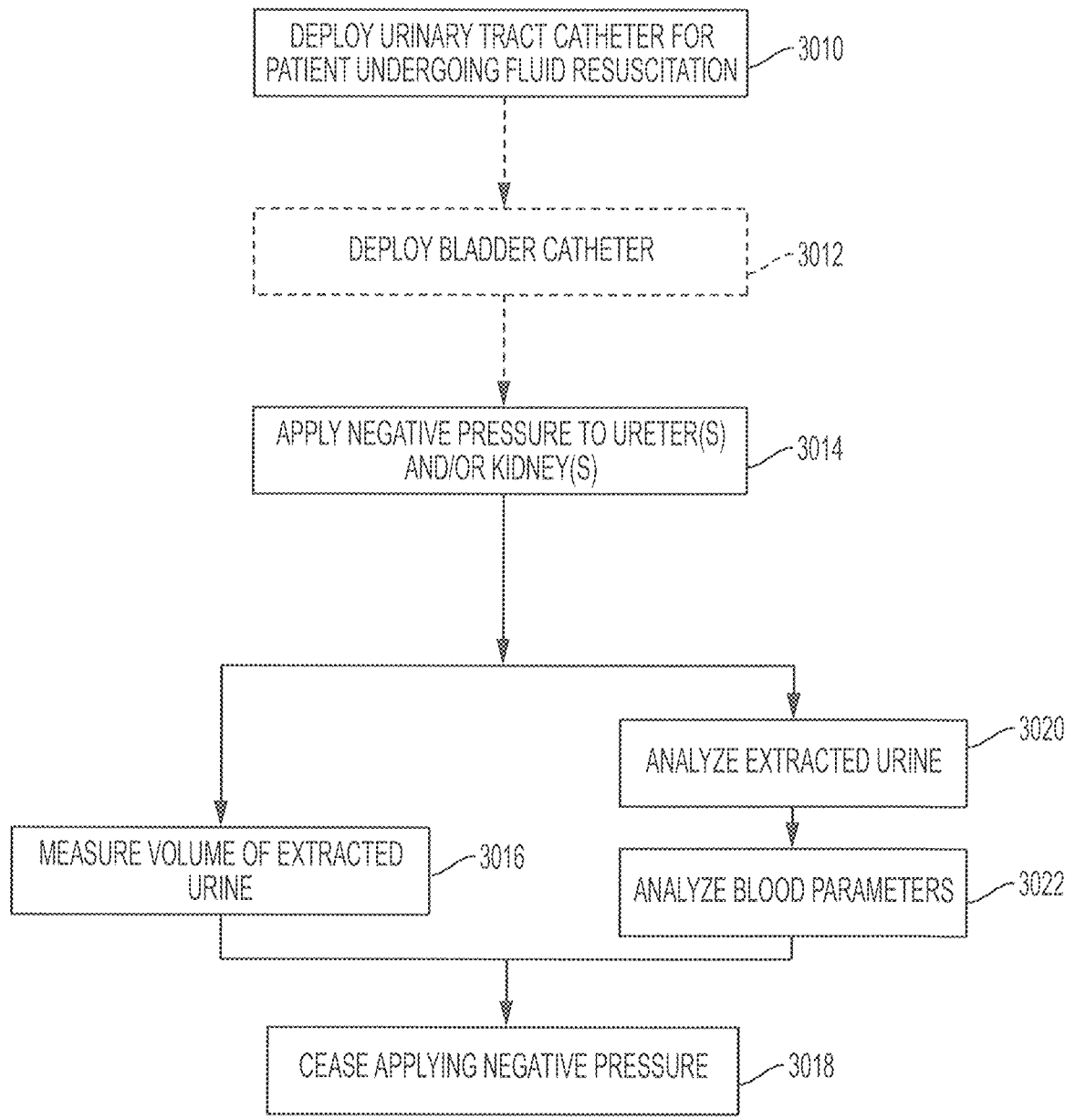
FIG. 16 is a flow chart illustrating a process for treating a patient undergoing fluid resuscitation according to an example of the disclosure.

A method of treating a patient undergoing fluid resuscitation is illustrated in FIG. 16. As shown at box 3010, the method comprises deploying a ureteral catheter in the ureter and/or kidney of a patient such that flow of urine from the ureter and/or kidney is not prevented by occlusion of the ureter and/or kidney. For example, a fluid collecting portion of the catheter may be positioned in the renal pelvis. In other examples, the catheter may be deployed in the bladder or ureter. The catheter can comprise one or more of the ureter catheters described herein.

As shown at box 3012, optionally, a bladder catheter may also be deployed in the patient's bladder. For example, the bladder catheter may be positioned to seal the urethra opening to prevent passage of urine from the body through the urethra. The bladder catheter can include an inflatable anchor (e.g., a Foley catheter) for maintaining the distal end of the catheter in the bladder. The bladder catheter can be configured to collect urine which entered the patient's bladder prior to placement of the ureteral catheter(s). The bladder catheter may also collect urine which flows past the fluid collection portion(s) of the ureteral catheter and enters the bladder. In some examples, a proximal portion of the ureteral catheter may be positioned in a drainage lumen of the bladder catheter. In a similar manner, the bladder catheter may be advanced into the bladder using the same guidewire used for positioning of the ureteral catheter(s). In some examples, negative pressure may be provided to the bladder through the drainage lumen of the bladder catheter. In other examples, negative pressure may only be applied to the ureteral catheter(s). In that case, the bladder catheter drains by gravity.

As shown at box 3014, following deployment of the ureteral catheter(s), negative pressure is applied to the ureter and/or kidney through the ureteral catheter(s). For example, negative pressure can be applied for a period of time sufficient to extract urine comprising a portion of the fluid provided to the patient during the fluid resuscitation procedure. As described herein, negative pressure can be provided by an external pump connected to a proximal end or port of the catheter. The pump can be operated continually or periodically dependent on therapeutic requirements of the patient. In some cases, the pump may alternate between applying negative pressure and positive pressure.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when a sufficient amount of fluid has been drawn from the patient. For example, as shown at box 3016, fluid expelled from the body may be collected and a total volume of obtained fluid may be monitored. In that case, the pump can continue to operate until a predetermined fluid volume has been collected from the ureteral and/or bladder catheters. The predetermined fluid volume may be based, for example, on a volume of fluid provided to the patient prior to and during the surgical procedure. As shown at box 3018, application of negative pressure to the ureter and/or kidneys is stopped when the collected total volume of fluid exceeds the predetermined fluid volume.

In other examples, operation of the pump can be determined based on measured physiological parameters of the patient, such as measured creatinine clearance, blood creatinine level, or hematocrit ratio. For example, as shown at box 3020, urine collected form the patient may be analyzed by one or more sensors associated with the catheter and/or pump. The sensor can be a capacitance sensor, analyte sensor, optical sensor, or similar device configured to measure urine analyte concentration. In a similar manner, as shown at box 3022, a patient's blood creatinine or hematocrit level could be analyzed based on information obtain from the patient monitoring sensors discussed hereinabove. For example, a capacitance sensor may be placed in an existing extracorporeal blood system. Information obtained by the capacitance sensor may be analyzed to determine a patient's hematocrit ratio. The measured hematocrit ratio may be compared to certain expected or therapeutically acceptable values. The pump may continue to apply negative pressure to the patient's ureter and/or kidney until measured values within the therapeutically acceptable range are obtained. Once a therapeutically acceptable value is obtained, application of negative pressure may be stopped as shown at box 3018.

In other examples, patient body weight may be measured to assess whether fluid is being removed from the patient by the applied negative pressure therapy. For example, a patient's measured bodyweight (including fluid introduced during a fluid resuscitation procedure) can be compared to a patient's dry body weight. As used herein, dry weights is defined as normal body weight measured when a patient is not over-diluted. For example, a patient who is not experiencing one or more of: elevated blood pressure, lightheadedness or cramping, swelling of legs, feet, arms, hands, or around the eyes, and who is breathing comfortably, likely does not have excess fluid. A weight measured when the patient is not experiencing such symptoms can be a dry body weight. Patient weight can be measured periodically until the measured weight approaches the dry body weight. When the measured weight approaches (e.g., is within between 5% and 10% of dry body weight), as shown at box 3018, application of negative pressure can be stopped.

EXPERIMENTAL EXAMPLES

Inducement of negative pressure within the renal pelvis of farm swine was performed for the purpose of evaluating effects of negative pressure therapy on renal congestion in the kidney. An objective of these studies was to demonstrate whether a negative pressure delivered into the renal pelvis significantly increases urine output in a swine model of renal congestion. In Example 1, a pediatric Fogarty catheter, normally used in embolectomy or bronchoscopy applications, was used in the swine model solely for proof of principle for inducement of negative pressure in the renal pelvis. It is not suggested that a Fogarty catheter be used in humans in clinical settings to avoid injury of urinary tract tissues.

Example 1

Method

Figure 17:
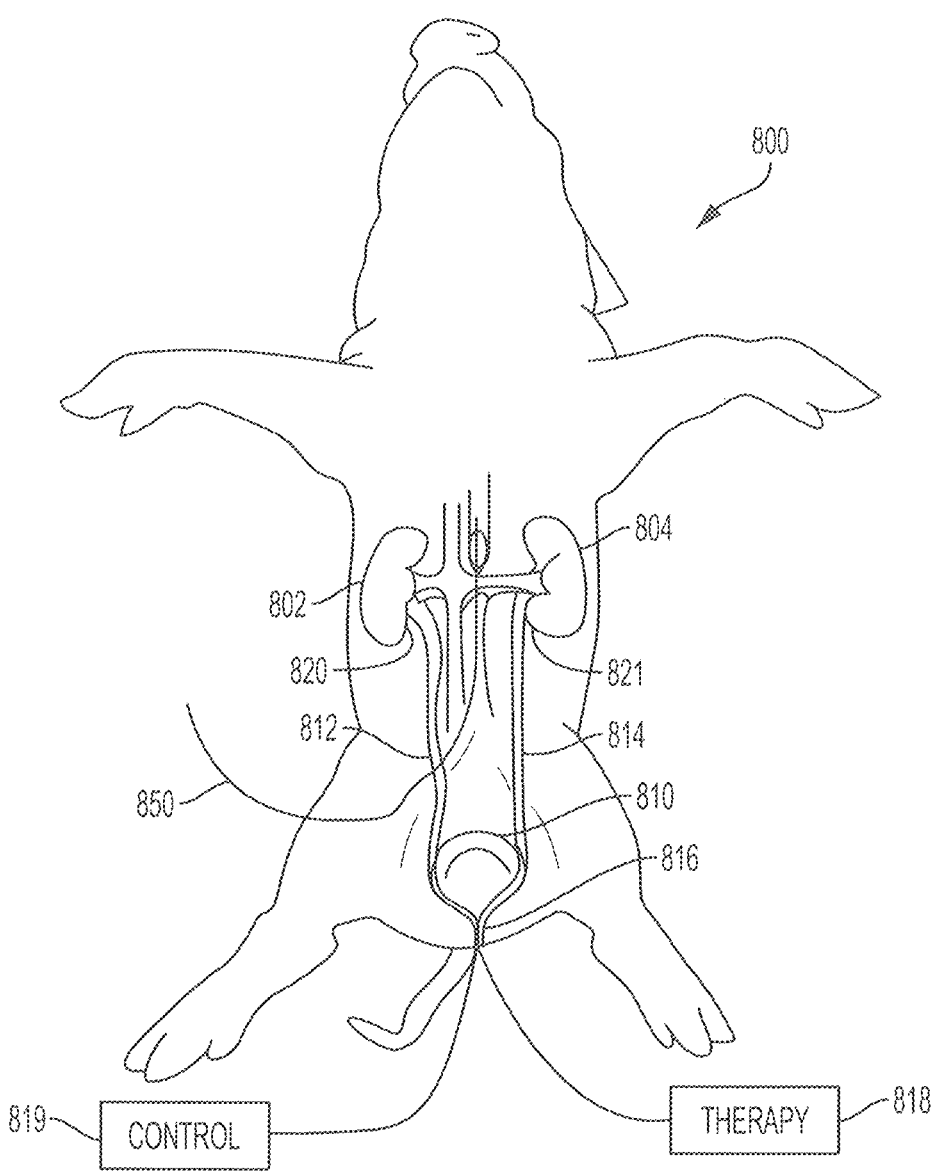
FIG. 17 is a schematic drawing of an experimental set-up for evaluating negative pressure therapy in a swine model.

Four farm swine 800 were used for purposes of evaluating effects of negative pressure therapy on renal congestion in the kidney. As shown in FIG. 17, pediatric Fogarty catheters 812, 814 were inserted to the renal pelvis region 820, 821 of each kidney 802, 804 of the four swine 800. The catheters 812, 814 were deployed within the renal pelvis region by inflating an expandable balloon to a size sufficient to seal the renal pelvis and to maintain the position of the balloon within the renal pelvis. The catheters 812, 814 extend from the renal pelvis 802, 804, through a bladder 810 and urethra 816, and to fluid collection containers external to the swine.

Urine output of two animals was collected for a 15 minute period to establish a baseline for urine output volume and rate. Urine output of the right kidney 802 and the left kidney 804 were measured individually and found to vary considerably. Creatinine clearance values were also determined.

Renal congestion (e.g., congestion or reduced blood flow in the veins of the kidney) was induced in the right kidney 802 and the left kidney 804 of the animal 800 by partially occluding the inferior vena cava (IVC) with an inflatable balloon catheter 850 just above to the renal vein outflow. Pressure sensors were used to measure IVC pressure. Normal IVC pressures were 1-4 mmHg. By inflating the balloon of the catheter 850 to approximately three quarters of the IVC diameter, the IVC pressures were elevated to between 15-25 mmHg. Inflation of the balloon to approximately three quarters of IVC diameter resulted in a 50-85% reduction in urine output. Full occlusion generated IVC pressures above 28 mmHg and was associated with at least a 95% reduction in urine output.

One kidney of each animal 800 was not treated and served as a control ("the control kidney 802"). The ureteral catheter 812 extending from the control kidney was connected to a fluid collection container 819 for determining fluid levels. One kidney ("the treated kidney 804") of each animal was treated with negative pressure from a negative pressure source (e.g., a therapy pump 818 in combination with a regulator designed to more accurately control the low magnitude of negative pressures) connected to the ureteral catheter 814. The pump 818 was an Air Cadet Vacuum Pump from Cole-Parmer Instrument Company (Model No. EW-07530-85). The pump 818 was connected in series to the regulator. The regulator was an V-800 Series Miniature Precision Vacuum Regulator—⅛ NPT Ports (Model No. V-800-10-W/K), manufactured by Airtrol Components Inc.

The pump 818 was actuated to induce negative pressure within the renal pelvis 820, 821 of the treated kidney according to the following protocol. First, the effect of negative pressure was investigated in the normal state (e.g., without inflating the IVC balloon). Four different pressure levels (−2, −10, −15, and −20 mmHg) were applied for 15 minutes each and the rate of urine produced and creatinine clearance were determined. Pressure levels were controlled and determined at the regulator. Following the −20 mmHg therapy, the IVC balloon was inflated to increase the pressure by 15-20 mmHg. The same four negative pressure levels were applied. Urine output rate and creatinine clearance rate for the congested control kidney 802 and treated kidney 804 were obtained. The animals 800 were subject to congestion by partial occlusion of the IVC for 90 minutes. Treatment was provided for 60 minutes of the 90 minute congestion period.

Following collection of urine output and creatinine clearance data, kidneys from one animal were subjected to gross examination then fixed in a 10% neutral buffered formalin. Following gross examination, histological sections were obtained, examined, and magnified images of the sections were captured. The sections were examined using an upright Olympus BX41 light microscope and images were captured using an Olympus DP25 digital camera. Specifically, photomicrograph images of the sampled tissues were obtained at low magnification (20× original magnification) and high magnification (100× original magnification). The obtained images were subjected to histological evaluation. The purpose of the evaluation was to examine the tissue histologically and to qualitatively characterize congestion and tubular degeneration for the obtained samples.

Surface mapping analysis was also performed on obtained slides of the kidney tissue. Specifically, the samples were stained and analyzed to evaluate differences in size of tubules for treated and untreated kidneys. Image processing techniques calculated a number and/or relative percentage of pixels with different coloration in the stained images. Calculated measurement data was used to determine volumes of different anatomical structures.

Results

Urine Output and Creatinine Clearance

Urine output rates were highly variable. Three sources of variation in urine output rate were observed during the study. The inter-individual and hemodynamic variability were anticipated sources of variability known in the art. A third source of variation in urine output, upon information and belief believed to be previously unknown, was identified in the experiments discussed herein, namely, contralateral intra-individual variability in urine output.

Baseline urine output rates were 0.79 ml/min for one kidney and 1.07 ml/min for the other kidney (e.g., a 26% difference). The urine output rate is a mean rate calculated from urine output rates for each animal.

When congestion was provided by inflating the IVC balloon, the treated kidney urine output dropped from 0.79 ml/min to 0.12 ml/min (15.2% of baseline). In comparison, the control kidney urine output rate during congestion dropped from 1.07 ml/min to 0.09 ml/min (8.4% of baseline). Based on urine output rates, a relative increase in treated kidney urine output compared to control kidney urine output was calculated, according to the following equation:

$$(\text{Therapy Treated}/\text{Baseline Treated})/$$
$$(\text{Therapy Control}/\text{Baseline Control}) = \text{Relative increase}$$
$$(0.12 \text{ ml/min}/0.79 \text{ ml/min})/(0.09 \text{ ml/min}/1.07 \text{ ml/min}) = 180.6\%$$

Thus, the relative increase in treated kidney urine output rate was 180.6% compared to control. This result shows a greater magnitude of decrease in urine production caused by congestion on the control side when compared to the treatment side. Presenting results as a relative percentage difference in urine output adjusts for differences in urine output between kidneys.

Figure 18:
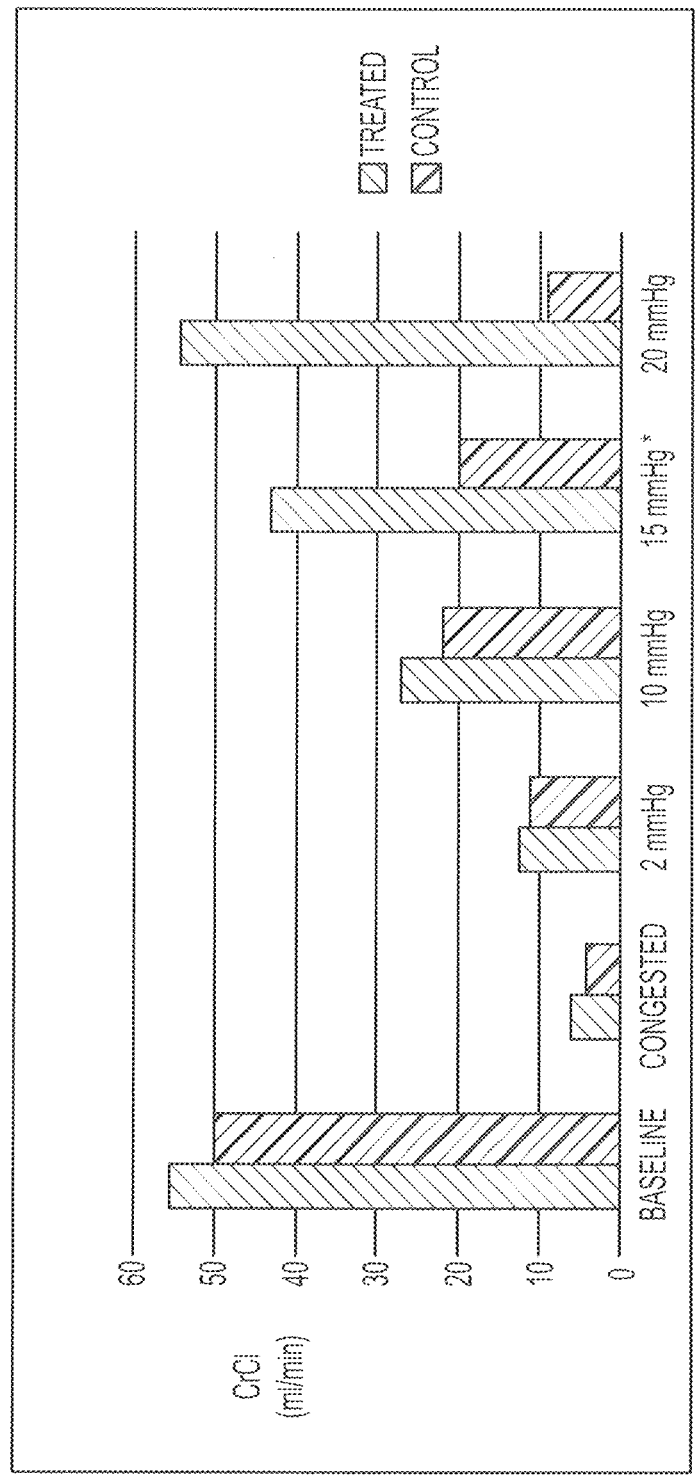
FIG. 18 is a graph of creatinine clearance rates for tests conducted using the experimental set-up shown in FIG. 17.

Creatinine clearance measurements for baseline, congested, and treated portions for one of the animals are shown in FIG. 18.

Gross Examination and Histological Evaluation

Based on gross examination of the control kidney (right kidney) and treated kidney (left kidney), it was determined that the control kidney had a uniformly dark red-brown color, which corresponds with more congestion in the control kidney compared to the treated kidney. Qualitative evaluation of the magnified section images also noted increased congestion in the control kidney compared to the treated kidney. Specifically, as shown in Table 1, the treated kidney exhibited lower levels of congestion and tubular degeneration compared to the control kidney. The following qualitative scale was used for evaluation of the obtained slides.

| Lesion | Score |
|---|---|
| Congestion | |
| None: | 0 |
| Mild: | 1 |
| Moderate: | 2 |
| Marked: | 3 |
| Severe: | 4 |
| Tubular degeneration | |
| None: | 0 |
| Mild: | 1 |
| Moderate: | 2 |
| Marked: | 3 |
| Severe: | 4 |

TABLE 1

TABULATED RESULTS

| | | Histologic lesions | | |
|---|---|---|---|---|
| Animal ID/Organ/Gross lesion | Slide number | Congestion | Tubular hyaline casts | Granulomas |
| 6343/Left Kidney/Normal | R16-513-1 | 1 | 1 | 0 |
| 6343/Left Kidney/Normal with hemorrhagic streak | R16-513-2 | 1 | 1 | 0 |
| 6343/Right Kidney/Congestion | R16-513-3 | 2 | 2 | 1 |
| 6343/Right Kidney/Congestion | R16-513-4 | 2 | 1 | 1 |

As shown in Table 1, the treated kidney (left kidney) exhibited only mild congestion and tubular degeneration. In contrast, the control kidney (right kidney) exhibited moderate congestion and tubular degeneration. These results were obtained by analysis of the slides discussed below.

Figure 19A:
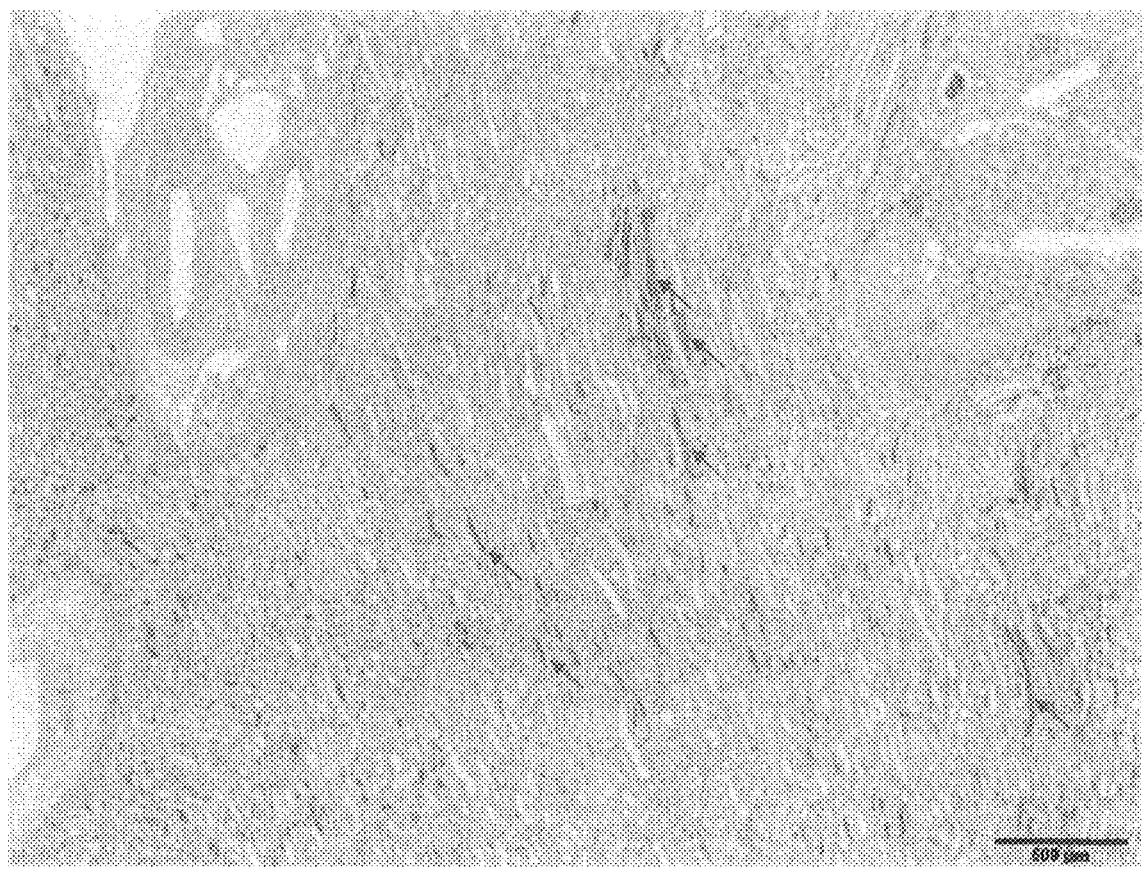
FIG. 19A is a low magnification photomicrograph of kidney tissue from a congested kidney treated with negative pressure therapy.
Figure 19B:
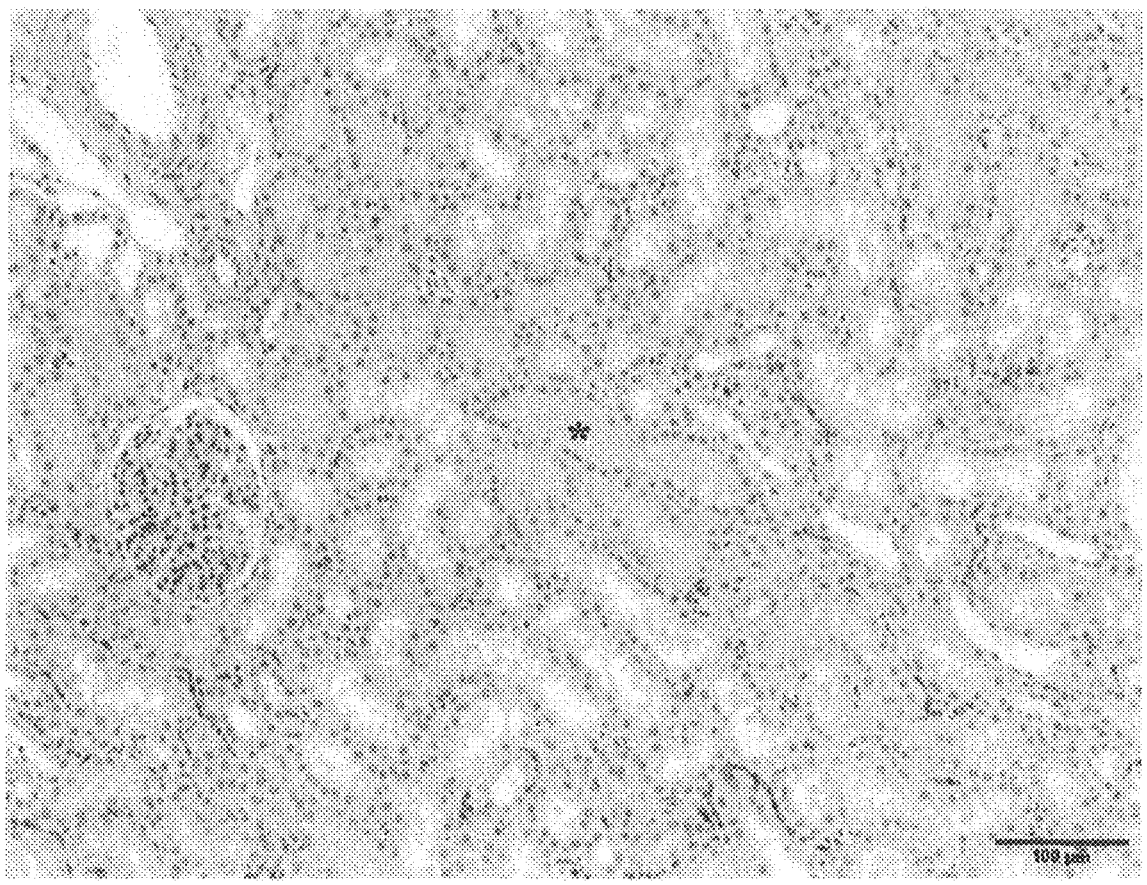
FIG. 19B is a high magnification photomicrograph of the kidney tissue shown in FIG. 19A.

FIGS. 19A and 19B are low and high magnification photomicrographs of the left kidney (treated with negative pressure) of the animal. Based on the histological review, mild congestion in the blood vessels at the corticomedullary junction was identified, as indicated by the arrows. As shown in FIG. 19B, a single tubule with a hyaline cast (as identified by the asterisk) was identified.

Figure 19C:
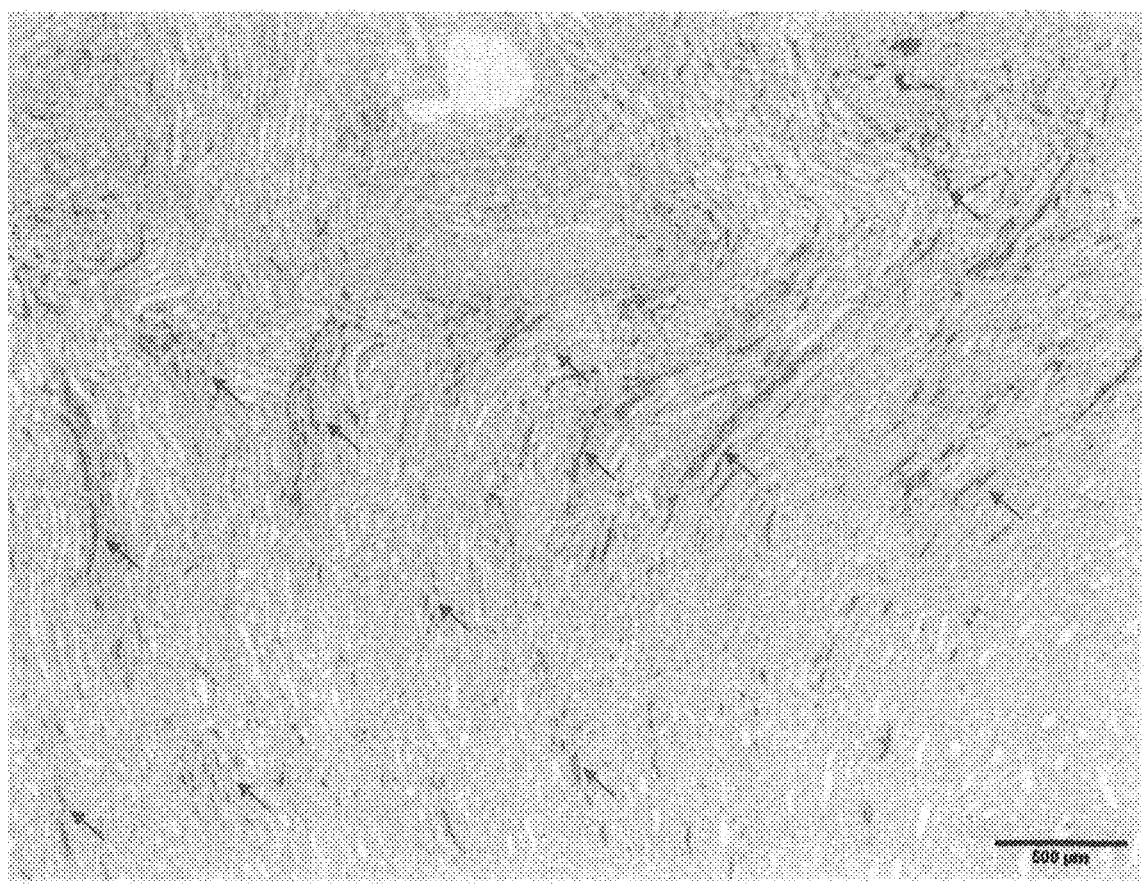
FIG. 19C is a low magnification photomicrograph of kidney tissue from a congested and untreated (e.g., control) kidney.
Figure 19D:
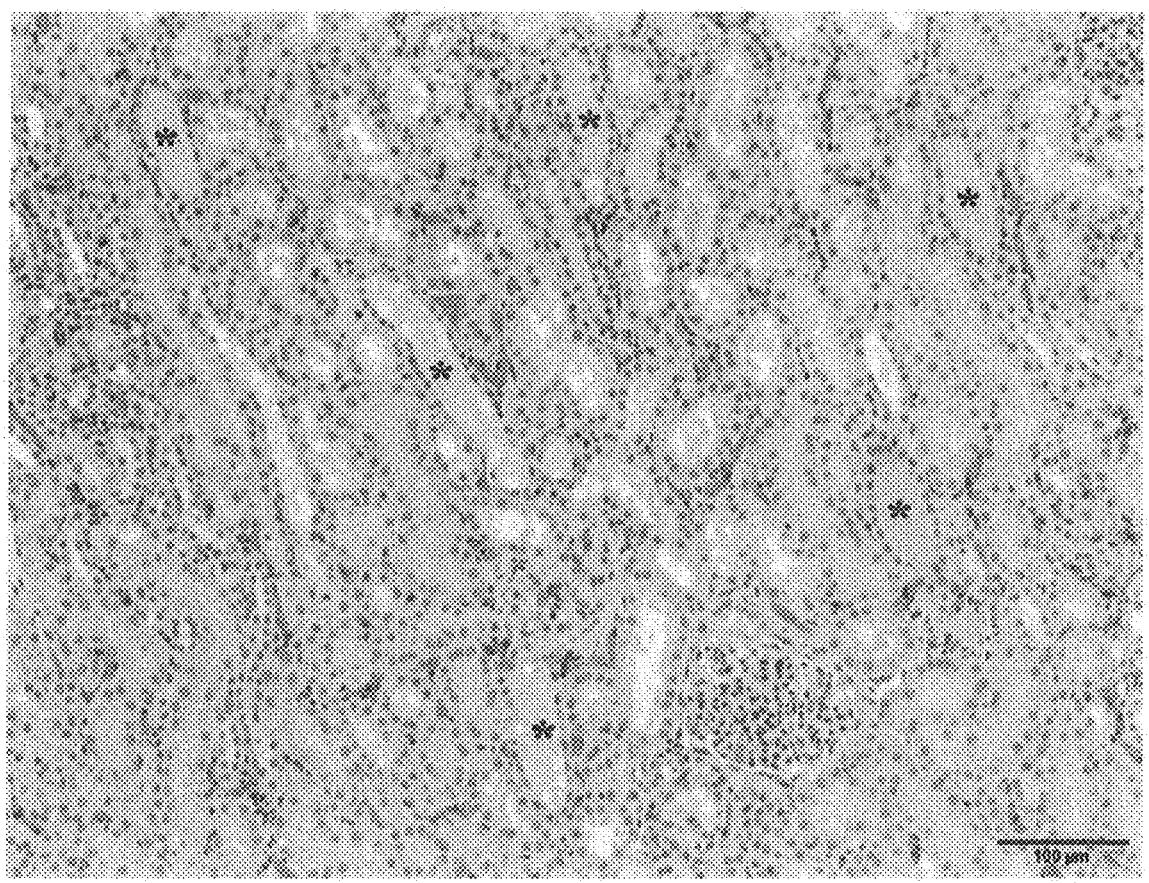
FIG. 19D is a high magnification photomicrograph of the kidney tissue shown in FIG. 19C.

FIGS. 19C and 19D are low and high resolution photomicrographs of the control kidney (right kidney). Based on the histological review, moderate congestion in the blood vessel at the corticomedullary junction was identified, as shown by the arrows in FIG. 19C. As shown in FIG. 19D, several tubules with hyaline casts were present in the tissue sample (as identified by asterisks in the image). Presence of a substantial number of hyaline casts is evidence of hypoxia.

Surface mapping analysis provided the following results. The treated kidney was determined to have 1.5 times greater fluid volume in Bowman's space and 2 times greater fluid volume in tubule lumen. Increased fluid volume in Bowman's space and the tubule lumen corresponds to increased urine output. In addition, the treated kidney was determined to have 5 times less blood volume in capillaries compared to the control kidney. The increased volume in the treated kidney appears to be a result of (1) a decrease in individual capillary size compared to the control and (2) an increase in the number of capillaries without visible red blood cells in the treated kidney compared to the control kidney, an indicator of less congestion in the treated organ.

Summary

These results indicate that the control kidney had more congestion and more tubules with intraluminal hyaline casts, which represent protein-rich intraluminal material, compared to the treated kidney. Accordingly, the treated kidney exhibits a lower degree of loss of renal function. While not intending to be bound by theory, it is believed that as severe congestion develops in the kidney, hypoxemia of the organ follows. Hypoxemia interferes with oxidative phosphorylation within the organ (e.g., ATP production). Loss of ATP and/or a decrease in ATP production inhibits the active transport of proteins causing intraluminal protein content to increase, which manifests as hyaline casts. The number of renal tubules with intraluminal hyaline casts correlates with the degree of loss of renal function. Accordingly, the reduced number of tubules in the treated left kidney is believed to be physiologically significant. While not intending to be bound by theory, it is believed that these results show that damage to the kidney can be prevented or inhibited by applying negative pressure to a catheter inserted into the renal pelvis to facilitate urine output.

Example 2

Method

Inducement of negative pressure within the renal pelvis of farm swine was performed for the purpose of evaluating effects of negative pressure therapy on hemodilution of the blood. An objective of these studies was to demonstrate whether a negative pressure delivered into the renal pelvis significantly increases urine output in a swine model of fluid resuscitation.

Two pigs were sedated and anesthetized using ketamine, midazolam, isoflurane and propofol. One animal (#6543) was treated with a ureteral catheter and negative pressure therapy as described herein. The other, which received a Foley type bladder catheter, served as a control (#6566). Following placement of the catheters, the animals were transferred to a sling and monitored for 24 hours.

Fluid overload was induced in both animals with a constant infusion of saline (125 mL/hour) during the 24 hour follow-up. Urine output volume was measured at 15 minute increments for 24 hours. Blood and urine samples were collected at 4 hour increments. As shown in FIG. 17, a therapy pump 818 was set to induce negative pressure within the renal pelvis 820, 821 (shown in FIG. 17) of both kidneys using a pressure of −45 mmHg (+/−2 mmHg).

Results

Figure 20:
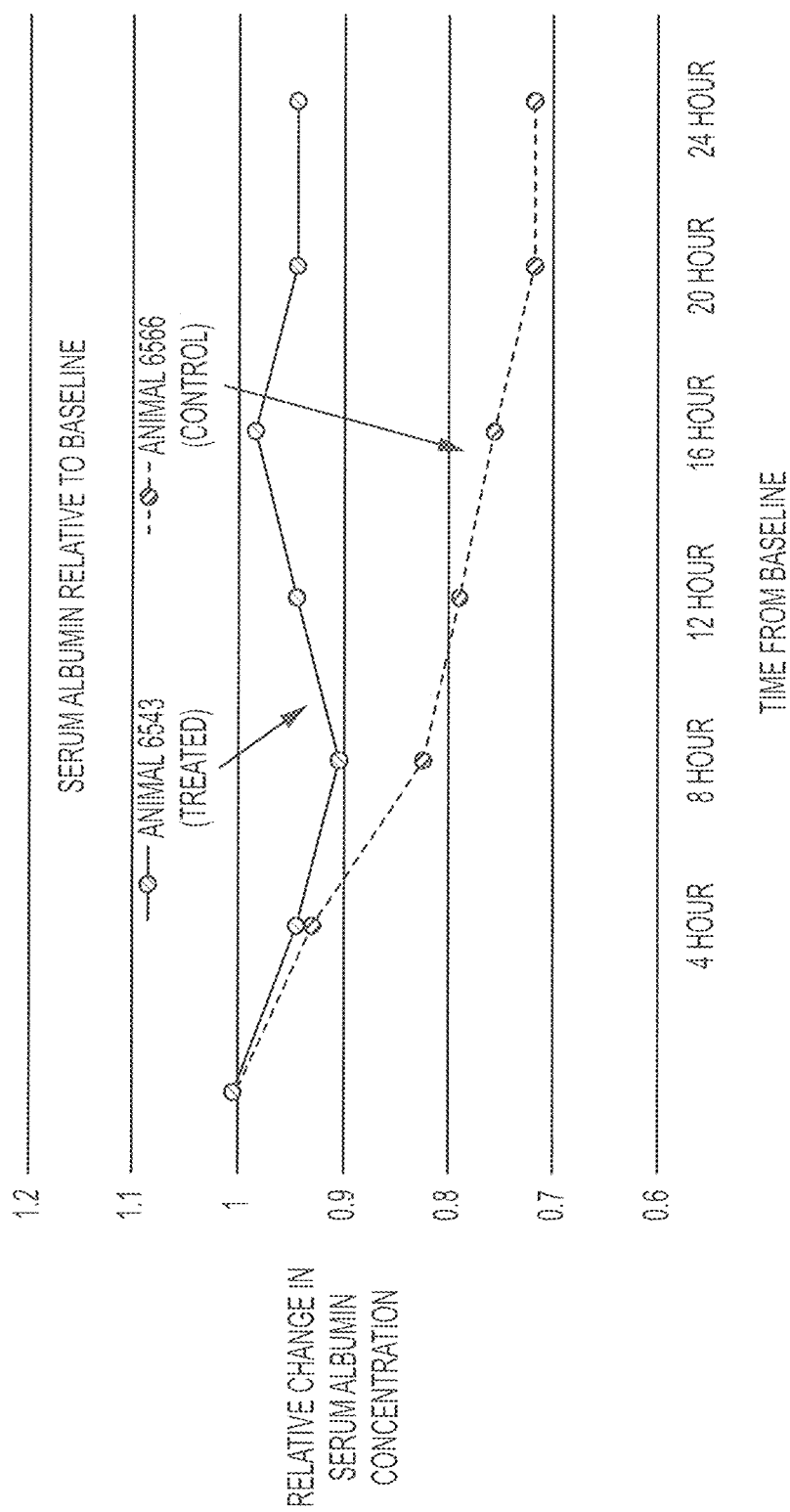
FIG. 20 is a graph of serum albumin relative to baseline for tests conduct on swine using the experimental method described herein.

Both animals received 7 L of saline over the 24 hour period. The treated animal produced 4.22 L of urine while the control produced 2.11 L. At the end of 24 hours, the control had retained 4.94 L of the 7 L administered, while the treated animal retained 2.81 L of the 7 L administered. FIG. 20 illustrates the change in serum albumin. The treated animal had a 6% drop in the serum albumin concentration over 24 hours, while the control animal had a 29% drop.

Summary

While not intending to be bound by theory, it is believed that the collected data supports the hypothesis that fluid overload induces clinically significant impact on renal function and, consequently induces hemodilution. In particular, it was observed that administration of large quantities of intravenous saline cannot be effectively removed by even healthy kidneys. The resulting fluid accumulation leads to hemodilution. The data also appears to support the hypothesis that applying negative pressure diuresis therapy to fluid overloaded animals can increase urine output, improve net fluid balance and decrease the impact of fluid resuscitation on development of hemodilution.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A catheter configured to be deployed in a urinary tract, comprising:
   (a) a proximal portion, wherein the proximal portion is essentially free or free of drainage holes; and
   (b) a distal portion comprising a retention portion configured to be deployed in a kidney and/or a renal pelvis, the retention portion comprising one or more drainage holes leading to one or more lumen(s) within the proximal portion,
   wherein the retention portion, when deployed, defines a three-dimensional shape sized and positioned to maintain patency of fluid flow between the kidney and/or renal pelvis and a proximal end of the catheter by inhibiting mucosal tissue from appreciably occluding the one or more drainage holes when negative pressure is applied through the catheter.

2. The catheter of claim 1, wherein the proximal portion is essentially free of or free of openings.

3. The catheter of claim 1, wherein a cross-sectional area of the three-dimensional shape perpendicular to a central axis of the retention portion increases towards a distal end of the retention portion.

4. The catheter of claim 3, wherein a cross-sectional area of a distal-most portion of the three-dimensional shape is greater than a cross-sectional area of the distal end of the lumen.

5. The catheter of claim 1, wherein the retention portion comprises a flexible material biased to a deployed position.

6. The catheter of claim 5, wherein the flexible material comprises a shape memory material.

7. The catheter of claim 5, wherein the flexible material comprises one or more of nitinol, titanium, chromium, silicone, polyethylene, polyethylene terephthalate, polyurethane, and/or polyvinyl chloride.

8. A method for facilitating urine output from a kidney, comprising:
   (a) inserting a catheter of claim 1 into a kidney and/or a renal pelvis; and
   (b) applying negative pressure to the lumen(s) through a proximal portion thereof for a period of time to facilitate urine output from the kidney.

9. The method of claim 8, wherein at least a portion of the retention portion is mounted to an inner surface and/or an outer surface of the lumen(s).

10. The method of claim 8, wherein the catheter is configured to be deployed in a urinary tract of a human, an animal, or a dog.

11. A negative pressure therapy system for increasing urine production, the negative pressure therapy system comprising:
   (a) a pump assembly, the pump assembly comprising:
      (i) a pump configured to provide positive or negative pressure to a kidney, and
      (ii) a controller configured to regulate the positive or negative pressure provided by the pump within a pressure range that facilitates increased urine production from the kidney,
   (b) at least one catheter according to claim 1.

12. The system of claim 11, wherein the patient is a human, an animal, or a dog.

13. The system of claim 11, wherein the catheter is configured to be deployed in a urinary tract of a human, an animal, or a dog.

14. The catheter of claim 1, wherein the catheter is configured to be deployed in a urinary tract of a human.

15. The catheter of claim 1, wherein the catheter is configured to be deployed in a urinary tract of an animal.

16. The catheter of claim 1, wherein the catheter is configured to be deployed in a urinary tract of a dog.

17. A system for inducing negative pressure in a portion of a urinary tract, the system comprising:
   at least one catheter comprising:
   (a) a proximal portion, wherein the proximal portion is essentially free or free of drainage holes; and
   (b) a distal portion comprising a retention portion configured to be deployed in a kidney and/or a renal pelvis, the retention portion comprising one or more drainage holes leading to one or more lumen(s) within the proximal portion,
   wherein the retention portion, when deployed, defines a three-dimensional shape sized and positioned to maintain patency of fluid flow between the kidney and/or renal pelvis and a proximal end of the catheter by inhibiting mucosal tissue from appreciably occluding the one or more drainage holes when negative pressure is applied through the catheter; and
   a negative pressure source in fluid communication with the lumen, the negative pressure source being configured for inducing a negative pressure in a portion of the urinary tract to draw fluid through the lumen of the catheter.

18. The system of claim 17, wherein the negative pressure source is a pump.

19. The system of claim 18, wherein the pump is configured to generate positive or negative pressure in a proximal end of the lumen.

20. The system of claim 18, wherein the pump applies a negative pressure of about 100 mmHg or less to a proximal end of the lumen.

21. The system of claim 18, wherein the pump is configured to operate at one of three pressure levels, the pressure levels generating a negative pressure of 2 to 125 mmHg.

22. The system of claim 18, wherein the pump is configured to alternate between generating negative pressure and generating positive pressure.

23. The system of claim 18, wherein the pump has an accuracy of about 10 mmHg or less.

24. A ureteral catheter, comprising:
- an elongated tube comprising a proximal end, a distal end, and a sidewall extending between the proximal end and the distal end of the tube defining at least one drainage lumen extending through the tube, wherein a proximal portion of the elongated tube is essentially free of or free of drainage holes; and
- a retention portion which defines a three-dimensional shape to inhibit tissue of the ureter or renal pelvis from occluding the at least one drainage lumen at the distal end of the elongated tube upon application of negative pressure through the drainage lumen, wherein the three-dimensional space defined by the retention portion encloses at least a portion of the distal end of the elongated tube.

25. The ureteral catheter of claim 24, wherein a cross-sectional area of the three-dimensional shape perpendicular to a central axis of the retention portion increases towards a distal end of the retention portion.

26. The ureteral catheter of claim 25, wherein a cross-sectional area of a distal-most portion of the three-dimensional shape is greater than a cross-sectional area of the distal end of the tube.

27. The ureteral catheter of claim 24, wherein the retention portion comprises a flexible material biased to a deployed position.

\* \* \* \* \*

UNITED STATES PATENT AND TRADEMARK OFFICE
CERTIFICATE OF CORRECTION

PATENT NO. : 11,918,754 B2
APPLICATION NO. : 17/173262
DATED : March 5, 2024
INVENTOR(S) : John R. Erbey, II et al.

It is certified that error appears in the above-identified patent and that said Letters Patent is hereby corrected as shown below:

On the Title Page

Page 2, Column 1, Item (63) Related U.S. Application Data, Line 2, delete "and" and insert -- which is --

Signed and Sealed this
Fourteenth Day of May, 2024

Katherine Kelly Vidal
*Director of the United States Patent and Trademark Office*